(12) United States Patent
Wingeier et al.

(10) Patent No.: US 9,186,082 B2
(45) Date of Patent: Nov. 17, 2015

(54) SPATIOTEMPORAL PATTERN RECOGNITION FOR NEUROLOGICAL EVENT DETECTION AND PREDICTION IN AN IMPLANTABLE DEVICE

(75) Inventors: Brett M. Wingeier, San Francisco, CA (US); Thomas K. Tcheng, Pleasant Hill, CA (US)

(73) Assignee: NeuroPace, Inc., Mountain View, CA (US)

(*) Notice: Subject to any disclaimer, the term of this patent is extended or adjusted under 35 U.S.C. 154(b) by 1634 days.

(21) Appl. No.: 11/811,190

(22) Filed: Jun. 7, 2007

(65) Prior Publication Data

US 2007/0244408 A1    Oct. 18, 2007

Related U.S. Application Data

(62) Division of application No. 10/244,093, filed on Sep. 13, 2002, now Pat. No. 7,277,748.

(51) Int. Cl.
| | |
|---|---|
| *A61B 5/04* | (2006.01) |
| *A61B 5/0476* | (2006.01) |
| *A61B 5/048* | (2006.01) |
| *A61B 5/0484* | (2006.01) |
| *A61B 5/00* | (2006.01) |
| A61B 5/07 | (2006.01) |

(52) U.S. Cl.
CPC ............ *A61B 5/0476* (2013.01); *A61B 5/0031* (2013.01); *A61B 5/048* (2013.01); *A61B 5/0484* (2013.01); *A61B 5/4094* (2013.01); *A61B 5/076* (2013.01)

(58) Field of Classification Search
None
See application file for complete search history.

(56) References Cited

U.S. PATENT DOCUMENTS

| | | | |
|---|---|---|---|
| 4,631,957 A * | 12/1986 | Ruhenstroth-Bauer | .... 73/170.24 |
| 5,857,978 A | 1/1999 | Hively et al. | |
| 5,995,868 A | 11/1999 | Dorfmeister | |
| 6,006,124 A | 12/1999 | Fischell et al. | |
| 6,016,449 A | 1/2000 | Fischell et al. | |
| 6,018,682 A | 1/2000 | Rise | |
| 6,366,813 B1 | 4/2002 | DiLorenzo | |
| 6,473,639 B1 | 10/2002 | Fischell et al. | |
| 6,819,956 B2 | 11/2004 | DiLorenzo | |
| 7,599,736 B2 | 10/2009 | DiLorenzo | |

(Continued)

OTHER PUBLICATIONS

J. Gotman, Automatic Seizure Detection: Improvements and Evaluation, Electroencephalogr. Clin. Neurophysiol. 1990, 76(4): 317-24.

(Continued)

*Primary Examiner* — Russell S Negin
(74) *Attorney, Agent, or Firm* — Arent Fox LLP

(57) ABSTRACT

A system and method for detecting and predicting neurological events with an implantable device uses a relatively low-power central processing unit in connection with signal processing circuitry to identify features (including half waves) and calculate window-based characteristics (including line lengths and areas under the curve of the waveform) in one or more electrographic signals received from a patient's brain. The features and window-based characteristics are employed within the framework of a programmable finite state machine to identify patterns and sequences in and across the electrographic signals, facilitating early and reliable detection and prediction of complex spatiotemporal neurological events in real time, and enabling responsive action by the implantable device.

10 Claims, 34 Drawing Sheets

(56) References Cited

U.S. PATENT DOCUMENTS

| | | |
|---|---|---|
| 2002/0095099 A1 | 7/2002 | Quyen |
| 2003/0004428 A1 | 1/2003 | Pless |
| 2004/0068199 A1 | 4/2004 | Echauz |
| 2004/0122335 A1 | 6/2004 | Sackellares |

OTHER PUBLICATIONS

H. Qu and J. Gotman, A Seizure Warning System for Long-Term Epilepsy Monitoring, Neurology 1995; 45: 2250-4.

H. Qu and J. Gotman, A Patient-Specific Algorithm for the Detection of Seizure Onset in Long-Term EEG Monitoring: Possible Use as a Warning Device, 1997.

Spencer S.S., Guimaraes P., Katz A., Kim J., Spencer D., Morphological Patterns of Seizures Recorded Intracranially, Epilepsia 1992; 33: 537-545.

Lee S.A., Spencer D. D., Spencer S. S., Intracranial EEG Seizure-Onset Patterns in NeoCortical Epilepsy, Epilepsia 2000; 41: 297-307.

Schiff S.J., Colella D., Jacyna G.M. et al., Brain Chirps: Spectrographic Signatures of Epileptic Seizures; Clin. Neurophysiol. 2000; 111: 953-958.

Bergey G.K., Franaszczuk P.J., Epileptic Seizures are Characterized by Changing Signal Complexity, Clin. Neurophysiol. 2001; 112: 241-249.

Velasco A.L., Wilson C.L., Babb T.L., Engel J. Jr., Functional and Anatomic Correlates of Two Frequently Observed Temporal Lobe Seizure-Onset Patterns, Neural Plasticity, 2000, 7:49-63.

Schiller Y., Cascino G.D., Busacker N.E., Sharbrough F. W., Characterization and Comparison of Local Onset and Remote Propagated Electrographic Seizures Recorded with Intra-cranial electrodes; Epilepsia 1998; 39; 380-388.

Litt B., Esteller R., Echauz J. et al., Epileptic Seizures May Begin Hours in Advance of Clinical Onset: A Report of Five Patients, Neuron, 2001: 30: 51-64.

Wagner, H.R. et al., Suppression of Cortical Epileptiform Activity by Generalized and Localized ECoG Desynchronization, Electroencephalogr. Clin. Neurophysiol., 1975; 39(5): 499-506.

http://www.medtronic.com/physician/activa/index.html (Medtronic Activa).

U.S. Appl. No. 60/095,413, filed Aug. 5, 1998.

http://www.vnstherapy.com/epilepsylhcplvnstherapyldefaull.aspx (NeuroCybemetic Prosthesis (NCP», Accessed Jun. 5, 2007.

Terry, Reese et al., "An Implantable Neurocybernetic Prothesis System", *Epilepsia*, 31 (Suppl. 2): S33-S37, Cyberonics, Inc, (1990).

* cited by examiner

SPATIOTEMPORAL PATTERN RECOGNITION FOR NEUROLOGICAL EVENT DETECTION AND PREDICTION IN AN IMPLANTABLE DEVICE

CROSS REFERENCE TO RELATED APPLICATION

This is a divisional of U.S. patent application Ser. No. 10/244,093, filed Sep. 13, 2002.

FIELD OF THE INVENTION

The invention relates to systems and methods for detecting and predicting neurological dysfunction characterized by abnormal electrographic patterns, and more particularly to a system and method for detecting and predicting epileptic seizures and their onsets by analyzing temporal and spatiotemporal patterns and sequences of electroencephalogram and electrocorticogram signals with an implantable device.

BACKGROUND OF THE INVENTION

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenytoin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20-30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices apply continuous electrical stimulation to neural tissue surrounding or near implanted electrodes, and do not perform any detection—they are not responsive to relevant neurological conditions.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide substantial clinical benefit.

The Activa device from Medtronic is a pectorally implanted continuous deep brain stimulator intended primarily to treat Parkinson's disease. In operation, it supplies a continuous electrical pulse stream to a selected deep brain structure where an electrode has been implanted. Continuous stimulation of deep brain structures for the treatment of epilepsy has not met with consistent success. To be effective in terminating seizures, it is believed that one effective site where stimulation should be performed is near the focus of the epileptogenic region. The focus is often in the neocortex, where continuous stimulation may cause significant neurological deficit with clinical symptoms including loss of speech, sensory disorders, or involuntary motion. Accordingly, research has been directed toward automatic responsive epilepsy treatment based on a detection of imminent seizure.

A typical epilepsy patient experiences episodic attacks or seizures, which are generally electrographically defined as periods of abnormal neurological activity. As is traditional in the art, such periods shall be referred to herein as "ictal".

Most prior work on the detection and responsive treatment of seizures via electrical stimulation has focused on analysis of electroencephalogram (EEG) and electrocorticogram (ECoG) waveforms. In common usage, the term "EEG" is often used to refer to signals representing aggregate neuronal activity potentials detectable via electrodes applied to a patient's scalp, though the term can also refer to signals obtained from deep in the patient's brain via depth electrodes and the like. Specifically, "ECoGs" refer to signals obtained from internal electrodes near the surface of the brain (generally on or under the dura mater); an ECoG is a particular type of EEG. Unless the context clearly and expressly indicates otherwise, the term "EEG" shall be used generically herein to refer to both EEG and ECoG signals, regardless of where in the patient's brain the electrodes are located.

Much of the work on detection has focused on the use of time-domain analysis of EEG signals. See, e.g., J. Gotman, Automatic seizure detection: improvements and evaluation, Electroencephalogr. Clin. Neurophysiol. 1990; 76(4): 317-24. In a typical time-domain detection system, EEG signals are received by one or more implanted electrodes and then processed by a control module, which then is capable of performing an action (intervention, warning, recording, etc.) when an abnormal neurological event is detected.

It is generally preferable to be able to detect and treat a seizure at or near its beginning, or even before it begins. The beginning of a seizure is referred to herein as an "onset." However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there are changes in the EEG that occur seconds or even minutes before the electrographic onset that can be identified and used to facilitate intervention before electrographic or clinical onsets occur. This capability would be considered seizure prediction, in contrast to the detection of a seizure or its onset.

In the Gotman system, EEG waveforms are filtered and decomposed into "features" representing characteristics of interest in the waveforms. One such feature is characterized by the regular occurrence (i.e., density) of half-waves exceeding a threshold amplitude occurring in a specified frequency band between approximately 3 Hz and 20 Hz, especially in comparison to background (non-ictal) activity. When such half-waves are detected, it is believed that seizure activity is occurring For related approaches, see also H. Qu and J. Gotman, A seizure warning system for long term epilepsy monitoring, Neurology 1995; 45: 2250-4; and H. Qu and J. Gotman, A Patient-Specific Algorithm for the Detection of Seizure Onset in Long-Term EEG Monitoring: Possible Use as a Warning Device, IEEE Trans. Biomed. Eng. 1997; 44(2): 115-22.

The Gotman articles address half wave characteristics in general, and introduce a variety of measurement criteria, including a ratio of current epoch amplitude to background; average current epoch EEG frequency; average background EEG frequency; coefficient of variation of wave duration; ratio of current epoch amplitude to the amplitude of the following time period; average wave amplitude; average wave duration; dominant frequency (peak frequency of the dominant peak); and average power in a main energy zone. These criteria are variously mapped into an n-dimensional space, and whether a seizure is detected depends on the vector distance between the parameters of a measured segment of EEG and a seizure template in that space.

It should be noted that the schemes set forth in the above articles are not tailored for use in an implantable device, and hence typically require more computational ability than would be available in such a device.

U.S. Pat. No. 6,018,682 to Rise describes an implantable seizure warning system that implements a form of the Gotman system. However, the system described therein uses only a single detection modality, namely a count of sharp spike and wave patterns within a time period. This is accomplished with relatively complex processing, including averaging over time and quantifying sharpness by way of a second derivative of the signal. The Rise patent does not disclose how the signals are processed at a low level, nor does it explain detection criteria in any specific level of detail.

A more computationally demanding approach is to transform EEG signals into the frequency domain for rigorous spectrum analysis. See, e.g., U.S. Pat. No. 5,995,868 to Dorfmeister et al., which analyzes the power spectral density of EEG signals in comparison to background characteristics. Although this approach is generally believed to achieve good results, for the most part, its computational expense renders it less than optimal for use in long-term implanted epilepsy monitor and treatment devices. With current technology, the battery life in an implantable device computationally capable of performing the Dorfmeister method would be too short for it to be feasible.

Also representing an alternative and more complex approach is U.S. Pat. No. 5,857,978 to Hively et al., in which various non-linear and statistical characteristics of EEG signals are analyzed to identify the onset of ictal activity. Once more, the calculation of statistically relevant characteristics is not believed to be feasible in an implantable device.

U.S. Pat. No. 6,016,449 to Fischell, et al. (which is hereby incorporated by reference as though set forth in full herein), describes an implantable seizure detection and treatment system. In the Fischell system, various detection methods are possible, all of which essentially rely upon the analysis (either in the time domain or the frequency domain) of processed EEG signals. Fischell's controller is preferably implanted intracranially, but other approaches are also possible, including the use of an external controller. The processing and detection techniques applied in Fischell are generally well suited for implantable use. When a seizure is detected, the Fischell system applies responsive electrical stimulation to terminate the seizure, a capability that will be discussed in further detail below.

All of these approaches provide useful information, and in some cases may provide sufficient information for accurate detection and prediction of most imminent epileptic seizures.

However, the known approaches generally observe electrographic patterns at a single moment in time (or over a region of time reduced to one or more features); they do not differentiate between different patterns or sequences of electrographic activity, separated in time or space. It is believed that spatiotemporal patterns and sequences may serve to distinguish activity of interest from background activity, where looking at small portions of signals in isolation might not.

Neurological events are often characterized by evolving patterns and sequences of activity. For example, seizure onsets are often defined by different morphological patterns. See, e.g., Spencer S S, Guimaraes P, Katz A, Kim J, Spencer D. Morphological patterns of seizures recorded intracranially. Epilepsia 1992; 33: 537-545; and Lee S A, Spencer D D, Spencer S S. Intracranial EEG seizure-onset patterns in neocortical epilepsy. Epilepsia 2000; 41: 297-307.

Even within an onset or seizure, the most prominent characteristic may be changes in a signal rather than the signal itself at a snapshot in time. Schiff S J, Colella D, Jacyna G M et al. Brain chirps: spectrographic signatures of epileptic seizures. Clin. Neurophysiol. 2000; 111: 953-958; and Bergey G K, Franaszczuk P J. Epileptic seizures are characterized by changing signal complexity. Clin. Neurophysiol. 2001; 112: 241-249.

Spatial patterns (e.g., where an onset occurs) may be related to temporal patterns and signal morphology, and vice versa. It is believed that the most successful treatment strategies may be dependent upon seizure origin and type. Velasco A L, Wilson C L, Babb T L, Engel J Jr. Functional and anatomic correlates of two frequently observed temporal lobe seizure-onset patterns. Neural Plast. 2000; 7: 49-63. Thus, it would be desirable to be able to identify different patterns and morphologies to provide the best possible therapy to the patient.

Spatial patterns, represented by activity from different parts of the brain at the same time or at different times, may also come into play. For example, if it can be determined that seizure activity has propagated from one location to another, it may be advantageous to apply a therapy that takes that into account (rather than performing focal stimulation wherever the activity is first seen). See, e.g., Schiller Y, Cascino G D, Busacker N E, Sharbrough F W. Characterization and comparison of local onset and remote propagated electrographic seizures recorded with intracranial electrodes. Epilepsia 1998; 39: 380-388. An indication that a seizure has originated in a certain part of the brain may lead to improved treatment possibilities.

It has also been shown that electrographic signatures start to evolve long before a seizure begins. Litt B, Esteller R, Echauz J et al. Epileptic seizures may begin hours in advance of clinical onset: a report of five patients. Neuron 2001; 30: 51-64. Accordingly, seizure prediction may be accomplished by identifying this slow evolution of signal characteristics over time, leading to the possibility of effective preventative therapy. Present state-of-the-art seizure and neurological event detection technologies are generally based upon a single combination of characteristics—representative of a current neurological point in time or derived from a feature that tends to smear together signal characteristics over a time period.

Accordingly, and for the reasons set forth above, it would be advantageous to have the benefit of a neurological event detector that is capable of resolving time sequences and correlating spatial patterns. Such a detector would be capable of identifying temporal, spatial, and spatiotemporal patterns and sequences of neurological activity. As described above, this would tend to facilitate improved detection performance, improved therapy, and the possibility of accurate seizure prediction.

Two types of detection errors are generally possible. A "false positive," as the term is used herein, refers to a detection of a seizure or ictal activity when no seizure or other abnormal event is actually occurring. Similarly, a "false negative" herein refers to the failure to detect a seizure or ictal activity that actually is occurring or shortly will occur.

In most cases, with all known implementations of the known approaches to detecting abnormal seizure activity solely by monitoring and analyzing individual segments of EEG activity, when a seizure detection algorithm is tuned to catch all seizures, there will be a significant number of false positives. While it is currently believed that there are minimal or no side effects to limited amounts of over-stimulation (e.g., providing stimulation sufficient to terminate a seizure in response to a false positive), the possibility of accidentally initiating a seizure or increasing the patient's susceptibility to seizures must be considered.

As is well known, it has been suggested that it is possible to treat and terminate seizures by applying electrical stimulation to the brain. See, e.g., U.S. Pat. No. 6,016,449 to Fischell et al., and H. R. Wagner, et al., Suppression of cortical epileptiform activity by generalized and localized ECoG desynchronization, Electroencephalogr. Clin. Neurophysiol. 1975; 39(5): 499-506. And as stated above, it is believed to be beneficial to perform this stimulation only when a seizure (or other undesired neurological event) is occurring or about to occur, as inappropriate stimulation may result in the initiation of seizures.

Furthermore, it should be noted that a false negative (that is, a seizure that occurs without any warning or treatment from the device) will often cause the patient significant discomfort and detriment. Clearly, false negatives are to be avoided.

It has been found to be difficult to achieve an acceptably low level of false positives and false negatives with the level of computational ability available in an implantable device with reasonable battery life.

Preferably, the battery in an implantable device, particularly one implanted intracranially, should last at least several years. There is a substantial risk of complications (such as infection, blood clots, and the overgrowth of scar tissue) and lead failure each time an implanted device or its battery is replaced. Rechargeable batteries have not been found to provide any advantage in this regard, as they are not as efficient as traditional cells, and the additional electronic circuitry required to support the recharging operation contributes to the device's size and complexity. Moreover, there is a need for patient discipline in recharging the device batteries, which calls for the frequent transmission of a substantial amount of power over a wireless link and through the patient's skin and other tissue.

As stated above, the detection and prediction of ictal activity has traditionally required a significant amount of computational ability. Moreover, for an implanted device to have significant real-world utility, it is also advantageous to include a number of other features and capabilities. Specifically, treatment (via electrical stimulation or drug infusion) and/or warning (via an audio annunciator, for example), recording of EEG signals for later consideration and analysis, and telemetry providing a link to external equipment are all useful capabilities for an implanted device capable of detecting or predicting epileptiform signals. All of these additional subsystems will consume further power.

Moreover, size is also a consideration. For various reasons, intracranial implants are favored. A device implanted intracranially (or under the scalp) will typically have a lower risk of failure than a similar device implanted pectorally or elsewhere, which require a lead to be run from the device, through the patient's neck to the electrode implantation sites in the patient's head. This lead is also prone to receive additional electromagnetic interference.

As is well known in the art, the computational ability of a processor-controlled system is directly related to both size and power consumption. In accordance with the above considerations, therefore, it would be advantageous to have sufficient detection and prediction capabilities to avoid a substantial number of false positive and false negative detections, and yet consume little enough power (in conjunction with the other subsystems) to enable long battery life. Such an implantable device would have a relatively low-power central processing unit to reduce the electrical power consumed by that portion.

At the current time, there is no known implantable device that is capable of detecting and predicting seizures based on spatiotemporal patterns and sequences.

SUMMARY OF THE INVENTION

Accordingly, an implantable device according to the invention for detecting and predicting epileptic seizures includes a relatively low-speed and low-power central processing unit, as well as customized electronic circuit modules in a detection subsystem. As described herein, the detection subsystem also performs prediction, which in the context of the present application is a form of detection that occurs before identifiable clinical symptoms or even obvious electrographic patterns are evident upon inspection. The sane methods, potentially with different parameters, are adapted to be used for both detection and prediction. Generally, as described herein, a neurological event (such as an epileptic seizure) may be detected, an electrographic "onset" of such a neurological event (an electrographic indication of an event occurring at the same time as or before the clinical event begins) may be detected (and may be characterized by different waveform observations than the event itself), and a "precursor" to a neurological event (electrographic activity regularly occurring some time before the clinical event) may be detected as predictive of the neurological event.

As described herein and as the terms are generally understood, the present approach is generally not statistical or stochastic in nature. The invention, and particularly the detection subsystem thereof, is specifically adapted to perform much of the signal processing and analysis requisite for accurate and effective neurological event detection. The central processing unit remains in a suspended "sleep" state characterized by relative inactivity a substantial percentage of the time, and is periodically awakened by interrupts from the detection subsystem to perform certain tasks related to the detection and prediction schemes enabled by the device.

Much of the processing performed by an implantable system according to the invention involves operations on digital data in the time domain. Preferably, to reduce the amount of data processing required by the invention, samples at ten-bit resolution are taken at a rate less than or equal to approximately 500 Hz (2 ms per sample).

As stated above, an implantable system according to the invention is capable of accurate and reliable seizure detection and prediction. To accomplish this, the invention employs a combination of signal processing and analysis modalities, including data reduction and feature extraction techniques, mostly implemented as customized digital electronics modules, minimally reliant upon a central processing unit.

In particular, it has been found to be advantageous to utilize two different data reduction methodologies, both of which collect data representative of EEG signals within a sequence of uniform time windows each having a specified duration.

The first data reduction methodology involves the calculation of a "line length function" for an EEG signal within a time window. The second data reduction methodology involves the calculation of an "area function" represented by an EEG signal within a time window. The central processing unit receives the line length function and area function measurements performed by the detection subsystem, and is capable of acting based on those measurements or their trends.

Feature extraction, specifically the identification of half waves in an EEG signal, also provides useful information. A half wave is an interval between a local waveform minimum and a local waveform maximum; each time a signal "changes direction" (from increasing to decreasing, or vice versa), subject to limitations that will be set forth in further detail below, a new half wave is identified.

To capture and identify patterns and sequences of activity, such as the evolving signals that characterize seizure onsets and pre-onset activity, the invention employs a programmable finite state machine architecture to model the behavior of the patient's brain in the moments (seconds, minutes, or even hours) leading up to a seizure or other neurological event of interest. The state machine employed by the invention is capable of identifying patterns and sequences over time and space, thereby distinguishing complex seizure or onset signal activity from background activity that might otherwise contain certain signal characteristics that are similar to those in the seizure or onset.

The approach set forth herein is similar in some ways to template matching, but with extensive programmability and configurability. Flexibility in configurations, times, and sequences is facilitated by an implementation of a finite state machine that is well suited for use in a low power implantable device.

Accordingly, in one embodiment of the invention, a system according to the invention includes a central processing unit, as well as a detection subsystem that further includes a waveform analyzer. The waveform analyzer includes waveform feature analysis capabilities (such as half wave characteristics) as well as window-based analysis capabilities (such as line length and area under the curve), and both aspects are combined to provide enhanced neurological event detection. Custom finite state machines are programmed and employed within the system to identify patterns and sequences within the electrographic activity that makes up the neurological event of interest. A central processing unit is used to consolidate the results from multiple channels and coordinate responsive action when necessary.

The method is generally performed by analyzing electrographic signals with the line length, area, and half wave analysis tools described above, and employing a time-dependent finite state machine to identify a sequence or pattern of wave characteristics, either from a single general location in the patient's brain or from multiple locations over time. The process is relatively computationally efficient, in that dedicated hardware subsystems are employed where possible to reduce power consumption and allow the central processing unit to remain in a relatively low power state for as much time as possible.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

Figure 1:
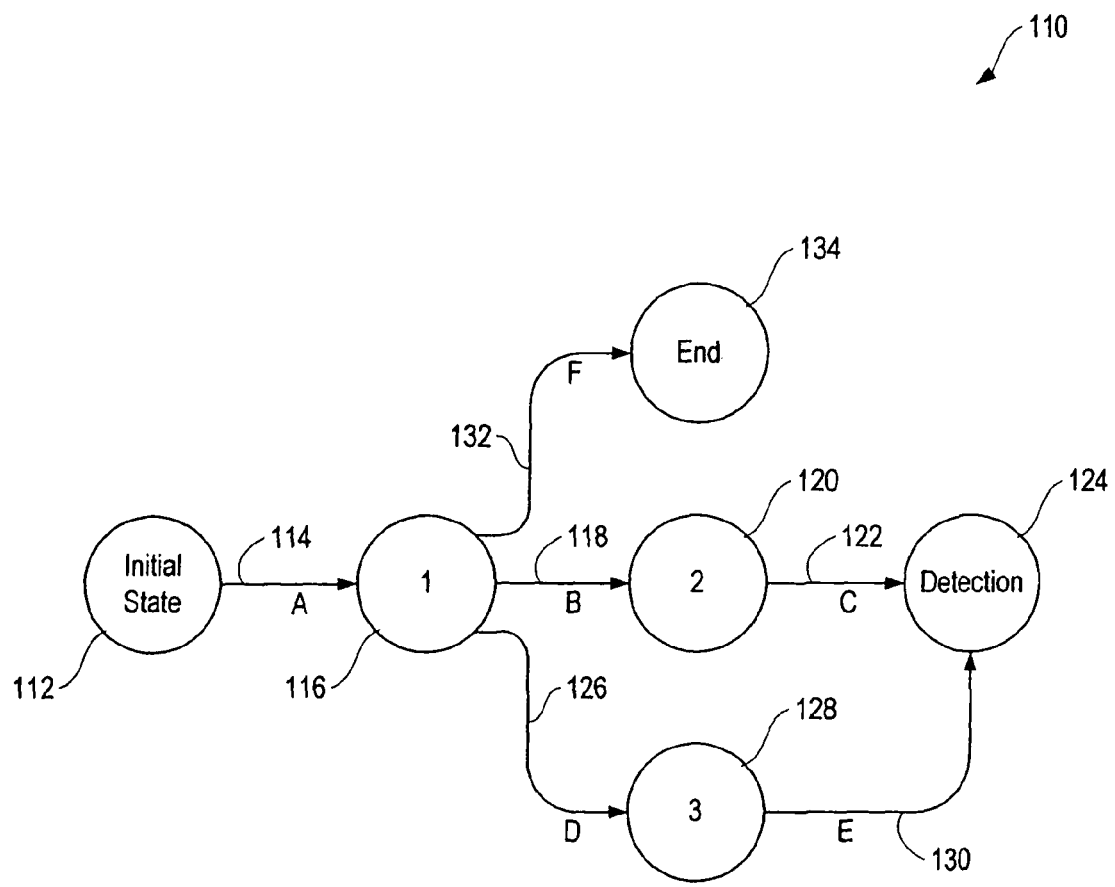
FIG. 1 is an exemplary time-independent state transition diagram representing a finite state machine and including several possible sequences of signal events leading to a neurological event detection according to the invention.

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

As described above, a system according to the invention is capable of identifying patterns and sequences, both in time and across various locations in the brain, for the purpose of detecting and in some cases predicting neurological events of interest. In the disclosed embodiment of the invention, specially adapted and implemented finite state machines are employed to achieve this objective. These state machines are described in detail below.

A finite state machine is a mathematical model capable of representing the behavior of a system based on its current state and inputs the system is exposed to. Typically, and as employed herein, a state machine includes an initial state and multiple additional states to which transitions can be made. Inputs, in the present example system events (such as individual signal events detected by a system according to the invention) cause the state machine to selectively transition from state to state until a desired state is reached—either an "end" state indicating that a desired sequence was not observed, or a "detection" state indicating that a desired sequence was observed. Accordingly, a state machine according to the invention serves as a sort of grammar for encoding patterns and sequences of events of interest, namely, physiological (or neurological) events from one or more locations in the patient's brain or elsewhere, as well as system conditions. This framework allows for the identification of such patterns and sequences that traditional feature-extracting and window-processing detection schemes are often unable to discriminate from baseline data.

For purposes of this disclosure, a "neurological event" is generally a clinically significant occurrence marked by at least one detectable change in a physiological variable, such as a sequence or pattern of one or more separately detectable "signal events" identified by a system according to the invention. It should be noted that a neurological event may be associated with a single signal event, or may be made up of a pattern or sequence of signal events identified in one or more locations, either concurrently or at different times. A "system event" as the term is used herein refers to either a detected signal event or some other event of interest either identified or generated by a system according to the invention, such as a timer expiration or other interrupt; it may be clinical or non-clinical in nature.

In general, a finite state machine is represented as and its behavior is described by a directed graph called a state transition diagram (or simply a state diagram) wherein a node or vertex of the graph (shown as a circle in FIG. 1) corresponds to a state of the finite state machine and wherein a path between two nodes (shown as an arrow between two circles in FIG. 1) corresponds to a transition from one state to another. The directed graph representation of a finite state machine provides an easy way to visualize the operation of the finite state machine and, thereby, the behavior of the corresponding system.

Referring initially to FIG. 1, a state transition diagram representing an exemplary time-independent state machine 110 is set forth; such a state machine is capable of being represented by a system according to the invention, and may represent several sequences of conditions that may be of interest for detecting neurological events.

In particular, hypothetically, if a neurological event of interest is defined by a sequence of signal events, namely a "signal A" followed by a "signal B" followed by a "signal C," or alternatively by signal A followed by a "signal D" followed by a "signal E," but never includes signal A directly followed by a "signal F," then the state machine of FIG. 1 represents the conditions leading up to the neurological event.

In particular, starting with an initial state 112, if signal A 114 is encountered, the state machine moves to a first state 116. All of the combinations described above begin with signal A 114. If signal A 114 is followed by signal B 118, then a second state 120 is achieved, and if signal C 122 is then observed, then a detection state 124 is reached, and a system according to the invention reacts accordingly. After the system acts as desired, the state machine 110 generally will be reset to the initial state 112 for further use.

After the first state 116 is reached, if signal D 126 is observed instead of signal B 118, then the state machine transitions to a third state 128. Following that, observation of signal E 130 will cause the detection state 124 to be reached, as above. Accordingly, two possible sequences of signal events lead to the detection state 124: signal A 114, then signal B 118, then signal C 122 ("A>B>C"); or alternatively, signal A 114, then signal D 126, then signal E 130 ("A>D>E").

On the other hand, if after the first state 116 is reached, signal F 132 is encountered, then the state machine transitions to an end state 134, and a system according to the invention performs any desired action (which may include resetting the state machine 110 to the initial state 112, either immediately or after a delay or some other action).

Figure 2:
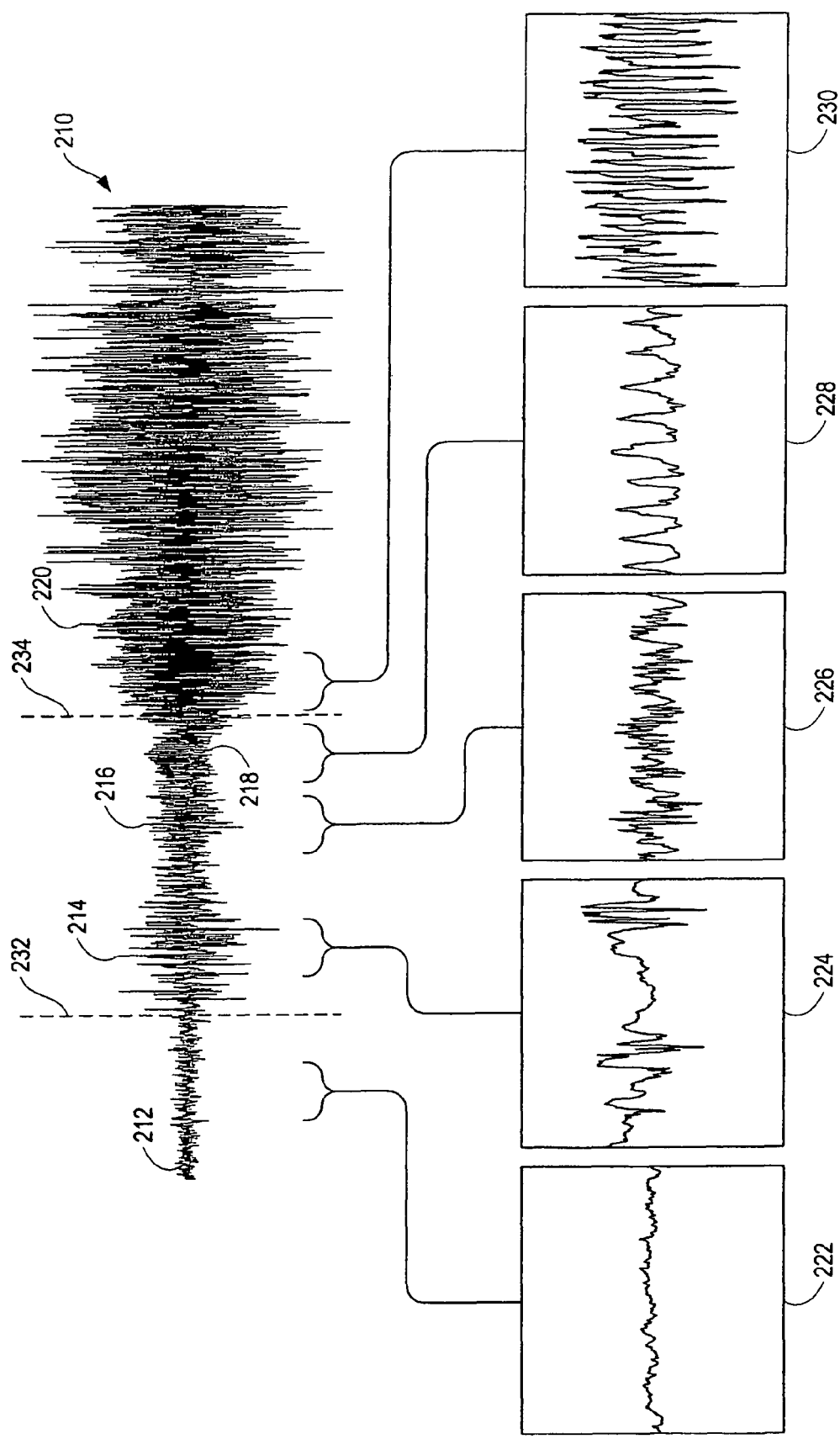
FIG. 2 is an exemplary electrographic waveform including a sequence of several signal types adapted for detection with a system according to the invention.

FIG. 2 sets forth an exemplary electrographic waveform 210; it is illustrative of how sequence detection according to the invention is advantageous.

The exemplary electrographic waveform 210 includes several different types of activity: initially, background activity 212 generally representing normal brain activity; an initial higher-energy burst 214 including spike-and-wave activity; a lower-amplitude high-frequency portion 216 followed immediately by a lower-frequency rhythmic segment 218; all of which is then followed by stereotypical high-amplitude higher-frequency seizure activity 220.

It will be observed that the background activity 212, when magnified (primarily along the x-axis), is a relatively low-amplitude signal 222 with little or no observable organization. Accordingly, detection tools described in detail below (and in U.S. patent application Ser. No. 09/896,092, filed on Jun. 28, 2001, incorporated by reference below) are generally able to distinguish background activity 212 from the other types of activity described below and also illustrated in FIG. 2, as well as other types of signals.

The initial higher-energy burst 214 that follows the background activity 212 appears, when magnified, to include prominent spike-and-wave activity 224 that is detectable by a system according to the invention as set forth in detail below. Similarly, the following lower-amplitude high-frequency portion 216 (which when magnified shows distinctive high-frequency activity 226) also has detectable characteristics, as does the lower-frequency rhythmic segment 218 (which, when magnified, clearly shows primarily low-frequency content 228).

After the seizure activity 220 begins, a magnified portion of the waveform illustrates higher-frequency high-amplitude activity 230; at this point, clinical symptoms are likely to be imminent.

Preferably, a system according to the invention is able to identify the seizure activity 220 at an early point in time 232, immediately after the background activity 212 gives way to something else (in this case, a higher-energy spike-and-wave burst 214). If the spike-and-wave burst 214 is always followed closely by seizure activity 220 (regardless of what comes between), then the early point in time 232 can be considered an unequivocal electrographic onset (UEO), and it would be sufficient to detect only the distinction between the background activity and the spike-and-wave burst 214.

However, if signals similar to the spike-and-wave burst 214 occur at other times as well, and are not followed closely by seizure activity 220, then the spike-and-wave burst 214 may not be an adequate indicator of imminent seizure. It may, in this circumstance, be necessary to detect part or all of the sequence of signals 212-220 illustrated in FIG. 2, and detection may be accomplished at a later point in time 234, preferably still before clinical symptoms begin.

Accordingly, the sequence of signals illustrated in FIG. 2 is relatively complex, and it is expected that in actual real-world implementations of a system according to the invention, neurological event detection and prediction can be accomplished with fewer states and less complexity. However, as will be appreciated in light of the detailed description below, the invention described herein is sufficiently flexible to accommodate even more complex situations.

There is no relationship between the illustrative state machine transition diagram of FIG. 1 and the waveforms of FIG. 2, that is, the state machine set forth in FIG. 1 does not necessarily represent any aspect of FIG. 2. However, an analogy can be made to the terminology of the exemplary state machine of FIG. 1. In particular, four different "signal events" (i.e., different identified signal types) illustrated in FIG. 2 would trigger transitions between states after the initial state. While only background activity 212 is present, the state machine would remain in its initial state. Upon detection of the spike-and-wave burst 214 ("signal A"), the state machine would transition to a first state. Upon detection of the lower-amplitude high-frequency portion 216 ("signal B"), the state machine would transition to a second state. With observation of the lower-frequency rhythmic segment 218 ("signal C"), the state machine would transition to a third state. Seizure activity 220 ("signal D") would then prompt transition to a detection state, at which point therapy would be applied (or other desired action taken). It is important to note that, as described above, the entire sequence of signals must occur, or a detection will not be triggered. If high-amplitude activity similar to the seizure activity 220 is occasionally present without a seizure occurring, the sequence identification facilitated by the invention will tend to reduce false positive detections, and hence undesired therapy applications, as will be described in further detail below.

Figure 3:
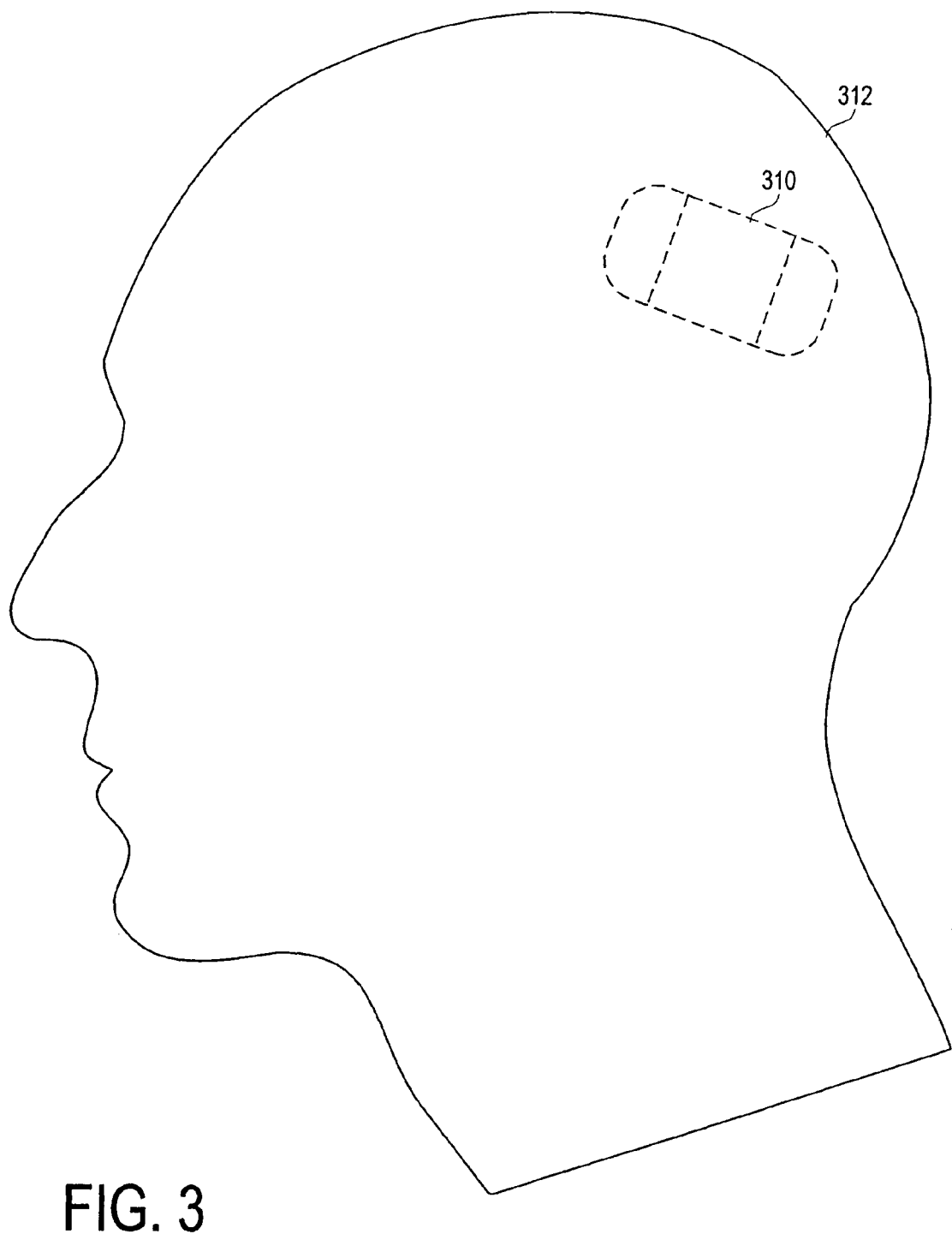
FIG. 3 is a schematic illustration of a patient's head showing the placement of an implantable neurostimulator according to an embodiment of the invention.

FIG. 3 depicts an intracranially implanted device 310 according to the invention, which in one embodiment is a small self-contained responsive neurostimulator. As the term is used herein, a responsive neurostimulator is a device capable of detecting or predicting ictal activity (or other neurological events) and providing electrical stimulation to neural tissue in response to that activity, where the electrical stimulation is specifically intended to terminate the ictal activity, treat a neurological event, prevent an unwanted neurological event from occurring, or lessen the severity or frequency of certain symptoms of a neurological disorder. As disclosed herein, the responsive neurostimulator detects ictal activity by systems and methods according to the invention.

Preferably, an implantable device according to the invention is capable of detecting or predicting any kind of neurological event that has a representative electrographic signature. While the disclosed embodiment is described primarily as responsive to epileptic seizures, it should be recognized that it is also possible to respond to other types of neurological disorders, such as movement disorders (e.g. the tremors characterizing Parkinson's disease), migraine headaches, chronic pain, and neuropsychiatric disorders such as depression. Preferably, neurological events representing any or all of these afflictions can be detected when they are actually occurring, in an onset stage, or as a predictive precursor before clinical symptoms begin.

Figure 4:
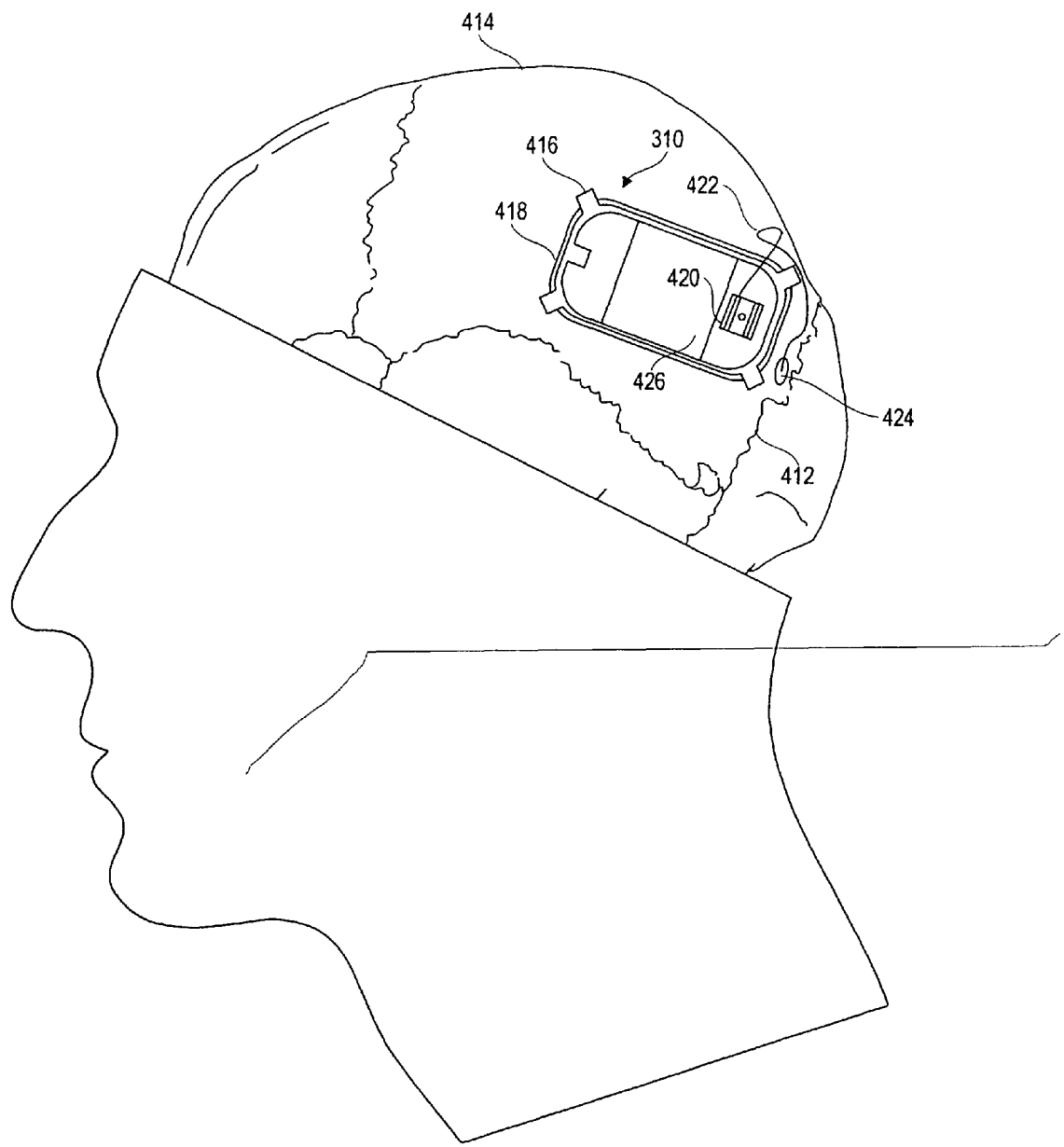
FIG. 4 is a schematic illustration of a patient's cranium showing the implantable neurostimulator of FIG. 3 as implanted, including leads extending to the patient's brain.

In the disclosed embodiment, the neurostimulator is implanted intracranially in a patient's parietal bone 410, in a location anterior to the lambdoidal suture 412 (see FIG. 4). It should be noted, however, that the placement described and illustrated herein is merely exemplary, and other locations and configurations are also possible, in the cranium or elsewhere, depending on the size and shape of the device and individual patient needs, among other factors. The device 310 is preferably configured to fit the contours of the patient's cranium 414. In an alternative embodiment, the device 310 is implanted under the patient's scalp 312 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 310 described and illustrated herein is preferably a responsive neurostimulator for detecting and treating epilepsy by detecting seizures or their onsets or precursors, and preventing and/or terminating such epileptic seizures.

In an alternative embodiment of the invention, the device 310 is not a responsive neurostimulator, but is an apparatus capable of detecting neurological conditions and events and performing actions in response thereto. The actions performed by such an embodiment of the device 310 need not be therapeutic, but may involve data recording or transmission, providing warnings to the patient, or any of a number of known alternative actions. Such a device will typically act as a diagnostic device when interfaced with external equipment, as will be discussed in further detail below.

The device 310, as implanted intracranially, is illustrated in greater detail in FIG. 4. The device 310 is affixed in the patient's cranium 414 by way of a ferrule 416. The ferrule 416 is a structural member adapted to fit into a cranial opening, attach to the cranium 414, and retain the device 310.

To implant the device 310, a craniotomy is performed in the parietal bone 410 anterior to the lambdoidal suture 412 to define an opening 418 slightly larger than the device 310. The ferrule 416 is inserted into the opening 418 and affixed to the cranium 414, ensuring a tight and secure fit. The device 310 is then inserted into and affixed to the ferrule 416.

As shown in FIG. 4, the device 310 includes a lead connector 420 adapted to receive one or more electrical leads, such as a first lead 422. The lead connector 420 acts to physically secure the lead 422 to the device 310, and facilitates electrical connection between a conductor in the lead 422 coupling an electrode to circuitry within the device 310. The lead connector 420 accomplishes this in a substantially fluid-tight environment with biocompatible materials.

The lead 422, as illustrated, and other leads for use in a system or method according to the invention, is a flexible elongated member having one or more conductors. As shown, the lead 422 is coupled to the device 310 via the lead connector 420, and is generally situated on the outer surface of the cranium 414 (and under the patient's scalp 312), extending between the device 310 and a burr hole 424 or other cranial opening, where the lead 422 enters the cranium 414 and is coupled to a depth electrode (e.g., one of the electrodes 512-518 of FIG. 5) implanted in a desired location in the patient's brain. If the length of the lead 422 is substantially greater than the distance between the device 310 and the burr hole 424, any excess may be urged into a coil configuration under the scalp 312. As described in U.S. Pat. No. 6,006,124 to Fischell, et al., which is hereby incorporated by reference as though set forth in full herein, the burr hole 424 is sealed after implantation to prevent further movement of the lead 422; in an embodiment of the invention, a burr hole cover apparatus is affixed to the cranium 414 at least partially within the burr hole 424 to provide this functionality.

The device 310 includes a durable outer housing 426 fabricated from a biocompatible material. Titanium, which is light, extremely strong, and biocompatible, is used in analogous devices, such as cardiac pacemakers, and would serve advantageously in this context. As the device 310 is self-contained, the housing 426 encloses a battery and any electronic circuitry necessary or desirable to provide the functionality described herein, as well as any other features. As will be described in further detail below, a telemetry coil may be provided outside of the housing 426 (and potentially integrated with the lead connector 420) to facilitate communication between the device 310 and external devices.

The neurostimulator configuration described herein and illustrated in FIG. 4 provides several advantages over alternative designs. First, the self-contained nature of the neurostimulator substantially decreases the need for access to the device 310, allowing the patient to participate in normal life activities. Its small size and intracranial placement causes a minimum of cosmetic disfigurement. The device 310 will fit in an opening in the patient's cranium, under the patient's scalp, with little noticeable protrusion or bulge. The ferrule 416 used for implantation allows the craniotomy to be performed and fit verified without the possibility of breaking the device 310, and also provides protection against the device 310 being pushed into the brain under external pressure or impact. A further advantage is that the ferrule 416 receives any cranial bone growth, so at explant, the device 310 can be replaced without removing any bone screws—only the fasteners retaining the device 310 in the ferrule 416 need be manipulated.

Figure 5:
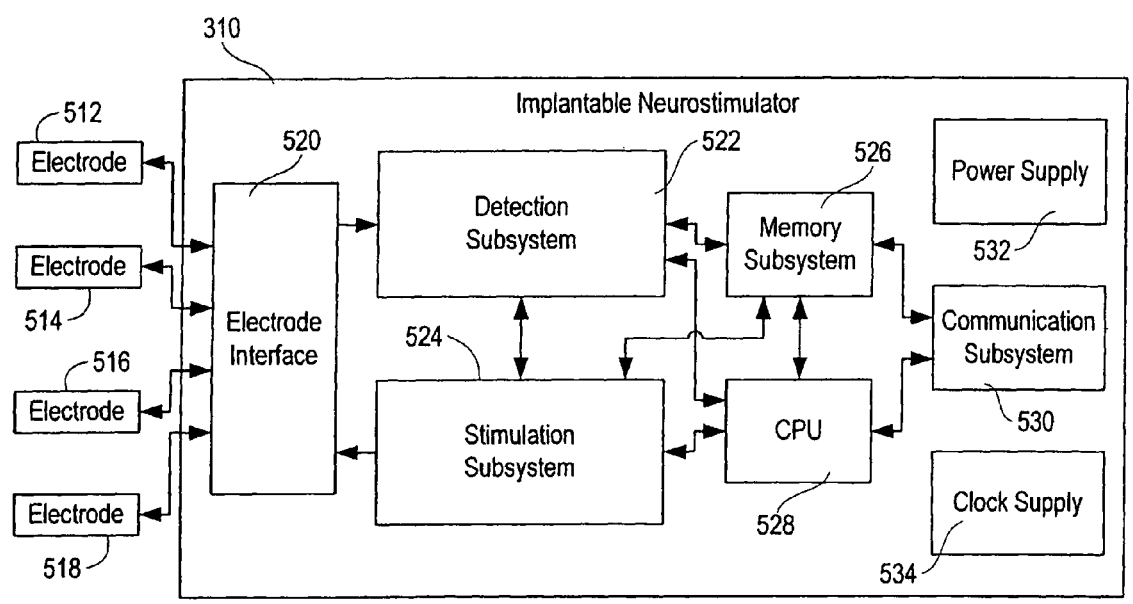
FIG. 5 is a block diagram illustrating the major functional subsystems of an implantable neurostimulator according to the invention.

FIG. 5 depicts a schematic block diagram of a neurostimulator system according to the invention, including the implantable neurostimulator device 310, which in one embodiment (as described above) is a small self-contained responsive neurostimulator that is intracranially implanted. As the term is used herein, a responsive neurostimulator is a device capable of detecting undesired activity (or other neurological events) and providing electrical stimulation to neural tissue in response to that activity, where the electrical stimulation is specifically intended to terminate the undesired activity, treat a neurological event, prevent an unwanted neurological event from occurring, or lessen the severity or frequency of certain symptoms of a neurological disorder.

It should be recognized that the embodiment of the device described and illustrated herein is preferably a responsive neurostimulator for detecting and treating epilepsy by detecting seizure precursors and preventing and/or terminating epileptic seizures.

FIG. 5 is an overall block diagram of the implantable neurostimulator device 310 used for measurement, detection, and treatment according to the invention. Inside the housing of the neurostimulator device 310 are several subsystems making up the device. The implantable neurostimulator device 310 is capable of being coupled to a plurality of electrodes 512, 514, 516, and 518 (each of which may be individually or together connected to the implantable neurostimulator device 310 via one or more leads) for sensing and stimulation. In the illustrated embodiment, the coupling is accomplished through a lead connector. Although four electrodes are shown in FIG. 5, it should be recognized that any number is possible, and in the embodiment described in detail below, eight electrodes are used. In fact, it is possible to employ an embodiment of the invention that uses a single lead with at least two electrodes, or two leads each with a single electrode (or with a second electrode provided by a conductive exterior portion of the housing in one embodiment), although bipolar sensing between two closely spaced electrodes on a lead is preferred to minimize common mode signals including noise.

The electrodes 512-518 are in contact with the patient's brain or are otherwise advantageously located to receive EEG signals or provide electrical stimulation. Each of the electrodes 512-518 is also electrically coupled to an electrode interface 520. Preferably, the electrode interface is capable of selecting each electrode as required for sensing and stimulation; accordingly the electrode interface is coupled to a detection subsystem 522 and a stimulation subsystem 524 (which, in an embodiment of the invention, may provide therapy other than electrical stimulation). The electrode interface may also provide any other features, capabilities, or aspects, including but not limited to amplification, isolation, and charge-balancing functions, that are required for a proper interface with neurological tissue and not provided by any other subsystem of the device 310.

The detection subsystem 522 includes and serves primarily as an EEG waveform analyzer; detection is accomplished in conjunction with a central processing unit (CPU) 528. The EEG waveform analyzer function is adapted to receive EEG signals from the electrodes 512-518, through the electrode interface 520, and to process those EEG signals to identify neurological activity indicative of a seizure or a precursor to a seizure. One way to implement such EEG analysis functionality is disclosed in detail in U.S. Pat. No. 6,016,449 to Fischell et al., incorporated by reference above. Additional inventive methods are described in U.S. patent application Ser. No. 09/896,092 to Pless et al., filed on Jun. 28, 2001 and entitled "SEIZURE SENSING AND DETECTION USING AN IMPLANTABLE DEVICE," of which details will be set forth below (and which is also hereby incorporated by reference as though set forth in full). The detection subsystem may optionally also contain further sensing and detection capabilities, including but not limited to parameters derived from other physiological conditions (such as electrophysiological parameters, temperature, blood pressure, etc.). In general, prior to analysis, the detection subsystem performs amplification, analog to digital conversion, and multiplexing functions on the signals in the sensing channels received from the electrodes 512-518.

The stimulation subsystem 524 is capable of applying electrical stimulation to neurological tissue through the electrodes 512-518. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal neurological events detected by the EEG analyzer function of the detection subsystem 522. As illustrated in FIG. 5, the stimulation subsystem 524 and the EEG analyzer function of the detection subsystem 522 are in communication; this facilitates the ability of stimulation subsystem 524 to provide responsive stimulation as well as an ability of the detection subsystem 522 to blank the amplifiers while stimulation is being performed to minimize stimulation artifacts. It is contemplated that the parameters of the stimulation signal (e.g., frequency, duration, waveform) provided by the stimulation subsystem 524 would be specified by other subsystems in the implantable device 310, as will be described in further detail below.

In accordance with the invention, the stimulation subsystem 524 may also provide for other types of stimulation, besides electrical stimulation described above. In particular, in certain circumstances, it may be advantageous to provide audio, visual, or tactile signals to the patient, to provide somatosensory electrical stimulation to locations other than the brain, or to deliver a drug or other therapeutic agent (either alone or in conjunction with stimulation).

Also in the implantable neurostimulator device 310 is a memory subsystem 526 and the CPU 528, which can take the form of a microcontroller. The memory subsystem is coupled to the detection subsystem 522 (e.g., for receiving and storing data representative of sensed EEG signals and evoked responses), the stimulation subsystem 524 (e.g., for providing stimulation waveform parameters to the stimulation subsystem), and the CPU 528, which can control the operation of (and store and retrieve data from) the memory subsystem 526. In addition to the memory subsystem 526, the CPU 528 is also connected to the detection subsystem 522 and the stimulation subsystem 524 for direct control of those subsystems.

Also provided in the implantable neurostimulator device 310, and coupled to the memory subsystem 526 and the CPU 528, is a communication subsystem 530. The communication subsystem 530 enables communication between the device 310 and the outside world, particularly an external programmer and a patient initiating device, both of which will be described below with reference to FIG. 6. As set forth above, the disclosed embodiment of the communication subsystem 530 includes a telemetry coil (which may be situated outside of the housing of the implantable neurostimulator device 310) enabling transmission and reception of signals, to or from an external apparatus, via inductive coupling. Alternative embodiments of the communication subsystem 530 could use an antenna for an RF link or an audio transducer for an audio link. Preferably, the communication subsystem 530 also includes a GMR (giant magnetoresistive effect) sensor to enable receiving simple signals (namely the placement and removal of a magnet) from a patient initiating device; this capability can be used to initiate EEG recording as will be described in further detail below.

If the stimulation subsystem 524 includes the audio capability set forth above, it may be advantageous for the communication subsystem 530 to cause the audio signal to be generated by the stimulation subsystem 524 upon receipt of an appropriate indication from the patient initiating device (e.g., the magnet used to communicate with the GMR sensor of the communication subsystem 530), thereby confirming to the patient or caregiver that a desired action will be performed, e.g. that an EEG record will be stored.

Rounding out the subsystems in the implantable neurostimulator device 310 are a power supply 532 and a clock supply 534. The power supply 532 supplies the voltages and currents necessary for each of the other subsystems. The clock supply 534 supplies substantially all of the other subsystems with any clock and timing signals necessary for their operation, including a real-time clock signal to coordinate programmed and scheduled actions and the timer functionality used by the detection subsystem 522 that is described in detail below.

It should be observed that while the memory subsystem 526 is illustrated in FIG. 5 as a separate functional subsystem, the other subsystems may also require various amounts of memory to perform the functions described above and others. Furthermore, while the implantable neurostimulator device 310 is preferably a single physical unit (i.e., a control module) contained within a single implantable physical enclosure, namely the housing described above, other embodiments of the invention might be configured differently. The neurostimulator 310 may be provided as an external unit not adapted for implantation, or it may comprise a plurality of spatially separate units each performing a subset of the capabilities described above, some or all of which might be external devices not suitable for implantation. Also, it should be noted that the various functions and capabilities of the subsystems described above may be performed by electronic hardware, computer software (or firmware), or a combination thereof. The division of work between the CPU 528 and the other functional subsystems may also vary—the functional distinctions illustrated in FIG. 5 may not reflect the partitioning and integration of functions in a real-world system or method according to the invention.

Figure 6:
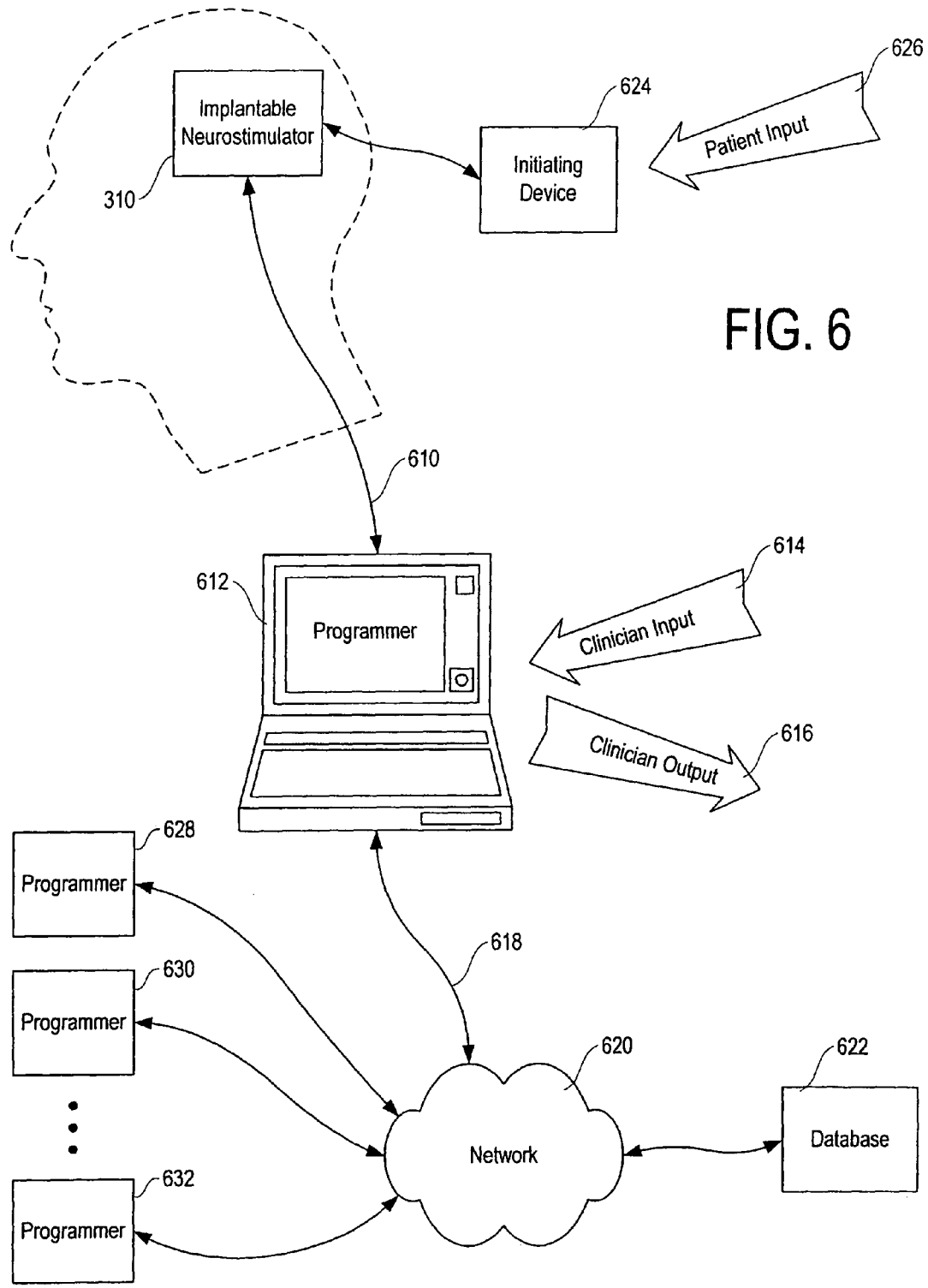
FIG. 6 is a block diagram illustrating a system context in which an implantable neurostimulator according to the invention is implanted and operated.

As stated above, and as illustrated in FIG. 6, a neurostimulator according to the invention operates in conjunction with external equipment. The implantable neurostimulator device 310 is mostly autonomous (particularly when performing its usual sensing, detection, and stimulation capabilities), but preferably includes a selectable part-time wireless link 610 to external equipment such as a programmer 612. In the disclosed embodiment of the invention, the wireless link 610 is established by moving a wand (or other apparatus) having communication capabilities and coupled to the programmer 612 into communication range of the implantable neurostimulator device 310. The programmer 612 can then be used to manually control the operation of the device, as well as to transmit information to or receive information from the implantable neurostimulator 310. Several specific capabilities and operations performed by the programmer 612 in conjunction with the device will be described in further detail below.

The programmer 612 is capable of performing a number of advantageous operations in connection with the invention. In particular, the programmer 612 is able to specify and set variable parameters in the implantable neurostimulator device 310 to adapt the function of the device to meet the patient's needs, upload or receive data (including but not limited to stored EEG waveforms, parameters, or logs of actions taken) from the implantable neurostimulator 310 to the programmer 612, download or transmit program code and other information from the programmer 612 to the implantable neurostimulator 310, or command the implantable neurostimulator 310 to perform specific actions or change modes as desired by a physician operating the programmer 612. To facilitate these functions, the programmer 612 is adapted to receive clinician input 614 and provide clinician output 616; data is transmitted between the programmer 612 and the implantable neurostimulator 310 over the wireless link 610.

The programmer 612 may be used at a location remote from the implantable neurostimulator 310 if the wireless link 610 is enabled to transmit data over long distances. For example, the wireless link 610 may be established by a short-distance first link between the implantable neurostimulator 310 and a transceiver, with the transceiver enabled to relay communications over long distances to a remote programmer 612, either wirelessly (for example, over a wireless computer network) or via a wired communications link (such as a telephonic circuit or a computer network).

The programmer 612 may also be coupled via a communication link 618 to a network 620 such as the Internet. This allows any information uploaded from the implantable neurostimulator 310, as well as any program code or other information to be downloaded to the implantable neurostimulator 310, to be stored in a database 622 at one or more data repository locations (which may include various servers and network-connected programmers like the programmer 612). This would allow a patient (and the patient's physician) to have access to important data, including past treatment information and software updates, essentially anywhere in the world where there is a programmer (like the programmer 612) and a network connection. Alternatively, the programmer 612 may be connected to the database 622 over a trans-telephonic link.

In yet another alternative embodiment of the invention, the wireless link 610 from the implantable neurostimulator 310 may enable a transfer of data from the neurostimulator 310 to the database 622 without any involvement by the programmer 612. In this embodiment, as with others, the wireless link 610 may be established by a short-distance first link between the implantable neurostimulator 310 and a transceiver, with the transceiver enabled to relay communications over long distances to the database 622, either wirelessly (for example, over a wireless computer network) or via a wired communications link (such as trans-telephonically over a telephonic circuit, or over a computer network).

In the disclosed embodiment, the implantable neurostimulator 310 is also adapted to receive communications from an initiating device 624, typically controlled by the patient or a caregiver. Accordingly, patient input 626 from the initiating device 624 is transmitted over a wireless link to the implantable neurostimulator 310; such patient input 626 may be used to cause the implantable neurostimulator 310 to switch modes (on to off and vice versa, for example) or perform an action (e.g., store a record of EEG data). Preferably, the initiating device 624 is able to communicate with the implantable neurostimulator 310 through the communication subsystem 530 (FIG. 5), and possibly in the same manner the programmer 612 does. The link may be unidirectional (as with the magnet and GMR sensor described above), allowing commands to be passed in a single direction from the initiating device 624 to the implantable neurostimulator 310, but in an alternative embodiment of the invention is bi-directional, allowing status and data to be passed back to the initiating device 624. Accordingly, the initiating device 624 may be a programmable PDA or other hand-held computing device, such as a Palm Pilot® or PocketPC®. However, a simple form of initiating device 624 may take the form of a permanent magnet, if the communication subsystem 530 is adapted to identify magnetic fields and interruptions therein as communication signals.

The implantable neurostimulator 310 (FIG. 3) generally interacts with the programmer 612 (FIG. 6) as described below. Data stored in the memory subsystem 526 can be retrieved by the patient's physician through the wireless communication link 610, which operates through the communication subsystem 530 of the implantable neurostimulator 310. In connection with the invention, a software operating program run by the programmer 612 allows the physician to read out a history of neurological events detected including EEG information before, during, and after each neurological event, as well as specific information relating to the detection of each neurological event (such as, in one embodiment, the time-evolving energy spectrum of the patient's EEG). The programmer 612 also allows the physician to specify or alter any programmable parameters of the implantable neurostimulator 310. The software operating program also includes tools for the analysis and processing of recorded EEG records to assist the physician in developing optimized seizure detection parameters for each specific patient.

In an embodiment of the invention, the programmer 612 is primarily a commercially available PC, laptop computer, or workstation having a CPU, keyboard, mouse and display, and running a standard operating system such as Microsoft Windows®, Linux®, Unix®, or Apple Mac OS®. It is also envisioned that a dedicated programmer apparatus with a custom software package (which may not use a standard operating system) could be developed.

When running the computer workstation software operating program, the programmer 612 can process, store, play back and display on the display the patient's EEG signals, as previously stored by the implantable neurostimulator 310 of the implantable neurostimulator device.

The computer workstation software operating program also has the capability to simulate the detection and prediction of epileptiform activity. Furthermore, the software operating program of the present invention has the capability to allow a clinician to create or modify a patient-specific collection of information comprising, in one embodiment, algorithms and algorithm parameters for epileptiform activity detection. The patient-specific collection of detection algorithms and parameters used for neurological activity detection according to the invention will be referred to herein as a detection template or patient-specific template. The patient-specific template, in conjunction with other information and parameters generally transferred from the programmer to the implanted device (such as stimulation parameters, time schedules, and other patient-specific information), make up a set of operational parameters for the neurostimulator.

Following the development of a patient specific template on the programmer 612, the patient-specific template would be downloaded through the communications link 610 from the programmer 612 to the implantable neurostimulator 310.

The patient-specific template is used by the detection subsystem 522 and the CPU 528 of the implantable neurostimulator 310 to detect epileptiform activity in the patient's EEG signals, which can be programmed by a clinician to result in responsive stimulation of the patient's brain, as well as the storage of EEG records before and after the detection, facilitating later clinician review.

Preferably, the database 622 is adapted to communicate over the network 620 with multiple programmers, including the programmer 612 and additional programmers 628, 630, and 632. It is contemplated that programmers will be located at various medical facilities and physicians' offices at widely distributed locations. Accordingly, if more than one programmer has been used to upload EEG records from a patient's implantable neurostimulator 310, the EEG records will be aggregated via the database 622 and available thereafter to any of the programmers connected to the network 620, including the programmer 612.

Figure 7:
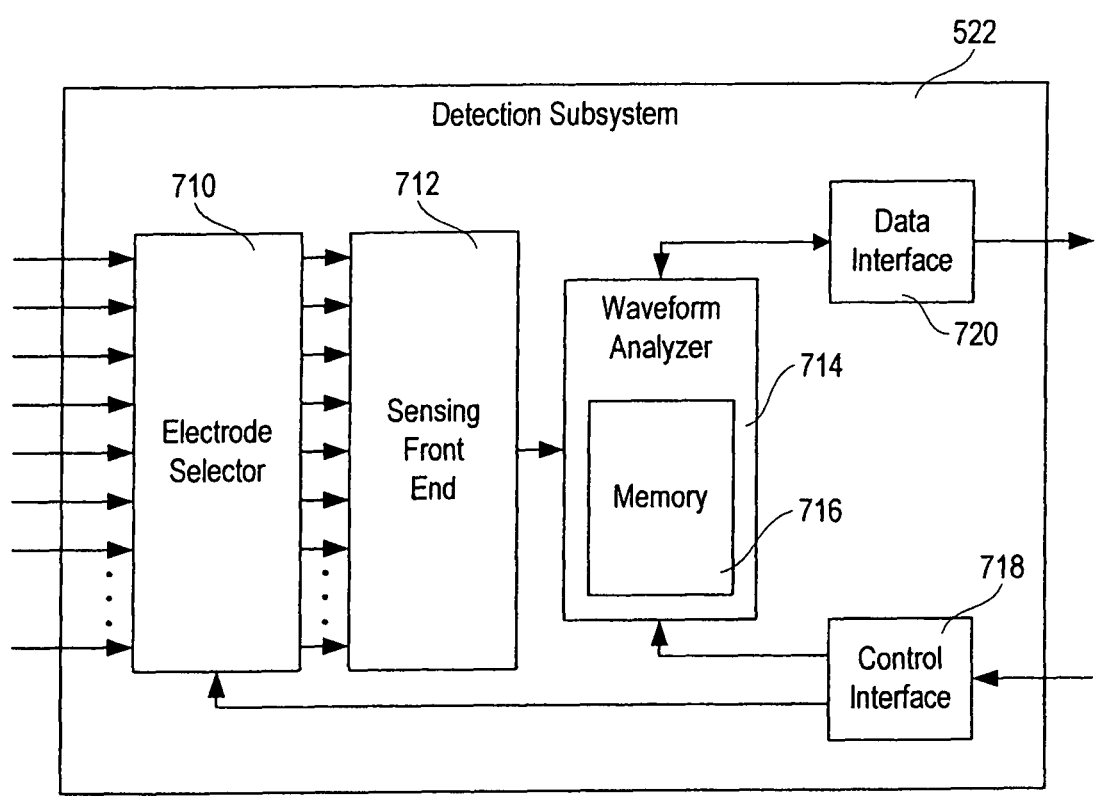
FIG. 7 is a block diagram illustrating the functional components of the detection subsystem of the implantable neurostimulator shown in FIG. 6.

FIG. 7 illustrates details of the detection subsystem 722 (FIG. 7). Inputs from the electrodes 412-418 are on the left, and connections to other subsystems are on the right.

Signals received from the electrodes 512-518 (as routed through the electrode interface 520) are received in an electrode selector 710. The electrode selector 710 allows the device to select which electrodes (of the electrodes 512-518) should be routed to which individual sensing channels of the detection subsystem 522, based on commands received through a control interface 718 from the memory subsystem 526 or the CPU 528 (FIG. 5). Preferably, each sensing channel of the detection subsystem 522 receives a bipolar signal representative of the difference in electrical potential between two selectable electrodes. Accordingly, the electrode selector 710 provides signals corresponding to each pair of selected electrodes (of the electrodes 512-518) to a sensing front end 712, which performs amplification, analog to digital conversion, and multiplexing functions on the signals in the sensing channels. The sensing front end will be described further below in connection with FIG. 8.

A multiplexed input signal representative of all active sensing channels is then fed from the sensing front end 712 to a waveform analyzer 714. The waveform analyzer 714 is preferably a special-purpose digital signal processor (DSP) adapted for use with the invention, or in an alternative embodiment, may comprise a programmable general-purpose DSP. In the disclosed embodiment, the waveform analyzer has its own scratchpad memory area 716 used for local storage of data and program variables when the signal processing is being performed. In either case, the signal processor performs suitable measurement and detection methods described generally above and in greater detail below. Any results from such methods, as well as any digitized signals intended for storage transmission to external equipment, are passed to various other subsystems of the device 310, including the memory subsystem 526 and the CPU 528 (FIG. 5) through a data interface 720. Similarly, the control interface 718 allows the waveform analyzer 714 and the electrode selector 710 to be in communication with the CPU 528.

Figure 8:
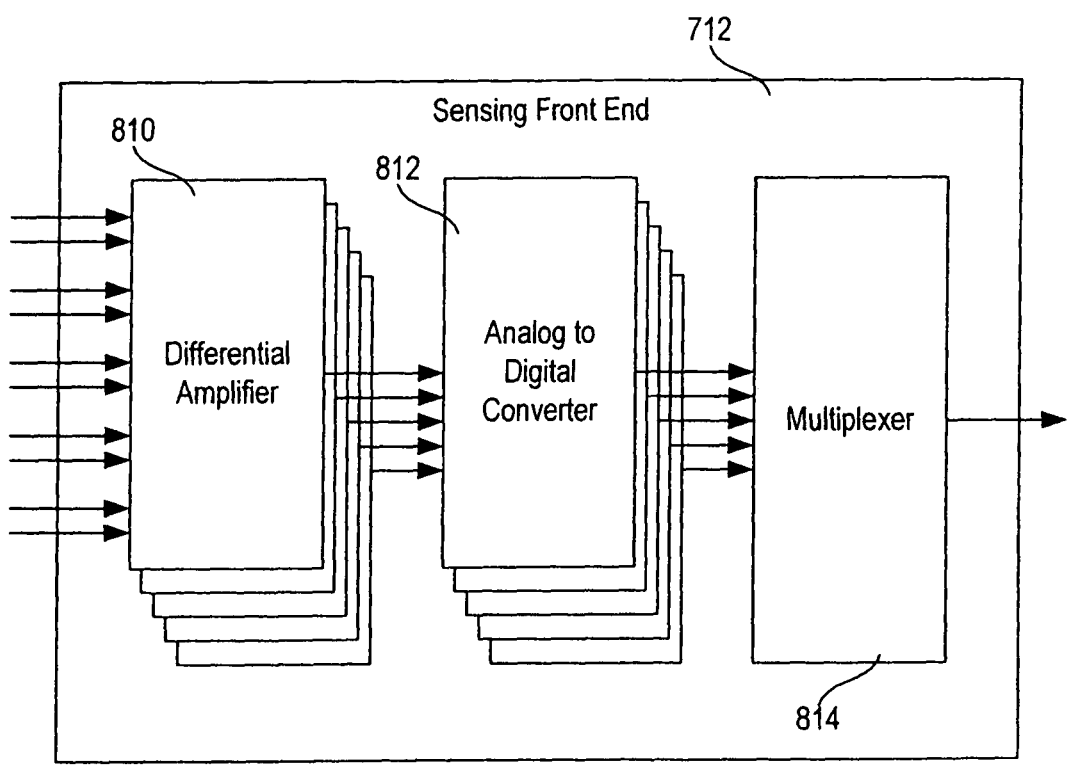
FIG. 8 is a block diagram illustrating the functional components of the sensing front end of the detection subsystem of FIG. 7.

Referring now to FIG. 8, the sensing front end 712 (FIG. 7) is illustrated in further detail. As shown, the sensing front end includes a plurality of differential amplifier channels 810, each of which receives a selected pair of inputs from the electrode selector 710. In a preferred embodiment of the invention, each of differential amplifier channels 810 is adapted to receive or to share inputs with one or more other differential amplifier channels 810 without adversely affecting the sensing and detection capabilities of a system according to the invention. Specifically, in an embodiment of the invention, there are at least eight electrodes, which can be mapped separately to eight differential amplifier channels 810 representing eight different sensing channels and capable of individually processing eight bipolar signals, each of which represents an electrical potential difference between two monopolar input signals received from the electrodes and applied to the sensing channels via the electrode selector 710. For clarity, only five channels are illustrated in FIG. 8, but it should be noted that any practical number of sensing channels may be employed in a system according to the invention.

Each differential amplifier channel 810 feeds a corresponding analog to digital converter (ADC) 812. Preferably, the analog to digital converters 812 are separately programmable with respect to sample rates—in the disclosed embodiment, the ADCs 812 convert analog signals into 10-bit unsigned integer digital data streams at a sample rate selectable between 250 Hz and 500 Hz. In several of the illustrations described below where waveforms are shown, sample rates of 250 Hz are typically used for simplicity. However, the invention shall not be deemed to be so limited, and numerous sample rate and resolution options are possible, with tradeoffs known to individuals of ordinary skill in the art of electronic signal processing. The resulting digital signals are received by a multiplexer 814 that creates a single interleaved digital data stream representative of the data from all active sensing channels. As will be described in further detail below, not all of the sensing channels need to be used at one time, and it may in fact be advantageous in certain circumstances to deactivate certain sensing channels to reduce the power consumed by a system according to the invention.

It should be noted that as illustrated and described herein, a "sensing channel" is not necessarily a single physical or functional item that can be identified in any illustration. Rather, a sensing channel is formed from the functional sequence of operations described herein, and particularly represents a single electrical signal received from any pair or combination of electrodes, as preprocessed by a system according to the invention, in both analog and digital forms. See, e.g., U.S. patent application Ser. No. 09/517,797 to D. Fischell et al., filed on Mar. 2, 2000 and entitled "neurological Event Detection Using Processed Display Channel Based Algorithms and Devices Incorporating These Procedures," which is hereby incorporated by reference as though set forth in full herein. At times (particularly after the multiplexer 814), multiple sensing channels are processed by the same physical and functional components of the system; notwithstanding that, it should be recognized that unless the description herein indicates to the contrary, a system according to the invention processes, handles, and treats each sensing channel independently.

The interleaved digital data stream is passed from the multiplexer 814, out of the sensing front end 712, and into the waveform analyzer 714. The waveform analyzer 714 is illustrated in detail in FIG. 9.

The interleaved digital data stream representing information from all of the active sensing channels is first received by a channel controller 910. The channel controller applies information from the active sensing channels to a number of wave morphology analysis units 912 and window analysis units 914. It is preferred to have as many wave morphology analysis units 912 and window analysis units 914 as possible, consistent with the goals of efficiency, size, and low power consumption necessary for an implantable device. In a presently preferred embodiment of the invention, there are sixteen wave morphology analysis units 912 and eight window analysis units 914, each of which can receive data from any of the sensing channels of the sensing front end 712 (FIG. 7), and each of which can be operated with different and independent parameters, including differing sample rates, as will be discussed in further detail below.

Each of the wave morphology analysis units 912 operates to extract certain feature information from an input waveform as described below in conjunction with FIGS. 12-15. Similarly, each of the window analysis units 914 performs certain data reduction and signal analysis within time windows in the manner described in conjunction with FIGS. 16-21. Output data from the various wave morphology analysis units 912 and window analysis units 914 are combined via event detector logic 916. The event detector logic 916 and the channel controller 910 are controlled by control commands 918 received from the control interface 718 (FIG. 7).

A "detection channel," as the term is used herein, refers to a data stream including the active sensing front end 712 and the analysis units of the waveform analyzer 714 processing that data stream, in both analog and digital forms. It should be noted that each detection channel can receive data from a single sensing channel; each sensing channel preferably can be applied to the input of any combination of detection channels. The latter selection is accomplished by the channel controller 910. As with the sensing channels, not all detection channels need to be active; certain detection channels can be deactivated to save power or if additional detection processing is deemed unnecessary in certain applications.

In conjunction with the operation of the wave morphology analysis units 912 and the window analysis units 914, a scratchpad memory area 716 is provided for temporary storage of processed data. The scratchpad memory area 716 may be physically part of the memory subsystem 526 (FIG. 5), or alternatively may be provided for the exclusive use of the waveform analyzer 714 (FIG. 7). Other subsystems and components of a system according to the invention may also be furnished with local scratchpad memory, if such a configuration is advantageous.

Figure 10:
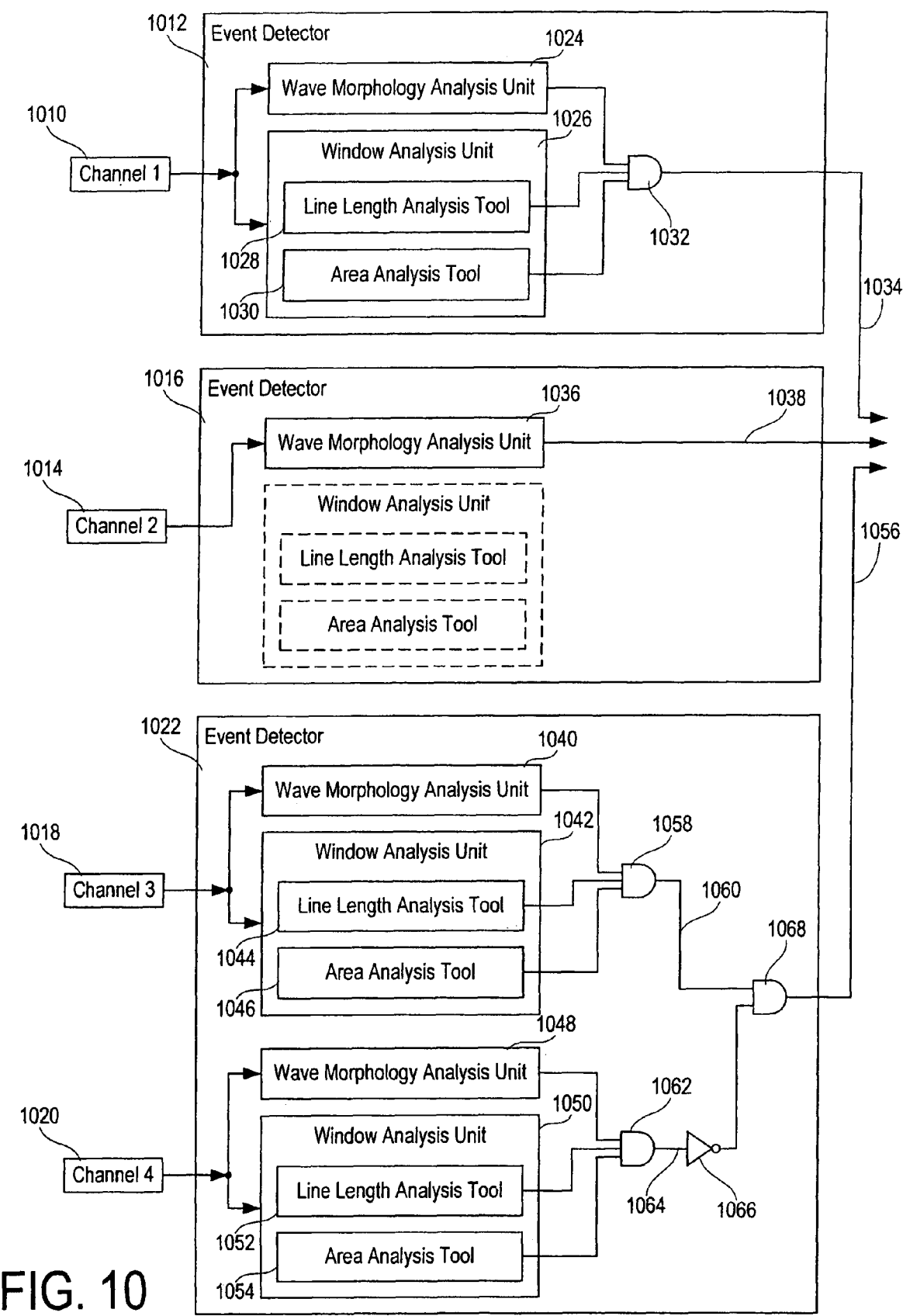
FIG. 10 is a block diagram illustrating the functional arrangement of components of the waveform analyzer of the detection subsystem of FIG. 7 in one possible programmed embodiment of the invention.

The operation of the event detector logic 916 is illustrated in detail in the functional block diagram of FIG. 10, in which four exemplary sensing channels are analyzed by three illustrative signal event detectors.

A first sensing channel 1010 provides input to a first event detector 1012. While the first event detector 1012 is illustrated as a functional block in the block diagram of FIG. 10, it should be recognized that it is a functional block only for purposes of illustration, and may not have any physical counterpart in a device according to the invention. Similarly, a second sensing channel 1014 provides input to a second event detector 1016, and a third input channel 1018 and a fourth input channel 1020 both provide input to a third event detector 1022.

Figure 9:
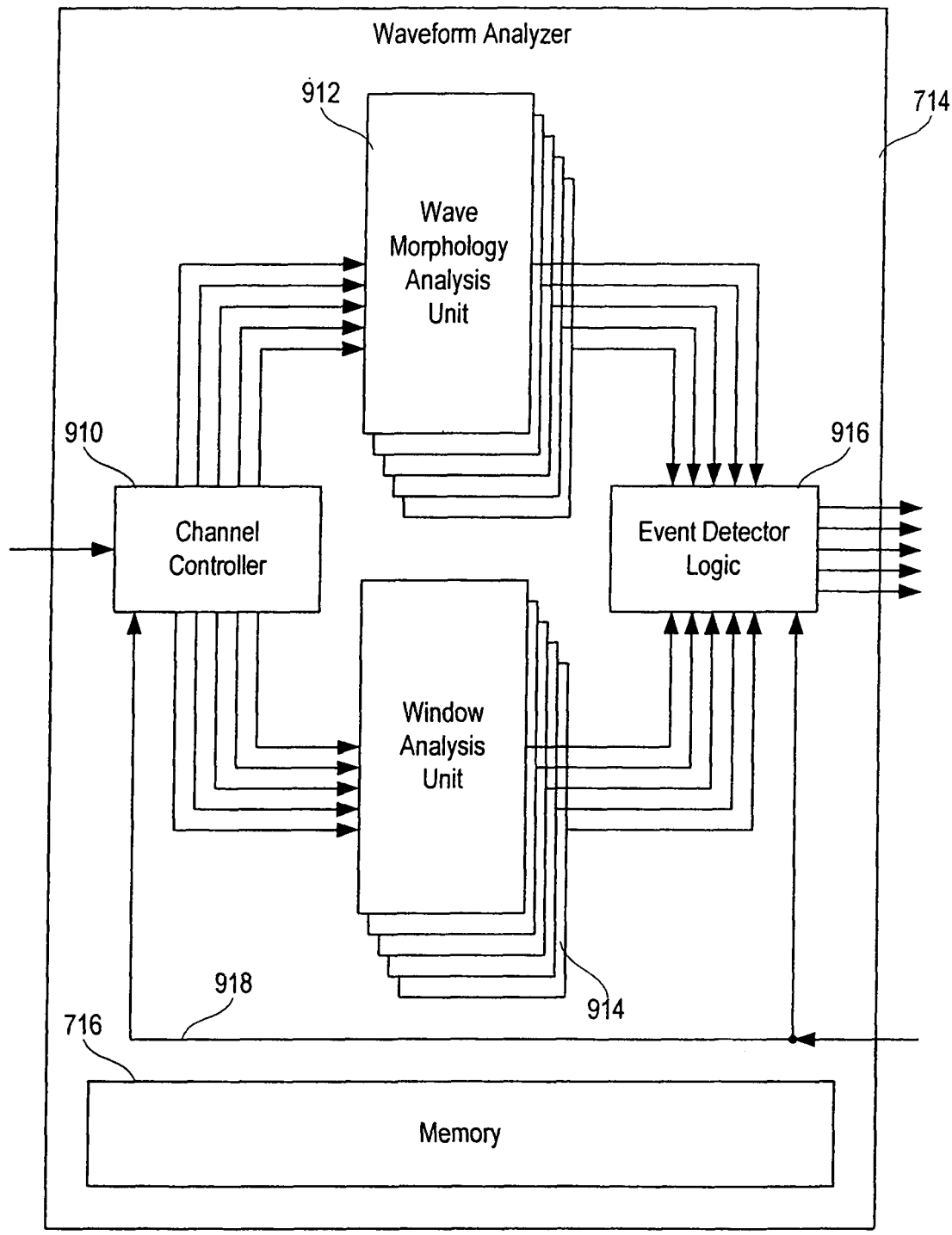
FIG. 9 is a block diagram illustrating the components of the waveform analyzer of the detection subsystem of FIG. 7.

Considering the processing performed by the event detectors 1012, 1016, and 1022, the first input channel 1010 feeds a signal to both a wave morphology analysis unit 1024 (one of the wave morphology analysis units 912 of FIG. 9) and a window analysis unit 1026 (one of the window analysis units 914 of FIG. 9). The window analysis unit 1026, in turn, includes a line length analysis tool 1028 and an area analysis tool 1030. As will be discussed in detail below, the line length analysis tool 1028 and the area analysis tool 1030 analyze different aspects of the signal from the first input channel 1010.

Outputs from the wave morphology analysis unit 1024, the line length analysis tool 1028, and the area analysis tool 1030 are combined in a Boolean AND operation 1032 and sent to an output 1034 for further use by a system according to the invention. For example, if a combination of analysis tools in an event detector identifies several simultaneous (or near-simultaneous) types of activity in an input channel, a system according to the invention may be programmed to perform an action in response thereto. Details of the analysis tools and the combination processes used in event detectors according to the invention will be set forth in greater detail below.

In the second event detector 1016, only a wave morphology analysis unit 1036 is active. Accordingly, no Boolean operation needs to be performed, and the wave morphology analysis unit 1036 directly feeds an event detector output 1038.

The third event detector 1022 operates on two input channels 1018 and 1020, and includes two separate detection channels of analysis units: a first wave morphology analysis unit 1040 and a first window analysis unit 1042, the latter including a first line length analysis tool 1044 and a first area analysis tool 1046; and a second wave morphology analysis unit 1048 and a second window analysis unit 1050, the latter including a second line length analysis tool 1052 and a second area analysis tool 1054. The two detection channels of analysis units are combined to provide a single event detector output 1056.

In the first detection channel of analysis units 1040 and 1042, outputs from the first wave morphology analysis unit 1040, the first line length analysis tool 1044, and the first area analysis tool 1046 are combined via a Boolean AND operation 1058 into a first detection channel output 1060. Similarly, in the second detection channel of analysis units 1048 and 1050, outputs from the second wave morphology analysis unit 1048, the second line length analysis tool 1052, and the second area analysis tool 1054 are combined via a Boolean AND operation 1062 into a second detection channel output

1064. In the illustrated embodiment of the invention, the second detection channel output 1064 is invertible with selectable Boolean logic inversion 1066 before it is combined with the first detection channel output 1060. Subsequently, the first detection channel output 1060 and the second detection channel output 1064 are combined with a Boolean AND operation 1068 to provide a signal to the output 1056. In an alternative embodiment, a Boolean OR operation is used to combine the first detection channel output 1060 and the second detection channel output 1064.

In one embodiment of the invention, the second detection channel (analysis units 1048 and 1050) represents a "qualifying channel" with respect to the first detection channel (analysis units 1040 and 1042). In general, a qualifying channel allows a detection to be made only when both channels are in concurrence with regard to detection of a signal event. For example, a qualifying channel can be used to indicate when a seizure has "generalized," i.e. spread through a significant portion of a patient's brain. To do this, the third input channel 1018 and the fourth input channel 1020 are configured to receive EEG waveforms from separate amplifier channels coupled to electrodes in separate parts of the patient's brain (e.g., in opposite hemispheres). Accordingly, then, the Boolean AND operation 1068 will indicate a detection only when the first detection output 1060 and the second detection output 1064 both indicate the presence of an signal event (or, when Boolean logic inversion 1066 is present, when the first detection output 1060 indicates the presence of a signal event while the second detection output 1064 does not). As will be described in further detail below, the detection outputs 1060 and 1064 can be provided with selectable persistence (i.e., the ability to remain triggered for some time after the signal event is detected), allowing the Boolean AND combination 1068 to be satisfied even when there is not precise temporal synchronization between detections on the two channels.

It should be appreciated that the concept of a "qualifying channel" allows the flexible configuration of a device 310 according to the invention to achieve a number of advantageous results. In addition to the detection of generalization, as described above, a qualifying channel can be configured, for example, to detect noise so a detection output is valid only when noise is not present, to assist in device configuration in determining which of two sets of detection parameters is preferable (by setting up the different parameters in the first detection channel and the second detection channel, then replacing the Boolean AND combination with a Boolean OR combination), or to require a specific temporal sequence of detections (which would be achieved in software by the CPU 528 after a Boolean OR combination of detections). Moreover, a qualifying channel can receive data from the same input channel as the first detection channel, allowing the correlation of separate pattern characteristics occurring at the same time in the same waveform. There are numerous other possibilities.

The outputs 1034, 1038, and 1056 of the event detectors are preferably represented by Boolean flags, and as described below, provide information for the operation of a system according to the invention.

While FIG. 10 illustrates four different sensing channels providing input to four separate detection channels, it should be noted that a maximally flexible embodiment of the present invention would allow each sensing channel to be connected to one or more detection channels. It may be advantageous to program the different detection channels with different settings (e.g., thresholds) to facilitate alternate "views" of the same sensing channel data stream.

Figure 11:
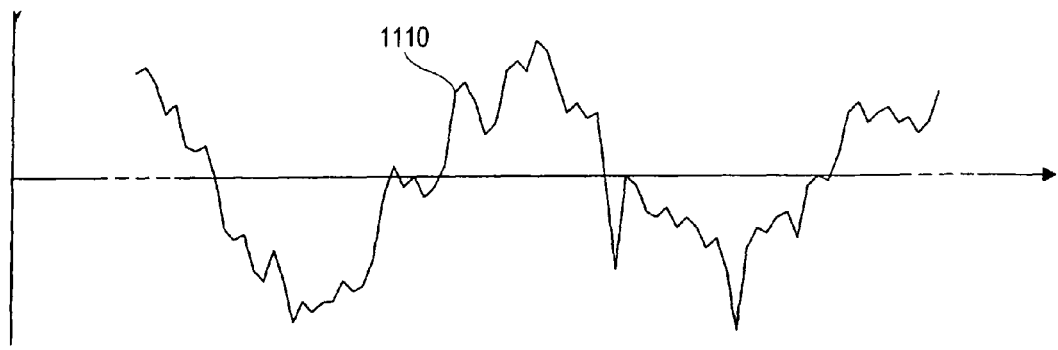
FIG. 11 is a graph of an exemplary EEG signal, illustrating decomposition of the signal into time windows and samples.
Figure 11:
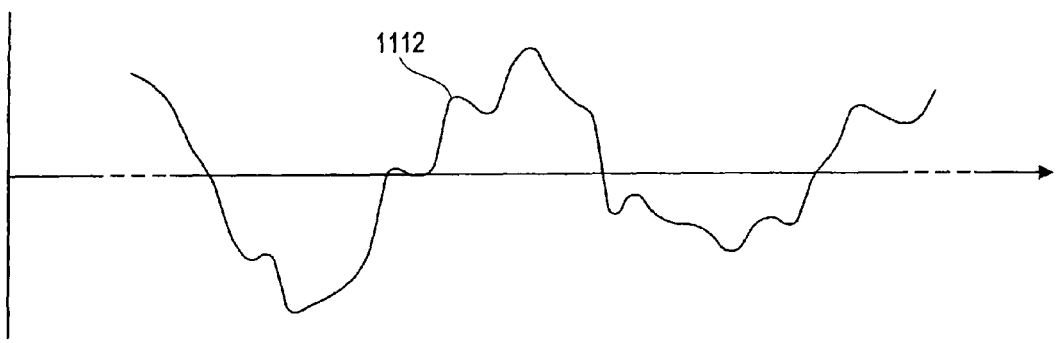
Figure 11:
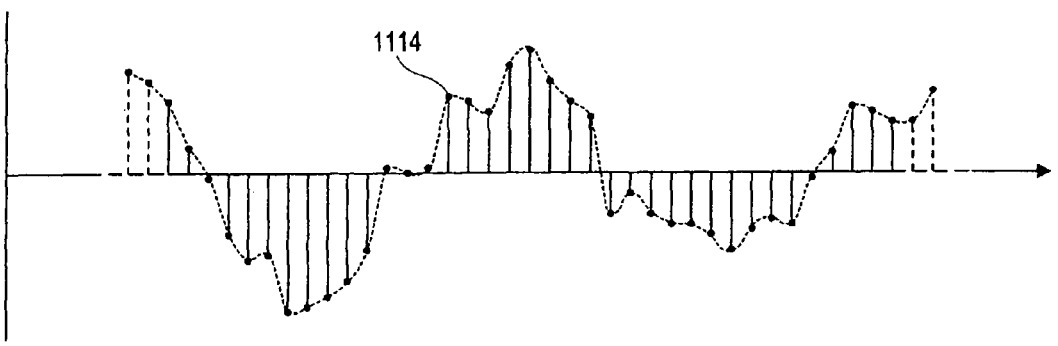

FIG. 11 illustrates three representative waveforms of the type expected to be manipulated by a system according to the invention. It should be noted, however, that the waveforms illustrated in FIG. 11 are illustrative only, and are not intended to represent any actual data. The first waveform 1110 is representative of an unprocessed electroencephalogram (EEG) or electrocorticogram (ECOG) waveform having a substantial amount of variability; the illustrated segment has a duration of approximately 160 ms and a dominant frequency (visible as the large-scale crests and valleys) of approximately 12.5 Hz. It will be recognized that the first waveform is rather rough and peaky; there is a substantial amount of high-frequency energy represented therein.

The second waveform 1112 represents a filtered version of the original EEG waveform 1110. As shown, most of the high-frequency energy has been eliminated from the signal, and the waveform 1112 is significantly smoother. In the disclosed embodiment of the invention, this filtering operation is performed in the sensing front end 712 (FIG. 7) before the analog to digital converters 812 (FIG. 8).

The filtered waveform 1112 is then sampled by one of the analog to digital converters 812; this operation is represented graphically in the third waveform 1114 of FIG. 11. As illustrated, a sample rate used in an embodiment of the invention is 250 Hz (4 ms sample duration), resulting in approximately 40 samples over the illustrated 160 ms segment. As is well known in the art of digital signal processing, the amplitude resolution of each sample is limited; in the disclosed embodiment, each sample is measured with a resolution of 10 bits (or 1024 possible values). As is apparent upon visual analysis of the third waveform, the dominant frequency component has a wavelength of approximately 20 samples, which corresponds to the dominant frequency of 12.5 Hz.

Figure 12:
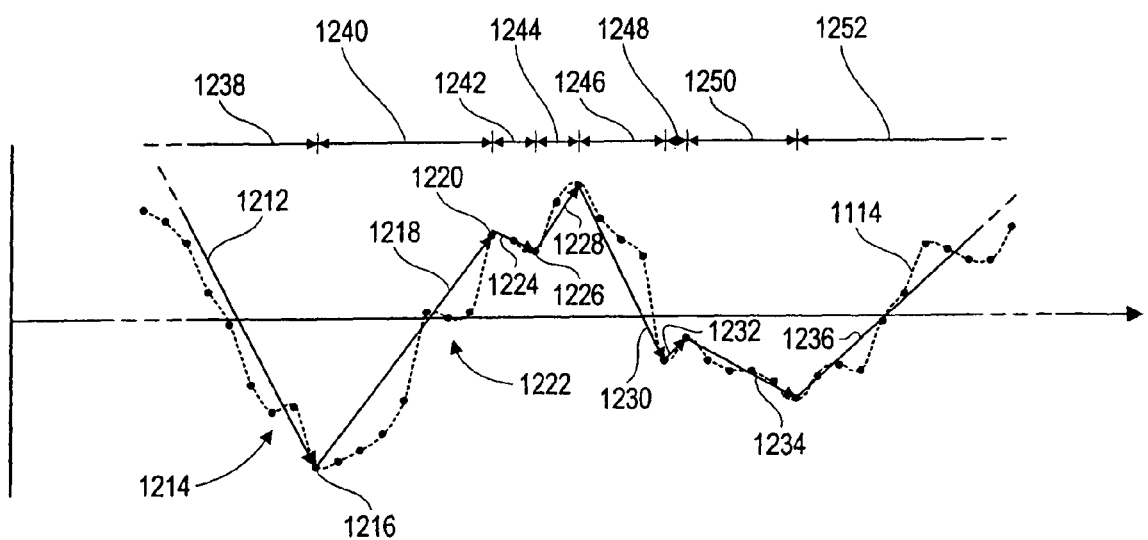
FIG. 12 is a graph of the exemplary EEG signal of FIG. 11, illustrating the extraction of half waves from the signal.

Referring now to FIG. 12, the processing of the wave morphology analysis units 912 is described in conjunction with a filtered and sampled waveform 1114 of the type illustrated as the third waveform 1114 of FIG. 11.

In a first half wave 1212, which is partially illustrated in FIG. 12 (the starting point occurs before the illustrated waveform segment 1114 begins), the waveform segment 1114 is essentially monotonically decreasing, except for a small first perturbation 1214. Accordingly, the first half wave 1212 is represented by a vector from the starting point (not shown) to a first local extremum 1216, where the waveform starts to move in the opposite direction. The first perturbation 1214 is of insufficient amplitude to be considered a local extremum, and is disregarded by a hysteresis mechanism (discussed in further detail below). A second half wave 1218 extends between the first local extremum 1216 and a second local extremum 1220. Again, a second perturbation 1222 is of insufficient amplitude to be considered an extremum. Likewise, a third half wave 1224 extends between the second local extremum 1220 and a third local extremum 1226; this may appear to be a small perturbation, but is greater in amplitude than a selected hysteresis threshold. The remaining half waves 1228, 1230, 1232, 1234, and 1236 are identified analogously. As will be discussed in further detail below, each of the identified half waves 1212, 1218, 1224, 1228, 1230, 1232, 1234, and 1236 has a corresponding duration 1238, 1240, 1242, 1244, 1246, 1248, 1250, and 1252, respectively, and analogously, a corresponding amplitude determined from the relative positions of each half wave's starting point and ending point along the vertical axis, and a slope direction, increasing or decreasing.

In a method performed according to the invention, it is particularly advantageous to allow for a programmable hysteresis setting in identifying the ends of half waves. In other words, as explained above, the end of an increasing or decreasing half wave might be prematurely identified as a result of quantization (and other) noise, low-amplitude signal components, and other perturbing factors, unless a small hysteresis allowance is made before a reversal of waveform direction (and a corresponding half wave end) is identified. Hysteresis allows for insignificant variations in signal level inconsistent with the signal's overall movement to be ignored without the need for extensive further signal processing such as filtering. Without hysteresis, such small and insignificant variations might lead to substantial and gross changes in where half waves are identified, leading to unpredictable results.

Figure 13:
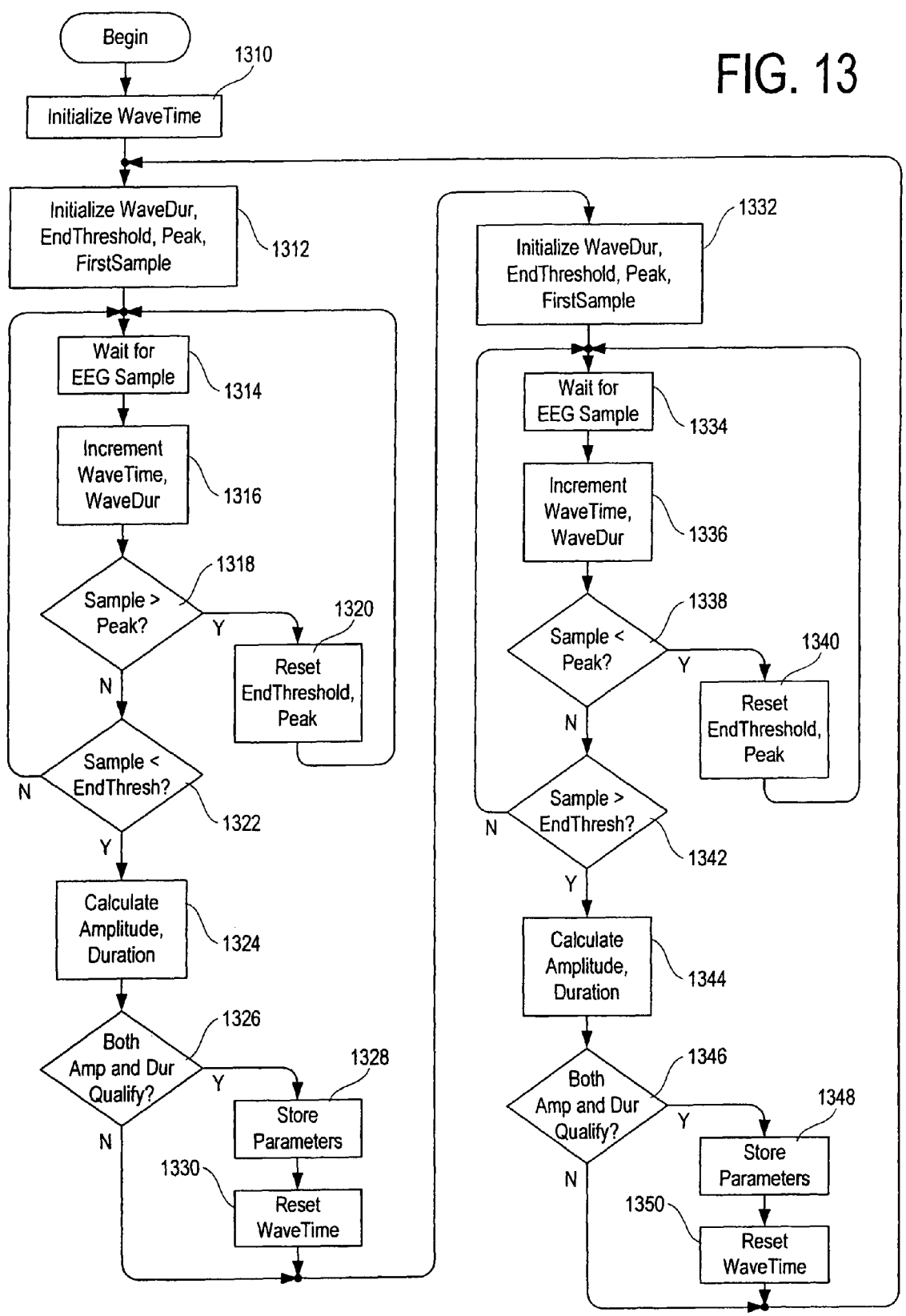
FIG. 13 is a flow chart illustrating the process performed by hardware functional components of the waveform analyzer of FIG. 9 in extracting half waves as illustrated in FIG. 12.

The processing steps performed with regard to the waveform 1114 and half waves of FIG. 12 are set forth in FIG. 13. The method begins by identifying an increasing half wave (with an ending amplitude higher than the starting amplitude, as in the second half wave 1218 of FIG. 12). To do this, a variable corresponding to half wave time is first initialized to zero (step 1310); then half wave duration, ending threshold, peak amplitude, and first sample value are all initialized (step 1312). Specifically, the half wave duration value is set to zero; the peak amplitude and first sample values are set to the amplitude value of the last observed sample, which as described above is a value having 10-bit precision; and the ending threshold is set to the last observed sample minus a small preset hysteresis value. After waiting for a measurement of the current EEG sample (step 1314), the half wave time and half wave duration variables are incremented (step 1316). If the current EEG sample has an amplitude greater than the peak amplitude (step 1318), then the amplitude of the half wave is increasing (or continues to increase). Accordingly, the ending threshold is reset to be the current EEG sample's amplitude minus the hysteresis value, and the peak is reset to the current EEG sample's amplitude (step 1320), and the next sample is awaited (step 1314).

If the current EEG sample has an amplitude less than the ending threshold (step 1322), then the hysteresis value has been exceeded, and a local extremum has been identified. Accordingly, the end of the increasing half wave has been reached, and the amplitude and duration of the half wave are calculated (step 1324). The amplitude is equal to the peak amplitude minus the first sample value; the duration is equal to the current half wave duration. Otherwise, the next ample is awaited (step 1314).

If both the amplitude and the duration qualify by exceeding corresponding preset thresholds (step 1326), then the amplitude, duration, half wave time, half wave direction (increasing) are stored in a buffer (step 1328), and the half wave time is reset to zero (step 1330).

At the conclusion of the increasing half wave, the process continues by initializing wave duration, the ending threshold, the peak amplitude, and the first sample value (step 1332). Wave duration is set to zero, the ending threshold is set to the last sample value plus the hysteresis value, the peak amplitude and the first sample value are set to the most recent sample value.

After waiting for a measurement of the current EEG sample (step 1334), the half wave time and half wave duration variables are incremented (step 1336). If the current EEG sample has an amplitude lower than the peak amplitude (step 1338), then the amplitude of the half wave is decreasing (or continues to decrease). Accordingly, the ending threshold is reset to be the current EEG sample's amplitude plus the hysteresis value, the peak is reset to the current EEG sample's amplitude (step 1340), and the next sample is awaited (step 1334).

If the current EEG sample has an amplitude greater than the ending threshold (step 1342), then the hysteresis value has been exceeded, and a local extremum has been identified. Accordingly, the end of the decreasing half wave has been reached, and the amplitude and duration of the half wave are calculated (step 1344). The amplitude is equal to the first sample value minus the peak amplitude, and the duration is equal to the current half wave duration. Otherwise, the next EEG sample is awaited (step 1334).

If both the amplitude and the duration qualify by exceeding corresponding preset thresholds (step 1346), then the amplitude, duration, half wave time, half wave direction (decreasing) are stored in a buffer (step 1348), and the half wave time is reset to zero (step 1350). It should be noted that, in the context of this specification, the term "exceed" in regard to a threshold value means to meet a specified criterion. Generally, to exceed a threshold herein is to have a numeric value greater than or equal to the threshold, although other interpretations (such as greater than, or less than, or less than or equal to, depending on the context) may be applicable and are deemed to be within the scope of the invention.

At the conclusion of the decreasing half wave, further half waves are then identified by repeating the process from step 1312. As half wave detection is an ongoing and continuous process, this procedure preferably does not exit, but may be suspended from time to time when conditions or device state call for it, e.g. when the device is inactive or when stimulation is being performed. Once suspended in accordance with the invention, the procedure should recommence with the first initialization step 1310.

Accordingly, the process depicted in FIG. 13 stores parameters corresponding to qualified half waves, including their directions, durations, amplitudes, and the elapsed time between adjacent qualified half waves (i.e. the half wave time variable). In the disclosed embodiment of the invention, to reduce power consumption, this procedure is performed in custom electronic hardware; it should be clear that the operations of FIG. 13 are performed in parallel for each active instance of the wave morphology analysis units 912 (FIG. 9). It should also be noted, however, that certain software can also be used to advantageous effect in this context.

Figure 14:
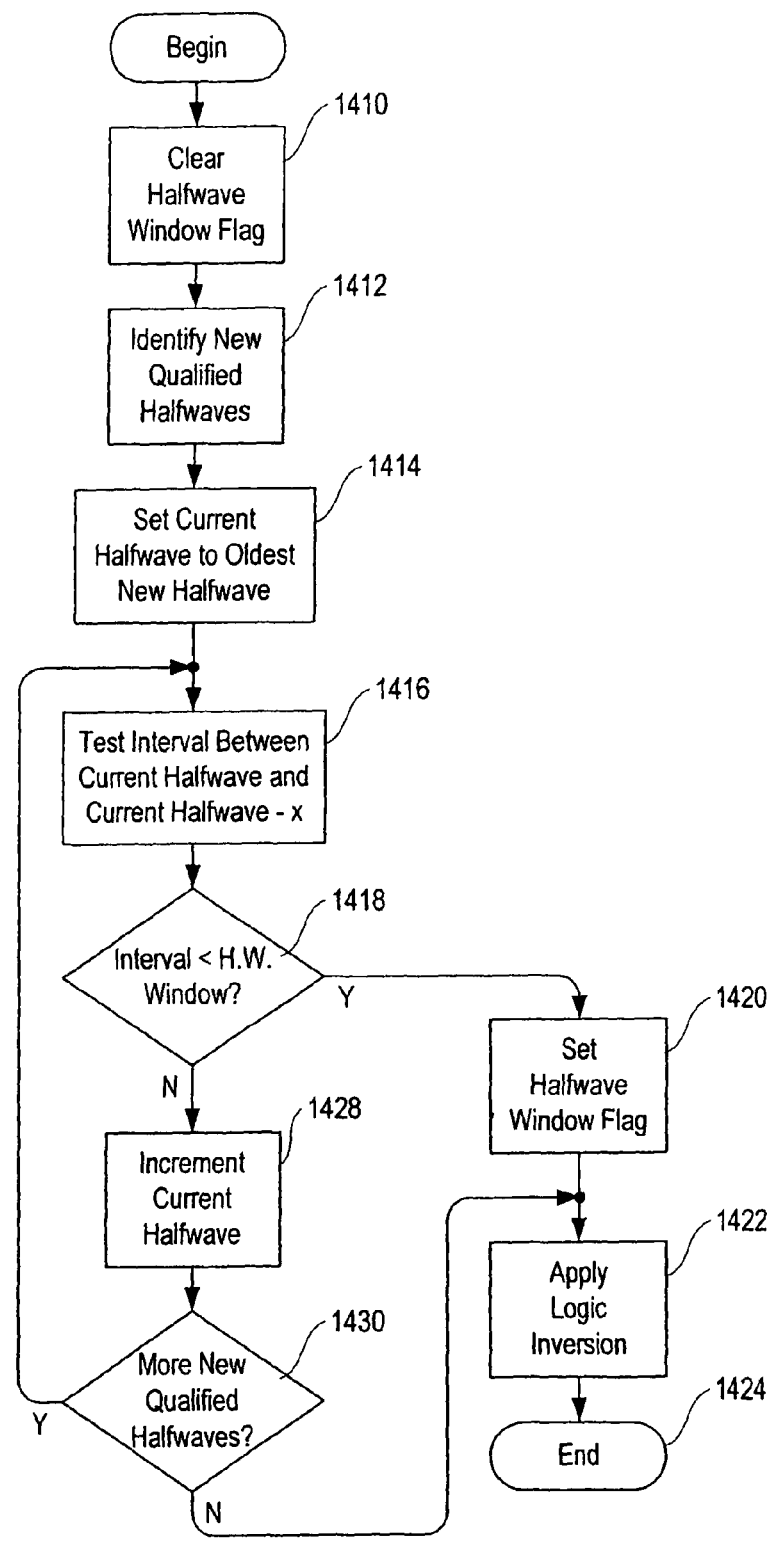
FIG. 14 is a flow chart illustrating the process performed by software in the central processing unit in extracting and analyzing half waves from an EEG signal.

This stored information is used in the software process illustrated in FIG. 14, which is performed on a periodic basis, preferably once every processing window (a recurring time interval that is either fixed or programmable) by a system according to the invention. Consistent with the other analysis tools described herein, the duration of an exemplary processing window is in one embodiment of the invention 128 ms, which corresponds to 32 samples at a 250 Hz sampling rate.

Each time the software process of FIG. 14 is invoked, the half wave window flag is first cleared (step 1410). Any qualified half waves identified by the process set forth in FIG. 13 that are newly identified since the last invocation of the procedure (i.e., all qualified half waves that ended within the preceding processing window) are identified (step 1412). A "current half wave" pointer is set to point to the oldest qualified half wave identified in the most recent processing window (step 1414). The time interval between the current half wave and the prior x half waves is then measured (step 1416), where x is a specified minimum number of half waves (preferably a programmable value) to be identified within a selected half wave time window (the duration of which is another programmable value) to result in the possible detection of a neurological event. If the time interval is less than the duration of the half wave time window (step 1418), then the half wave window flag is set (step 1420), logic inversion is selectively applied (step 1422), and the procedure ends (step 1424). Logic inversion, a mechanism for determining whether an analysis unit is triggered by the presence or absence of a condition, is explained in greater detail below. Otherwise, the current half wave pointer is incremented to point to the next new half wave (step 1428), and if there are no more new half waves (step 1430), logic inversion is applied if desired (step 1422), and the procedure ends (step 1424). Otherwise, the next time interval is tested (step 1416) and the process continues from there.

Logic inversion allows the output flag for the wave morphology analysis unit (or any other analyzer) to be selectively inverted. If logic inversion is configured to be applied to an output of a particular analysis unit, then the corresponding flag will be clear when the detection criterion (e.g., number of qualified half waves) is met, and set when the detection criterion is not met. This capability provides some additional flexibility in configuration, facilitating detection of the absence of certain signal characteristics when, for example, the presence of those characteristics is the norm.

Figure 15:
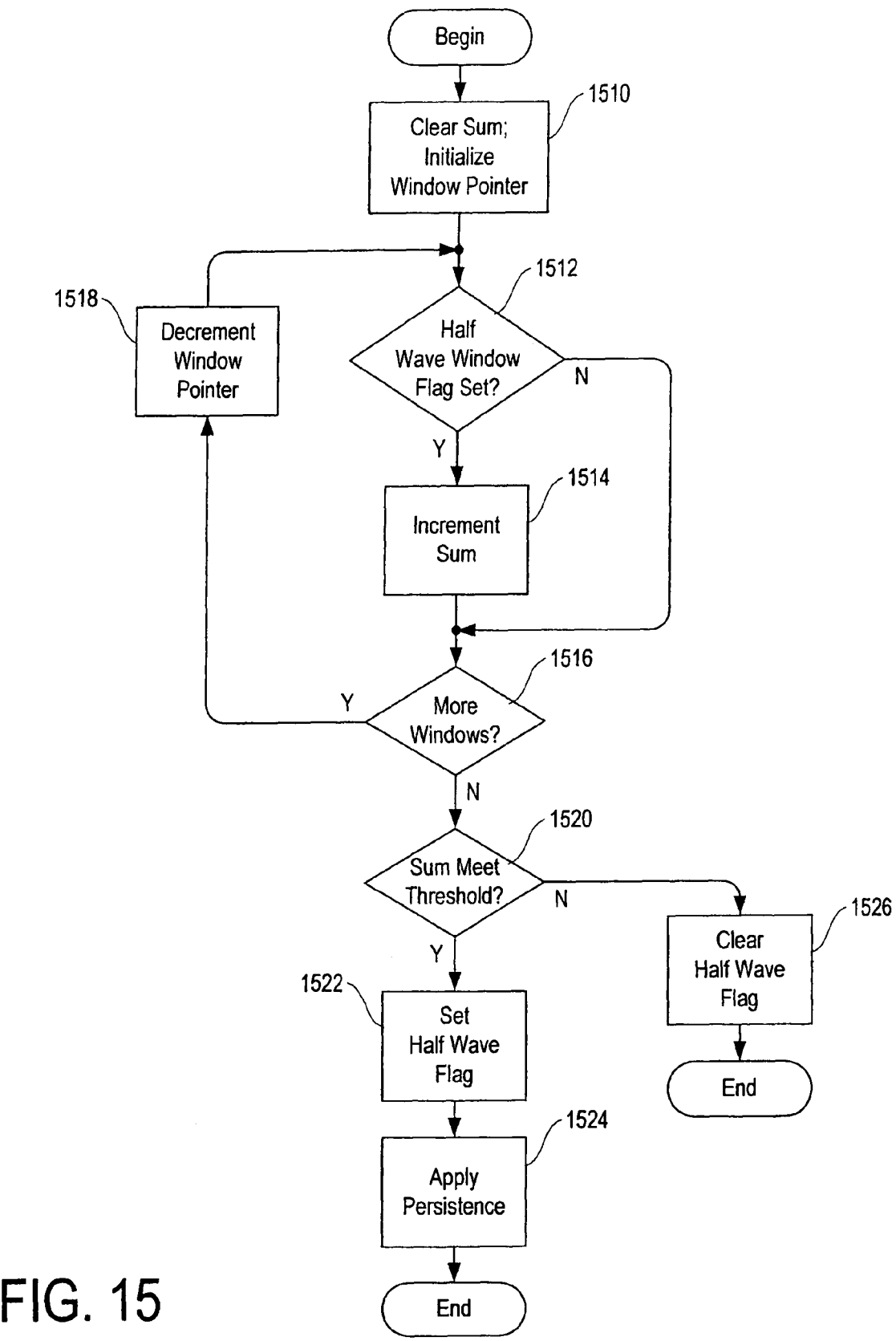
FIG. 15 is a flow chart illustrating the process performed by software in the central processing unit in the application of an X of Y criterion to half wave windows.

In a preferred embodiment of the invention, the half wave window flag (set in step 1420) indicates whether a sufficient number of qualified half waves occur over an interval ending in the most recent processing window. To reduce the occurrence of spurious detections, an X of Y criterion is applied, causing the wave morphology analysis unit to trigger only if a sufficient number of qualified half waves occur in X of the Y most recent processing windows, where X and Y are parameters individually adjustable for each analysis tool. This process is illustrated in FIG. 15.

Initially, a sun (representing recent processing windows having the half wave window flag set) is cleared to zero and a current window pointer is initialized to point to the most recent processing window (step 1510). If the half wave window flag corresponding to the current window pointer is set (step 1512), then the sum is incremented (step 1514). If there are more processing windows to examine (for an X of Y criterion, a total of Y processing windows, including the most recent, should be considered) (step 1516), then the window pointer is decremented (step 1518) and the flag testing and sum incrementing steps (steps 1512-1314) are repeated.

After Y windows have been considered, if the sum of windows having set half wave window flags meets the threshold X (step 1520), then the half wave analysis flag is set (step 1522), persistence (described below) is applied (step 1524), and the procedure is complete. Otherwise, the half wave analysis flag is cleared (step 1526).

Persistence, another per-analysis-tool setting, allows the effect of a signal event detection (a flag set) to persist beyond the end of the detection window in which the signal event occurs. In the disclosed system according to the invention, persistence may be set anywhere from one second to fifteen seconds (though other settings are possible), so if detections with multiple analysis tools do not all occur simultaneously (though they should still occur within a fairly short time period), a Boolean combination of flags will still yield positive results. Persistence can also be used with a single analysis tool to smooth the results.

When the process of FIG. 15 is completed, the half wave analysis flag (set or cleared in steps 1522 and 1526, respectively) indicates whether a signal event has been detected in the corresponding channel of the wave morphology analysis units 912, or stated another way, whether a sufficient number of qualified half waves have appeared in X of the Y most recent processing windows. Although in the disclosed embodiment, the steps of FIGS. 14 and 15 are performed in software, it should be recognized that some or all of those steps can be performed using custom electronics, if it proves advantageous in the desired application to use such a configuration.

Figure 16:
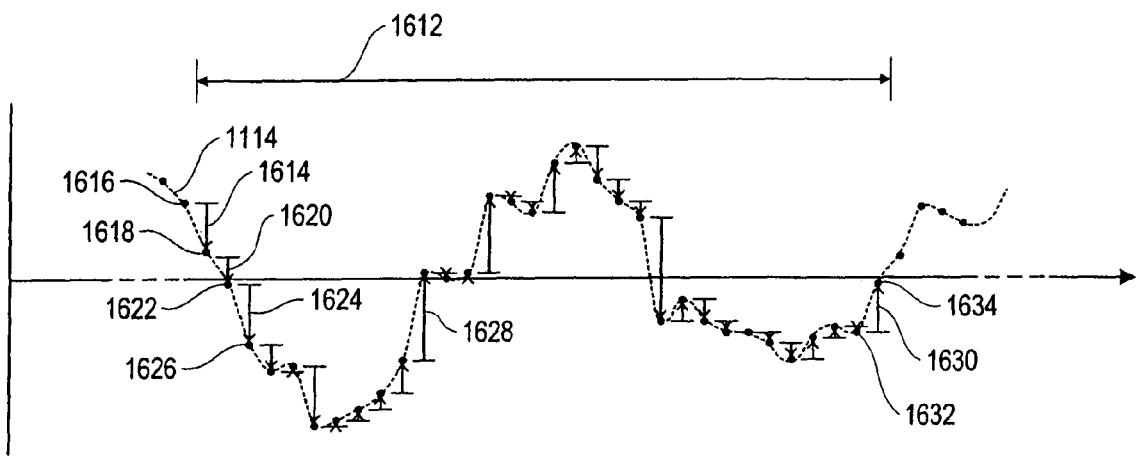
FIG. 16 is a graph of the exemplary EEG signal of FIG. 11, illustrating the calculation of a line length function.

FIG. 16 illustrates the waveform 1114 of FIG. 11, further depicting line lengths identified within a time window. The time window used with respect to FIGS. 16-18 may be different from the half wave processing window described above in connection with FIGS. 14-15, but in a preferred embodiment, refers to the same time intervals. From an implementation standpoint, a single device interrupt upon the conclusion of each processing window allows all of the analysis tools to perform the necessary corresponding software processes; the line length analysis process of FIG. 16 (described below) is one such example. The waveform 1114 is a filtered and otherwise pre-processed EEG signal as received in one of the window analysis units 914 from the sensing front end 712. As discussed above, line lengths are considered within time windows. As illustrated in FIG. 16, the duration of an exemplary window 1612 is 32 samples, which is equivalent to 128 ms at a 250 Hz sampling rate.

The total line length for the window 1612 is the sum of the sample-to-sample amplitude differences within that window 1612. For example, the first contribution to the line length within the window 1612 is a first amplitude difference 1614 between a previous sample 1616 occurring immediately before the window 1612 and a first sample 1618 occurring within the window 1612. The next contribution comes from a second amplitude difference 1620 between the first sample 1618 and a second sample 1622; a further contribution 1624 comes from a third amplitude difference between the second sample 1622 and a third sample 1626; and so on. At the end of the window 1612, the final contribution to the line length comes from a last amplitude difference 1630 between a second-last sample 1632 in the window 1612 and a last sample 1634 in the window 1612. Note that all line lengths, whether increasing or decreasing in direction, are accumulated as positive values by the invention; accordingly, a decreasing amplitude difference 1614 and an increasing amplitude difference 1628 both contribute to a greater line length.

As illustrated herein, and as discussed in detail above, there are thirty-two samples within the window 1612. As stated above, the illustrated window 1612 has a duration of 128 ms, and accordingly, the illustrated sample rate is 250 Hz. It should be noted, however, that alternate window durations and sample rates are possible and considered to be within the scope of the present invention.

Figure 17:
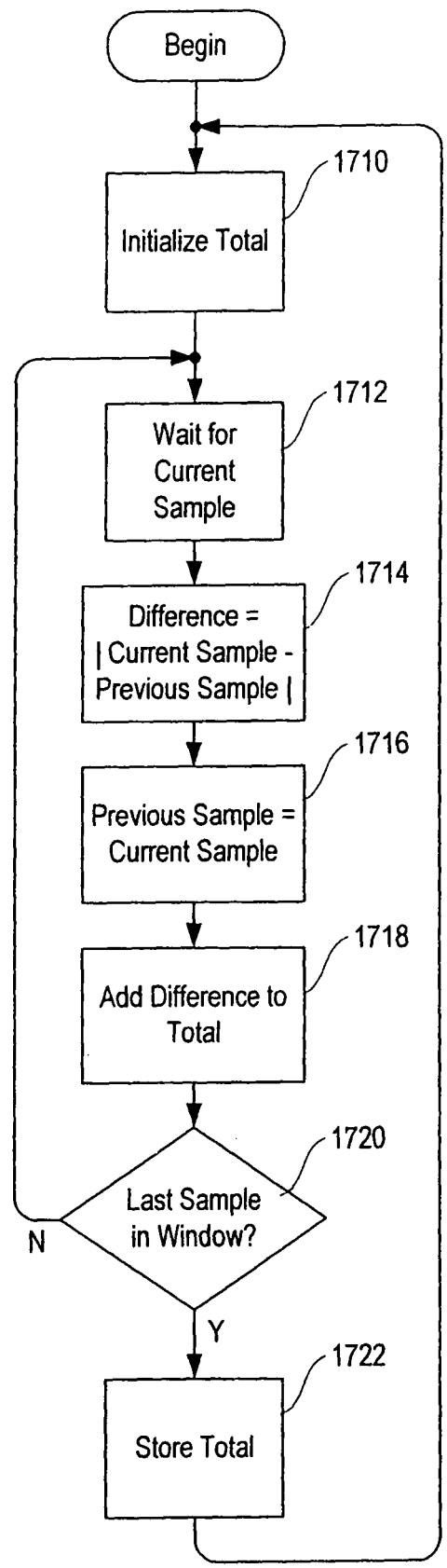
FIG. 17 is a flow chart illustrating the process performed by hardware functional components of the waveform analyzer of FIG. 9 in calculating the line length function as illustrated in FIG. 16.

The line lengths illustrated in FIG. 16 are calculated as shown by the flow chart of FIG. 17, which is invoked at the beginning of a time window. Initially, a line length total variable is initialized to zero (step 1710). The current sample is awaited (step 1712), and the absolute value of the amplitude difference between the current sample and the previous sample (which, when considering the first sample in a window, may come from the last sample in a previous window) is measured (step 1714).

In various alternative embodiments of the invention, either the measured difference (as calculated in step 1714, described above), or the sample values used to calculate the difference may be mathematically transformed in useful nonlinear ways. For example, it may be advantageous in certain circumstances to calculate the difference between adjacent samples using the squares of the sample values, or to calculate the square of the difference between sample values, or both. It is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 310.

For use in the next iteration, the previous sample is replaced with the value of the current sample (step 1716), and the calculated absolute value is added to the total (step 1718). If there are more samples remaining in the window 1412 (step 1720), another current sample is awaited (step 1712) and the process continues. Otherwise, the line length calculation for the window 1412 is complete, and the total is stored (step 1722), the total is re-initialized to zero (step 1710), and the process continues.

As with the half wave analysis method set forth above, the line length calculation does not need to terminate; it can be free-running yet interruptible. If the line length calculation is restarted after having been suspended, it should be re-initialized and restarted at the beginning of a window. This synchronization can be accomplished through hardware interrupts.

Figure 18:
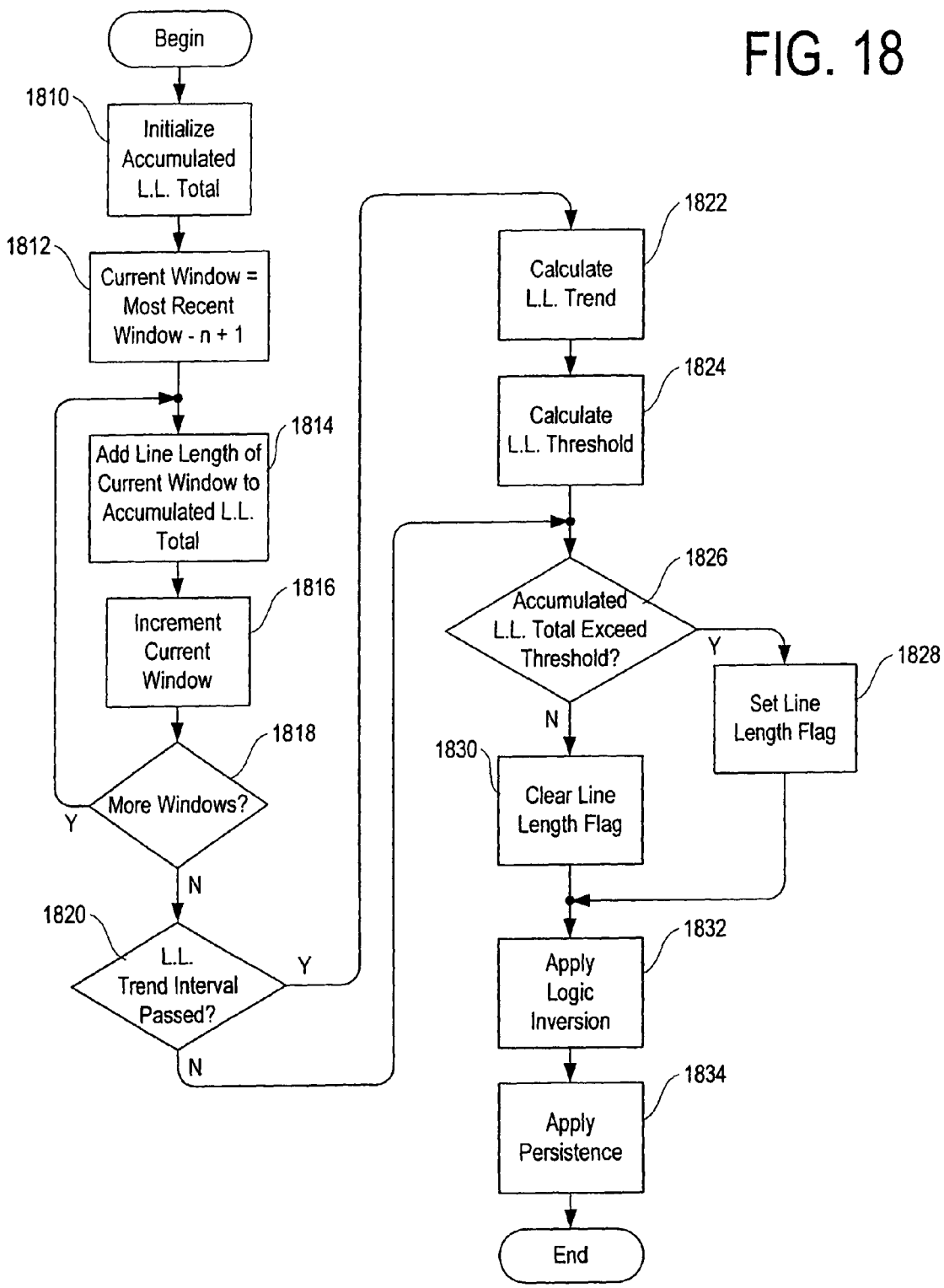
FIG. 18 is a flow chart illustrating the process performed by software in the central processing unit in calculating and analyzing the line length function of an EEG signal.

The line lengths calculated as shown in FIG. 17 are then processed as indicated in the flow chart of FIG. 18, which is performed after each window 1612 is calculated and stored (step 1722).

The process begins by calculating a running accumulated line length total over a period of n time windows. Where n>1, the effect is that of a sliding window; in an alternative embodiment an actual sliding window processing methodology may be used. First, the accumulated total is initialized to zero (step 1810). A current window pointer is set to indicate the $n^{th}$-last window, i.e., the window (n−1) windows before the most recent window (step 1812). The line length of the current window is added to the total (step 1814), the current window pointer is incremented (step 1816), and if there are more windows between the current window pointer and the most recent (last) window (step 1818), the adding and incrementing steps (1814-1816) are repeated. Accordingly, by this process, the resulting total includes the line lengths for each of the n most recent windows.

In the disclosed embodiment of the invention, the accumulated total line length is compared to a dynamic threshold, which is based on a trend of recently observed line lengths. The trend is recalculated regularly and periodically, after each recurring line length trend interval (which is preferably a fixed or programmed time interval). Each time the line length trend interval passes (step 1820), the line length trend is calculated or updated (step 1822). In a presently preferred embodiment of the invention, this is accomplished by calculating a normalized moving average of several trend samples, each of which represents several consecutive windows of line lengths. A new trend sample is taken and the moving average is recalculated upon every line length trend interval. The number of trend samples used in the normalized moving average and the number of consecutive windows of line length measurements per trend sample are preferably both fixed or programmable values.

After the line length trend has been calculated, the line length threshold is calculated (step 1824) based on the new line length trend. In the disclosed embodiment of the invention, the threshold may be set as either a percentage of the line length trend (either below 100% for a threshold that is lower than the trend, or above 100% for a threshold that is higher than the trend) or alternatively a fixed numeric offset from the line length trend (either negative for a threshold that is lower than the trend, or positive for a threshold that is higher than the trend). It should be observed that other methods for deriving a numeric threshold from a numeric trend are possible and deemed to be within the scope of the invention.

The first time the process of FIG. 18 is performed, there is generally no line length trend against which to set a threshold. Accordingly, for the first several passes through the process (until a sufficient amount of EEG data has been processed to establish a trend), the threshold is essentially undefined and the line length detector should not return a positive detection. Some "settling time" is required to establish trends and thresholds before a detection can be made.

If the accumulated line length total exceeds the calculated threshold (step 1826), then a flag is set (step 1828) indicating a line-length-based signal event detection on the current window analysis unit channel 914. As described above, in the disclosed embodiment of the invention, the threshold is dynamically calculated from a line length trend, but alternatively, the threshold may be static, either fixed or programmed into the device 310. If the accumulated line length total does not exceed the threshold, the flag is cleared (step 1830). Once the line length flag has been either set or cleared, logic inversion is applied (step 1832), persistence is applied (step 1834), and the procedure terminates.

The resulting persistent line length flag indicates whether the threshold has been exceeded within one or more windows over a time period corresponding to the line length flag persistence. As will be discussed in further detail below, line length signal event detections can be combined with the half wave signal event detections, as well as any other applicable detection criteria according to the invention.

Figure 19:
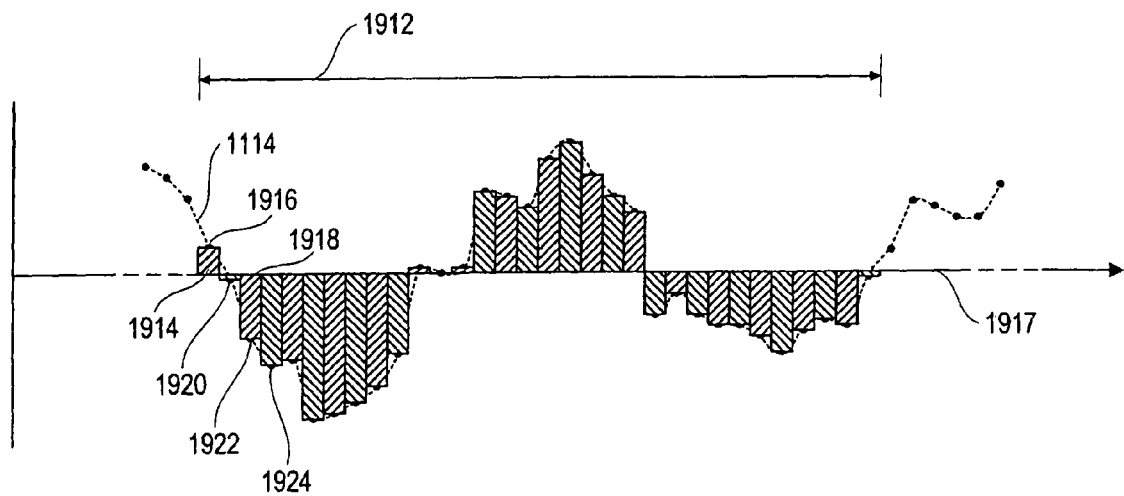
FIG. 19 is a graph of the exemplary EEG signal of FIG. 11, illustrating the calculation of an area function.

FIG. 19 illustrates the waveform of FIG. 11 with area under the curve identified within a window. Area under the curve, which in some circumstances is somewhat representative of a signal's energy (though energy of a waveform is more accurately represented by the area under the square of a waveform), is another detection criterion in accordance with the invention.

The total area under the curve represented by the waveform 1114 within the window 1912 is equal to the sum of the absolute values of the areas of each rectangular region of unit width vertically bounded by the horizontal axis and the sample. For example, the first contribution to the area under the curve within the window 1912 comes from a first region 1914 between a first sample 1916 and a baseline 1917. A second contribution to the area under the curve within the window 1912 comes from a second region 1918, including areas between a second sample 1920 and the baseline 1917. There are similar regions and contributions for a third sample 1922 and the baseline 1917, a fourth sample 1924 and the baseline 1917, and so on. It should be observed that the region widths are not important—the area under each sample can be considered the product of the sample's amplitude and a unit width, which can be disregarded. In a similar manner, each region is accumulated and added to the total area under the curve within the window 1912. Although the concept of separate rectangular regions is a useful construct for visualizing the idea of area under a curve, it should be noted that a process for calculating area need not partition areas into regions as shown in FIG. 19—it is only necessary to accumulate the absolute value of the waveform's amplitude at each sample, as the unit width of each region can be disregarded. The process for doing this will be set forth in detail below in connection with FIG. 20.

Figure 20:
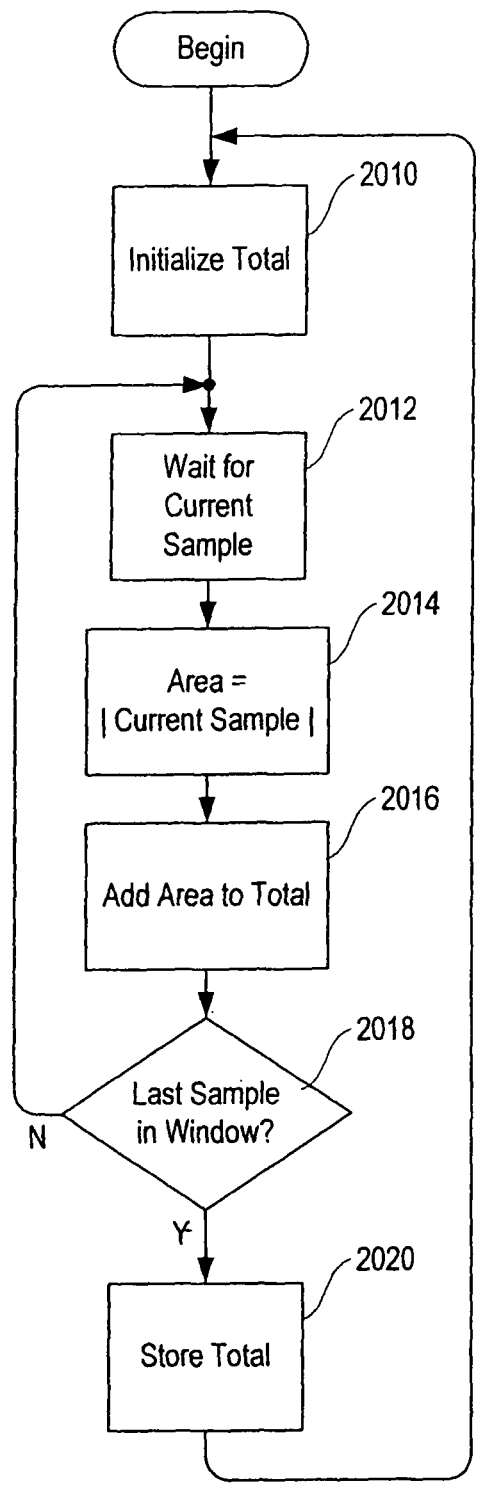
FIG. 20 is a flow chart illustrating the process performed by hardware functional components of the waveform analyzer of FIG. 7 in calculating the area function as illustrated in FIG. 19.

The areas under the curve illustrated in FIG. 19 are calculated as shown by the flow chart of FIG. 20, which is invoked at the beginning of a time window. Initially, an area total variable is initialized to zero (step 2010). The current sample is awaited (step 2012), and the absolute value of the current sample is measured (step 2014).

As with the line length calculation method described above (with reference to FIG. 17), in various alternative embodiments of the invention, the current sample (as measured in step 2014, described above) may be mathematically transformed in useful nonlinear ways. For example, it may be advantageous in certain circumstances to calculate the square of the current sample rather than its absolute value. The result of such a transformation by squaring each sample will generally be more representative of signal energy, though it is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 310.

The calculated absolute value is added to the total (step 2016). If there are more samples remaining in the window 1912 (step 2018), another current sample is awaited (step 2012) and the process continues. Otherwise, the area calculation for the window 1912 is complete, and the total is stored (step 2020), the total is re-initialized to zero (step 2010), and the process continues.

As with the half wave and line length analysis methods set forth above, the area calculation does not need to terminate; it can be free-running yet interruptible. If the area calculation is restarted after having been suspended, it should be re-initialized and restarted at the beginning of a window. This synchronization can be accomplished through hardware interrupts.

Figure 21:
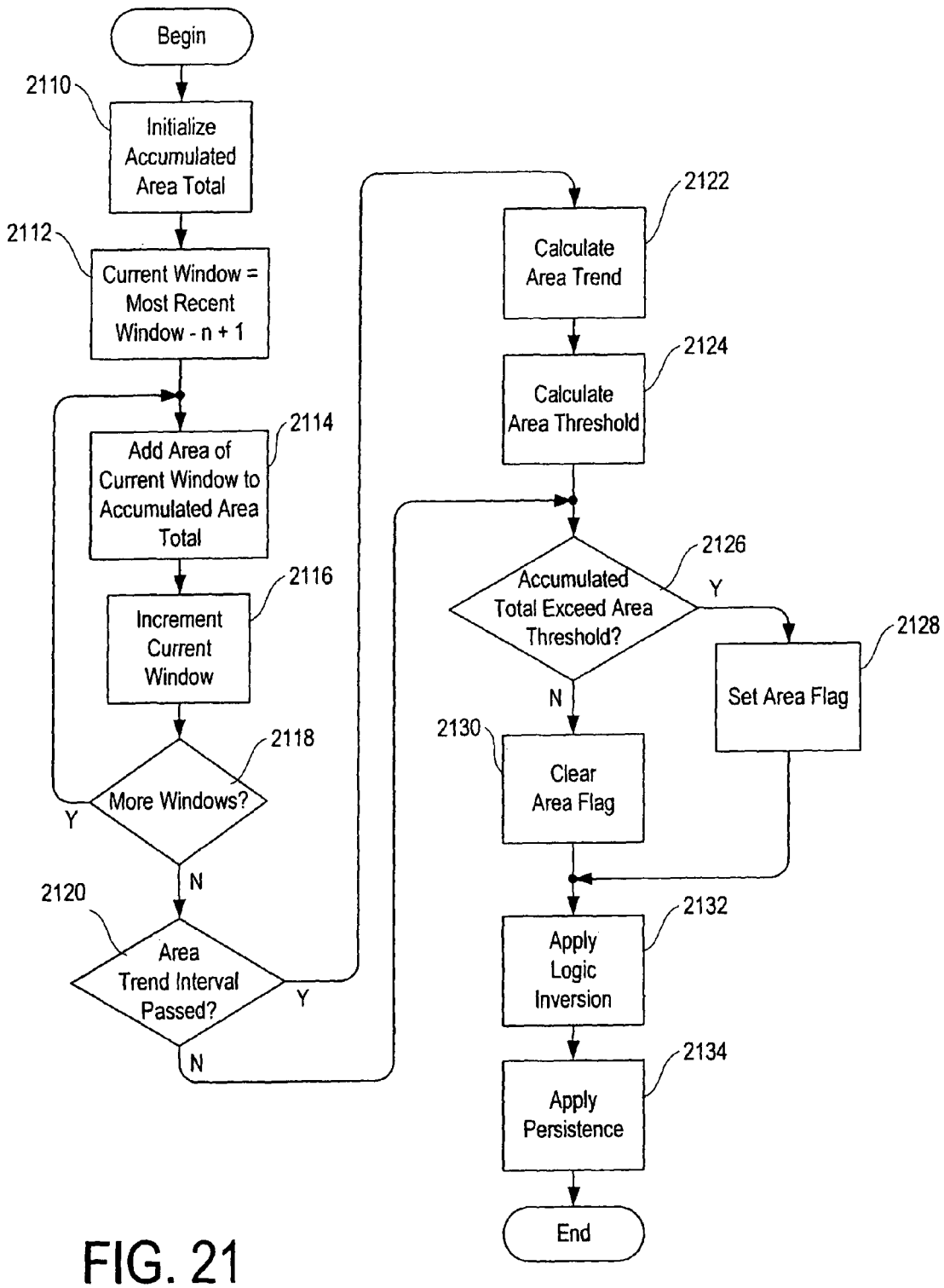
FIG. 21 is a flow chart illustrating the process performed by software in the central processing unit in calculating and analyzing the area function of an EEG signal.

The line lengths calculated as shown in FIG. 20 are then processed as indicated in the flow chart of FIG. 21, which is performed after each window 1912 is calculated and stored (step 2020).

The process begins by calculating a running accumulated area total over a period of n time windows. Where n>1, the effect is that of a sliding window; in an alternative embodiment an actual sliding window processing methodology may be used. First, the accumulated total is initialized to zero (step 2110). A current window pointer is set to indicate the $n^{th}$-last window, i.e., the window (n−1) windows before the most recent window (step 2112). The area for the current window is added to the total (step 2114), the current window pointer is incremented (step 2116), and if there are more windows between the current window and the most recent (last) window (step 2118), the adding and incrementing steps (2114-2116) are repeated. Accordingly, by this process, the resulting total includes the areas under the curve for each of the n most recent windows.

In the disclosed embodiment of the invention, the accumulated total area is compared to a dynamic threshold, which is based on a trend of recently observed areas. The trend is recalculated regularly and periodically, after each recurring area trend interval (which is preferably a fixed or programmed time interval). Each time the area trend interval passes (step 2120), the area trend is calculated or updated (step 2122). In a presently preferred embodiment of the invention, this is accomplished by calculating a normalized moving average of several trend samples, each of which represents several consecutive windows of areas. A new trend sample is taken and the moving average is recalculated upon every area trend interval. The number of trend samples used in the normalized moving average and the number of consecutive windows of area measurements per trend sample are preferably both fixed or programmable values.

After the area trend has been calculated, the area threshold is calculated (step 2124) based on the new area trend. As with line length, discussed above, the threshold may be set as either a percentage of the area trend (either below 100% for a threshold that is lower than the trend, or above 100% for a threshold that is higher than the trend) or alternatively a fixed numeric offset from the area trend (either negative for a threshold that is lower than the trend, or positive for a threshold that is higher than the trend).

The first time the process of FIG. 21 is performed, there is generally no area trend against which to set a threshold. Accordingly, for the first several passes through the process (until a sufficient amount of EEG data has been processed to establish a trend), the threshold is essentially undefined and the area detector should not return a positive detection. Some "settling time" is required to establish trends and thresholds before a detection can be made.

If the accumulated total exceeds the calculated threshold (step 2126), then a flag is set (step 2128) indicating an area-based signal event detection on the current window analysis unit channel 914. Otherwise, the flag is cleared (step 2130). Once the area flag has been either set or cleared, logic inversion is applied (step 2132), persistence is applied (step 2134), and the procedure terminates.

The resulting persistent area flag indicates whether the threshold has been exceeded within one or more windows over a time period corresponding to the area flag persistence. As will be discussed in further detail below, area signal event detections can be combined with the half wave signal event detections, line length signal event detections, as well as any other applicable detection criteria according to the invention.

In a preferred embodiment of the invention, each threshold for each channel and each analysis tool can be programmed separately; accordingly, a large number of individual thresholds may be used in a system according to the invention. It should be noted thresholds can vary widely; they can be updated by a physician via the external programmer 612 (FIG. 6), and some analysis tool thresholds (e.g., line length and area) can also be automatically varied depending on observed trends in the data. This is preferably accomplished based on a moving average of a specified number of window observations of line length or area, adjusted as desired via a fixed offset or percentage offset, and may compensate to some extent for diurnal and other normal variations in brain electrophysiological parameters.

With regard to the flow charts of FIGS. 13-15, 17-18, and 20-21, it should be noted that there can be a variety of ways these processes are implemented. For example, software, hardware (including ASICs, FPGAs, and other custom electronics), and various combinations of software and hardware, are all solutions that would be possible to practitioners of ordinary skill in the art of electronics and systems design. It should further be noted that the steps described herein as performed in software need not be, as some of them can be implemented in hardware, if desired, to further reduce computational load on the processor. In the context of the invention, it is not believed to be advantageous to have the software perform additional steps, as that would likely increase power consumption.

In an embodiment of the invention, one of the detection schemes set forth above (e.g., half wave detection) is adapted to use an X of Y criterion to weed out spurious detections. This can be implemented via a shift register, as usual, or by more efficient computational methods. As described above, half waves are analyzed on a window-by-window basis, and as described above (in connection with FIG. 15), the window results are updated on a separate analysis window interval. If the detection criterion (i.e., a certain number of half waves in less than a specified time period) is met for any of the half waves occurring in the most recent window, then detection is satisfied within that window. If that occurs for at least X of the Y most recent windows, then the half wave analysis tool triggers a detection. If desired, other detection algorithms (such as line length and area) may operate in much the same way: if thresholds are exceeded in at least X of the Y most recent windows, then the corresponding analysis tool triggers a detection.

Also, in the disclosed embodiment, each detection flag, after being set, remains set for a selected amount of time, allowing them to be combined by Boolean logic (as described below) without necessarily being simultaneous.

As indicated above, each of the software processes set forth above (FIGS. 14-15, 18, and 21) corresponds to functions performed by the wave morphology analysis units 912 and window analysis units 914. Each one is initiated periodically, typically once per detection window (steps 1412 and 1712/1912). The outputs from the wave morphology and window analysis units 912 and 914, namely the flags generated in response to counted qualified half waves, accumulated line lengths, and accumulated areas are combined to identify signal event detections as functionally illustrated in FIG. 10 and as described via flow chart in FIG. 27 below.

Patterns and sequences are identified by a system according to the invention via finite state machines programmed into the neurostimulator device 310 (FIG. 3); these state machines are implemented as described below with reference to FIGS. 22-26.

Figure 22:
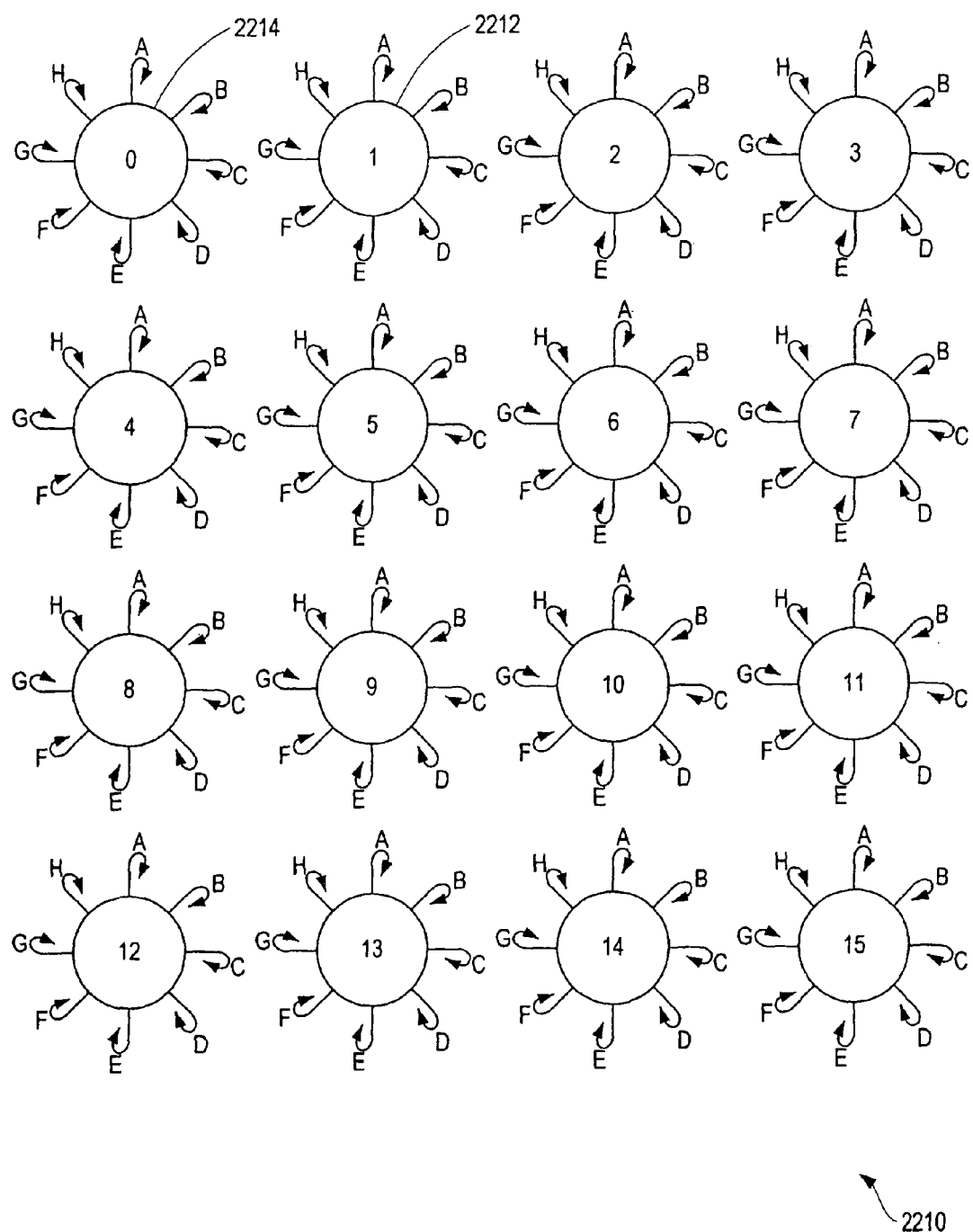
FIG. 22 is an unconfigured state transition diagram as embodied in an unprogrammed implantable device according to the invention.

Referring now to FIG. 22, an unconfigured set of states and transition events 2210 according to the invention is illustrated. There are sixteen possible states (numbered 0 through 15 in the illustrated example), and there are eight possible transition events (letters A through H) permitting transition out of any of the states. In any particular state machine according to the invention, it is not necessary to use all sixteen states or eight transition events; a subset may be used. In the default condition, each of the sixteen states, including an exemplary first state 2212 (note that the "0"-labeled state 2214 is reserved for use as an initial state, such as the initial state 2312 of FIG. 23), is set up such that any of the possible transition events (A-H) does not cause a transition, indicated in the Figures by a loop back to the same state.

Figure 23:
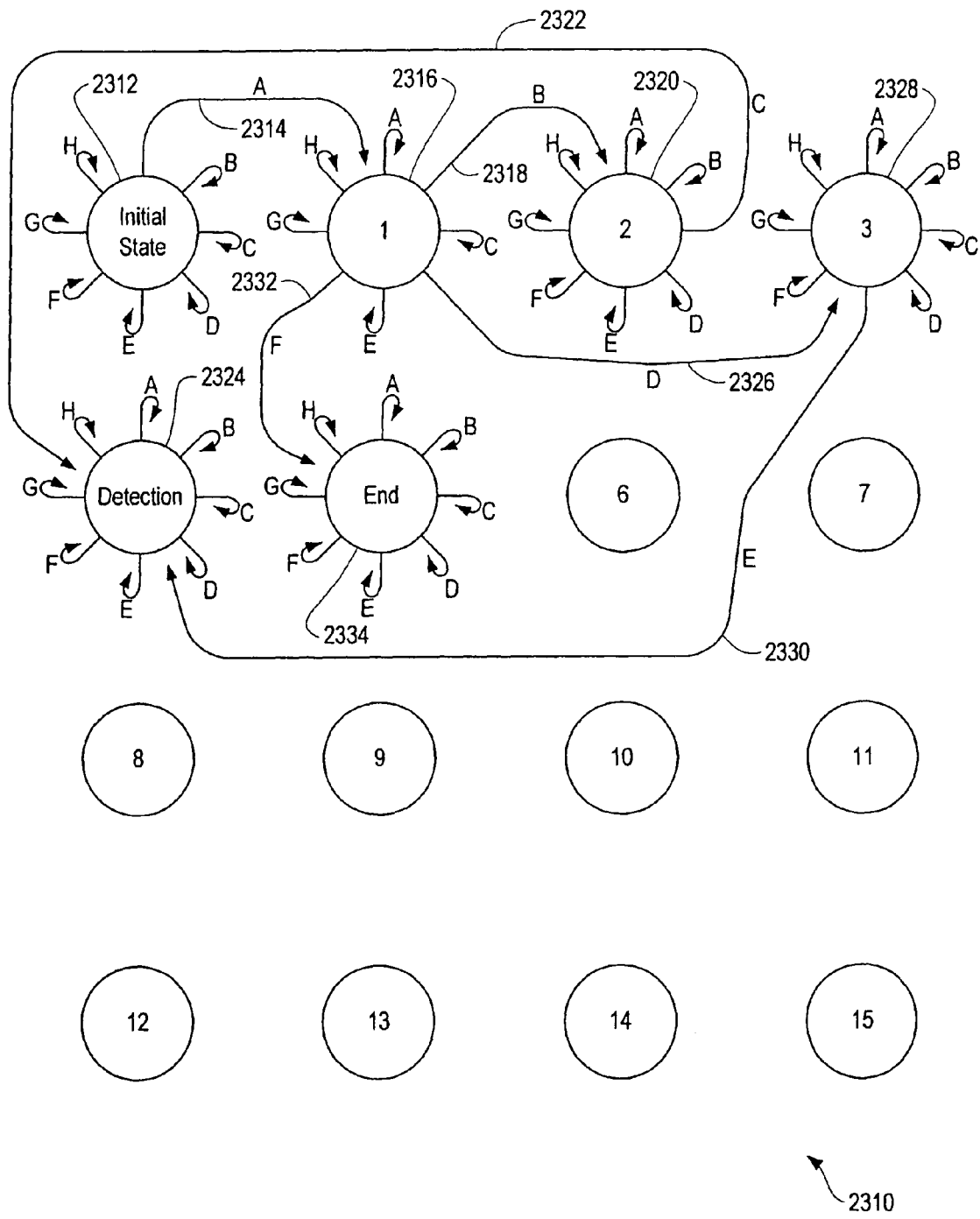
FIG. 23 is the state transition diagram of FIG. 1 as represented in a programmed implantable device according to the invention.

The states and transition events 2210 of FIG. 22 are configured into an exemplary state machine according to the invention as illustrated in FIG. 23. In particular, the state transition diagram of FIG. 23 represents a state machine 2310 that is equivalent to the one illustrated in FIG. 1. As described above, this configuration process includes having one or more of the possible transition events (A-H, FIG. 22) mapped by a system according to the invention to a detectable signal event or other system event, so that at least one of the eight possible system events causes a transition event to occur. This is preferably fully programmable.

From an initial state 2312, signal A 2314 causes a transition to a first state 2316, then signal B 2318 causes a transition to a second state 2320, then signal C 2322 causes a transition to a detection state 2324. Likewise, from the first state 2316, signal D 2326 causes a transition from the first state 2316 to a third state 2328, and then signal E 2330 causes a transition into the detection state 2324. And as in FIG. 1, observing signal F 2332 from the first state 2316 causes a transition to an end state 2334.

The state machine 2310 of FIG. 23 is topologically equivalent to the exemplary state machine 110 of FIG. 1; as set forth above, unused transition events (i.e., transitions out) for each state used should be configured such that no transition occurs should the corresponding signal event be observed. Alternatively, the unused transition events should be defined such that they never occur. Unused states need not be configured in any particular way, as no transition into said unused states is possible in the normal operation of a system according to the invention.

Figure 24:
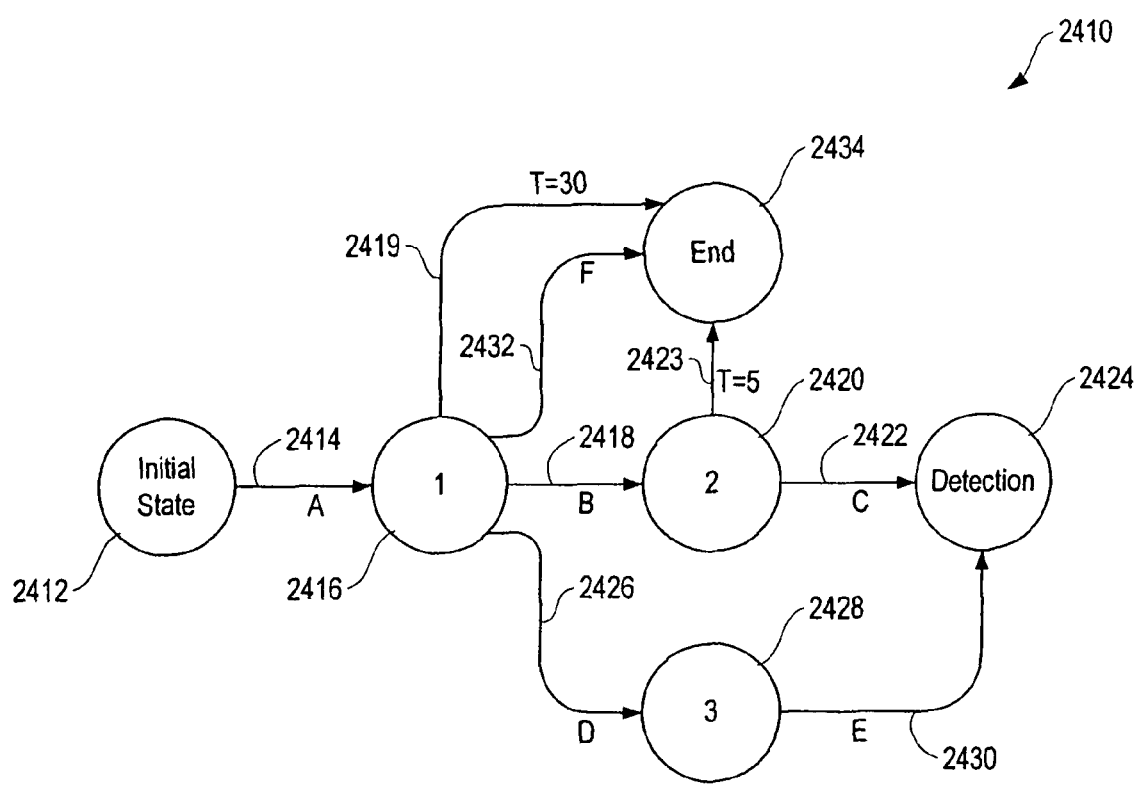
FIG. 24 is an exemplary time-dependent state transition diagram representing a finite state machine and including several possible sequences of signal events leading to a neurological event detection according to the invention.

The state transition diagram of FIG. 24 is similar to that of FIG. 1, but with an additional (an optional) capability present in an embodiment of the present invention: individual timeout values for each state. It will be recognized that it is also possible to accomplish this with time-based events (i.e., causing one or more of the eight possible transition events to be timer-driven), but that approach is less flexible, in that it uses up some of the limited number of transition events, and is not easily applied across the multiple state machine instances employed in an embodiment of the invention (which will be described in further detail below).

Referring now to FIG. 24, a state transition diagram representing an exemplary time-dependent state machine 2410 is set forth; such a state machine is capable of being represented by a system according to the invention, and as with FIG. 1, may represent several sequences of conditions that may be of interest for detecting neurological events.

In particular, hypothetically (and using the nomenclature introduced in FIG. 1), if a neurological event of interest is defined by the illustrated sequence of signal events where time is important, namely a "signal A" followed in no more than thirty seconds by a "signal B" followed in no more than five seconds by a "signal C," or alternatively signal A followed in no more than thirty seconds by a "signal D" followed (at any time) by a "signal E," but never includes signal A directly followed by a "signal F," then the state machine of FIG. 24 represents the conditions leading up to the neurological event.

In particular, starting with an initial state 2412, if signal A, 2414 is encountered, the state machine moves to a first state 2416. All of the combinations described above begin with signal A 2414. If signal A 2414 is followed by signal B 2418 within a first specified amount of time (an exemplary 30-second timeout 2419), then a second state 2420 is achieved, and if signal C 2422 is then observed before expiration of a second specified amount of time (an exemplary 5-second timeout 2423), then a detection state 2424 is reached, and a system according to the invention reacts accordingly. After the system acts as desired, the state machine 2410 generally will be reset to the initial state 2412 for further use.

After the first state 2416 is reached, if signal D 2426 is observed instead of signal B 2418, then the state machine transitions to a third state 2428. Following that, observation of signal E 2430 will cause the detection state 2424 to be reached, as above. Accordingly, two possible sequences of signal events lead to the detection state 2424: signal A 2414, then signal B 2418 within thirty seconds, then signal C 2422 within five seconds; or alternatively, signal A 2414, then signal D 2426 within thirty seconds, then signal E 2430.

Upon attainment of the detection state, the state machine of a system according to the invention has observed the combination of signals that was sought, and the system is actuated to respond accordingly (e.g. by providing responsive stimulation, changing modes, recording a record entry in the memory subsystem 526, or by performing some other action). Upon completion of the action, typically, the state machine is reset to the initial state 2412, but alternatively, a delay may be interposed or the state machine may be reprogrammed for detection of a different neurological event. There are other possibilities that will be apparent.

On the other hand, if after the first state 2416 is reached, signal F 2432 is encountered, then the state machine transitions to an end state 2434, and a system according to the invention performs any desired action (which may include resetting the state machine 2410 to the initial state 2412, either immediately or after a delay or some other action). In the illustrated example, two timeouts 2419 and 2423 cause the state machine to transition to the end state 2434, although it should be recognized that timeouts can be established in a system according to the invention to transition from any one state to any other state after a desired period of time, and that desired timeout expirations can be used along paths toward the detection state 2424 to ensure that state transitions do not occur too quickly.

Preferably, the transitions in a state machine according to the invention can be configured as either exclusive or nonexclusive transitions. An exclusive transition causes one state to be exited and another to be entered, while a nonexclusive transition is only one possible exit from a state; that same state can be exited subsequently by other signal events (and tracked in parallel). Considering this concept as applied to the state transition diagram of FIG. 24, it will be appreciated that the transitions out of the first state 2416 caused by signal B 2418 and signal D 2426 can be either exclusive or nonexclusive. If exclusive, then a transition via signal B 2418 will preclude a subsequent transition via signal D 2426, and vice versa. If nonexclusive, then both paths are available in parallel. This approach is highly flexible and configurable; it will be described in further detail below.

Figure 25:
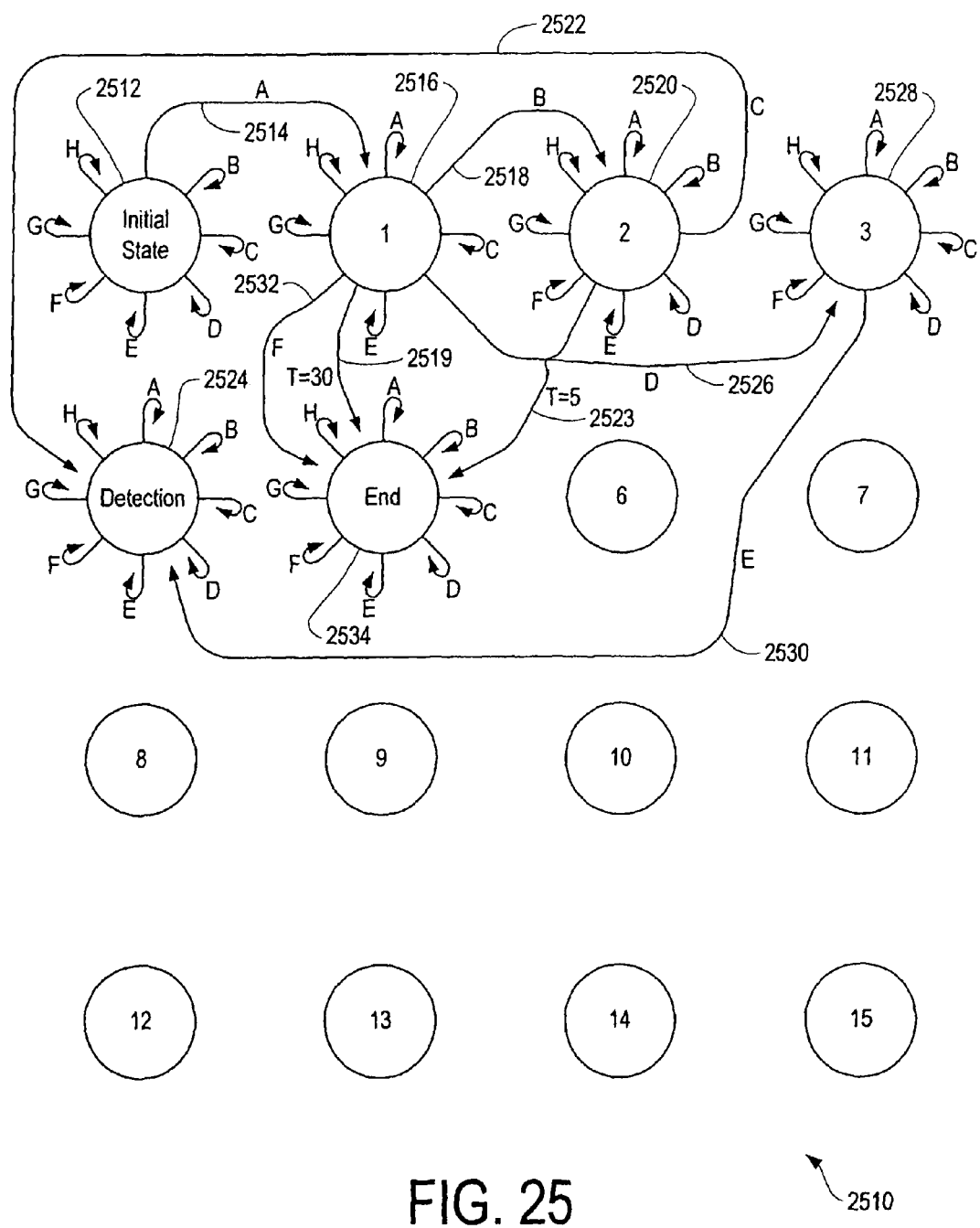
FIG. 25 is the state transition diagram of FIG. 24 as represented in a programmed implantable device according to the invention.

The states and transition events 2210 of FIG. 22 are configured into an exemplary state machine according to the invention as illustrated in FIG. 25. In particular, the state transition diagram of FIG. 25 represents a state machine 2510 that is equivalent to the one illustrated in FIG. 24.

From an initial state 2512, signal A 2514 causes a transition to a first state 2516, then signal B 2518 causes a transition to a second state 2520, then signal C 2522 causes a transition to a detection state 2524. Likewise, from the first state 2516, signal D 2526 causes a transition from the first state 2516 to a third state 2528, and then signal E 2530 causes a transition into the detection state 2524. And as in FIG. 24, observing signal F 2532 from the first state 2516 causes a transition to an end state 2534.

Similarly, with regard to timeouts, a first specified amount of time (an exemplary 30-second timeout 2519) causes a transition from the first state 2516 to the end state 2534, and a second specified amount of time (an exemplary 5-second timeout 2523) causes a transition from the second state 2520 to the end state 2534.

The state machine 2510 of FIG. 25 is topologically equivalent to the exemplary state machine 2410 of FIG. 24; as set forth above, unused transition events (i.e., transitions out) for each state used should be configured such that no transition occurs should the event be observed. Alternatively, the unused transition events should be defined such that they never occur. Unused states need not be configured in any particular way, as no transition into such unused states is possible in the normal operation of a system according to the invention.

As described above, a system according to the invention advantageously employs and processes finite state machines to identify temporal and spatiotemporal patterns and sequences of signals for the detection and prediction of neurological (or other) events. This is accomplished via data structures and constructions manipulated by the CPU 528 and memory subsystem 526 (FIG. 5) as set forth below.

A representation of a master state machine is stored in the memory subsystem 526 and, for reasons set forth below, is indexed by signal event. That is, the master state machine comprises a list of the eight possible signal events (some of which may be unused). Each signal-event-based entry contains, for each of the sixteen states in the master state machine, an indication of the destination state the signal event will cause a transition to. If the signal event is not a valid exit from one or more of the states, then a loopback to the same state (meaning, as described above and as illustrated in the Figures, no transition) is indicated.

Referring back to the state transition diagram of FIG. 25, an example may be illustrative. Signal E 2530 only allows one transition in the entire state machine, from the third state 2528 to the detection state 2524; in all other states signal E will not cause any transition (indicated in the Figures as a loop back to the same state). Accordingly, the event entry in the master state machine would be represented as follows in Table 1:

TABLE 1

EVENT ENTRY (SIGNAL E)

| STARTING STATE | DESTINATION STATE | EXCLUSIVE TRANSITION |
|---|---|---|
| Initial | Initial | Yes |
| 1 | 1 | Yes |
| 2 | 2 | Yes |
| 3 | Detection | Yes |
| Detection | Detection | Yes |
| End | End | Yes |
| 6 | 6 | Yes |
| 7 | 7 | Yes |
| 8 | 8 | Yes |
| 9 | 9 | Yes |
| 10 | 10 | Yes |
| 11 | 11 | Yes |
| 12 | 12 | Yes |
| 13 | 13 | Yes |
| 14 | 14 | Yes |
| 15 | 15 | Yes |

There is an instance of the foregoing representation for each of the possible transition events, A through H, in the master state machine. Accordingly, when a signal event is identified by a system according to the invention (as will be described in further detail below), it is a simple and efficient operation to determine whether that event causes any transitions, and if so, from and to which states. In the disclosed embodiment, this portion of the master state machine is 80 bytes in length: for each of the eight transition events, there are sixteen starting states, each of which indicates a four-bit representation of one of the sixteen possible destination states and a single bit indication of whether the transition to the destination state is exclusive. It should be noted that efficiency in storage and access, the fields of the master state machine (and other data structures described herein) may be packed differently than specifically described; the layout illustrated in the table above is for illustration only.

In an embodiment of the invention that includes state-based timeouts, as illustrated in FIGS. 24-25, the master state machine also includes a list of each state's possible timeout values. Accordingly, for each of the sixteen states there is a timeout duration value (in terms of an integer number of "timer ticks," described below) and a destination state. For instance, in the state transition diagram of FIG. 25, the second state 2520 has a timeout 2523 with a value of five seconds (T=5) that transitions to the end state 2534. In the disclosed embodiment, for each state (in the example, the second state 2520), the timeout value (in the example, five seconds) is stored as an unsigned eight-bit value (where zero indicates no timeout) and the destination state (in the example, the end state 2534) is stored in four bits. Therefore, each of the sixteen states requires twelve bits of timeout information, and for all sixteen states, the total is 24 bytes.

Consequently, the master state machine is represented in 88 bytes: 64 bytes for the event-indexed state transition table plus 24 bytes for the state-based timeout table.

TABLE 2

MASTER STATE MACHINE

| | |
|---|---|
| Event-Indexed State Transition Table | 8 events × 16 starting states × 4-bit destination = 64 bytes |
| State-Based Timeout Table | 16 states × (8-bit time value + 4-bit destination) = 24 bytes |

This information, once programmed into the implantable neurostimulator device 310 by the programmer 612 or some other apparatus, does not need to be updated by the device 310; it serves primarily as a lookup table as described below.

In addition to the master state machine described above, a system according to the invention includes multiple instances, or "snapshots" of the state machine driven by observed signal events. Multiple instances are needed to track parallel paths and resolve ambiguity caused particularly by different possible exits from the initial state and nonexclusive exits from other states in a state machine according to the invention.

TABLE 3

INSTANCE ENTRY

| | |
|---|---|
| Current State | 4 bits |
| Overall Life Remaining | 8 bits |
| State Life Remaining | 8 bits |

Each state machine instance includes the current state (one of sixteen possible states, represented in four bits), the overall life remaining in the state machine instance (that is, a representation of the time until the state machine instance "expires" and reverts back to its initial state, in eight bits of data), and the state life remaining of the state machine instance (a representation of the time until the instance's current state expires and must transition to a new state, also in eight bits of data).

In one embodiment of the invention, the overall life remaining and state life remaining values are stored in hardware-accessible registers in the detection subsystem 522 (FIG. 5) to permit efficient decrement-and-test operations to be performed as described below without the need for software intervention.

TABLE 4

STATE MACHINE INSTANCE LIST

| | |
|---|---|
| Instance List | 64 instances × 20-bit instance entry = 160 bytes |

In a preferred embodiment of the invention, there are 64 state machine instances, which is anticipated to be sufficient for comprehensive tracking of multiple exits from the initial state and parallel paths. As will be described in further detail below, the "oldest" of the instances in the instance list can be reused if necessary.

Figure 26:
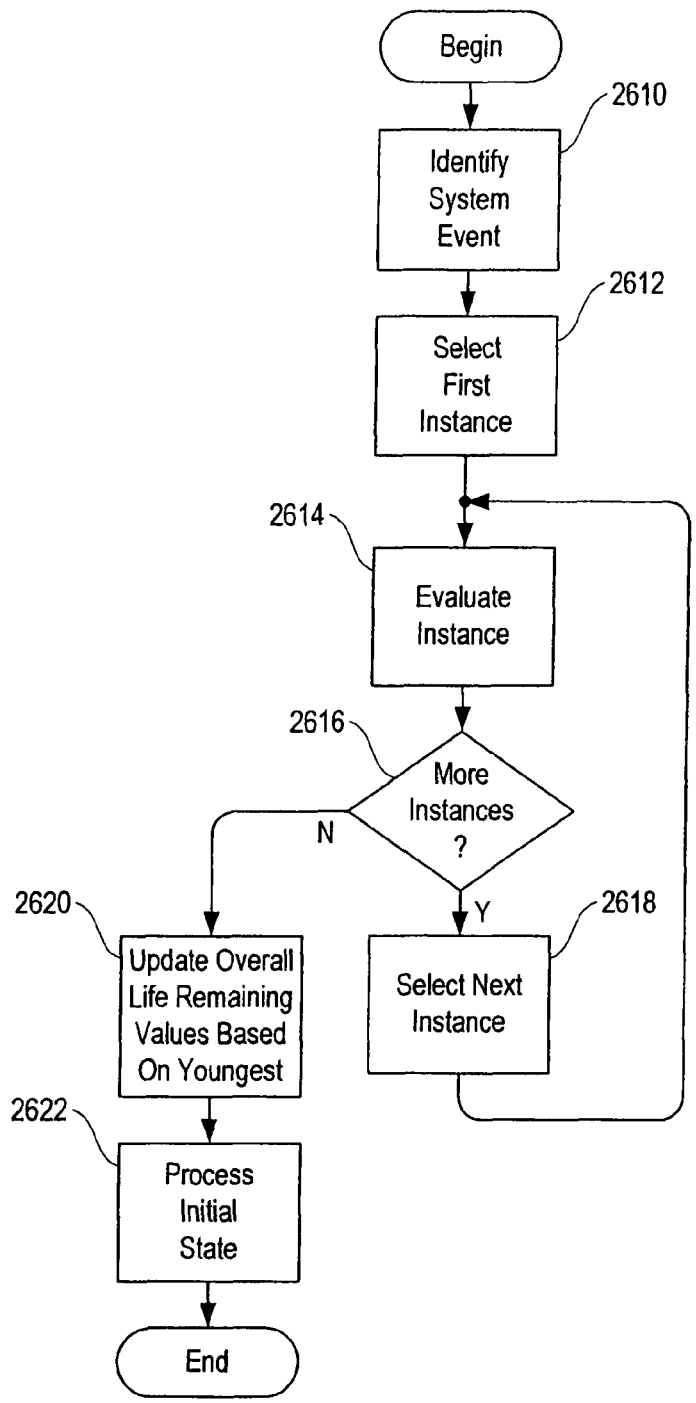
FIG. 26 is a flow chart illustrating the sequence of steps performed by a system according to the invention in detecting and predicting patterns via the state machine implementation of the invention upon the identification of a signal event.
Figure 27:
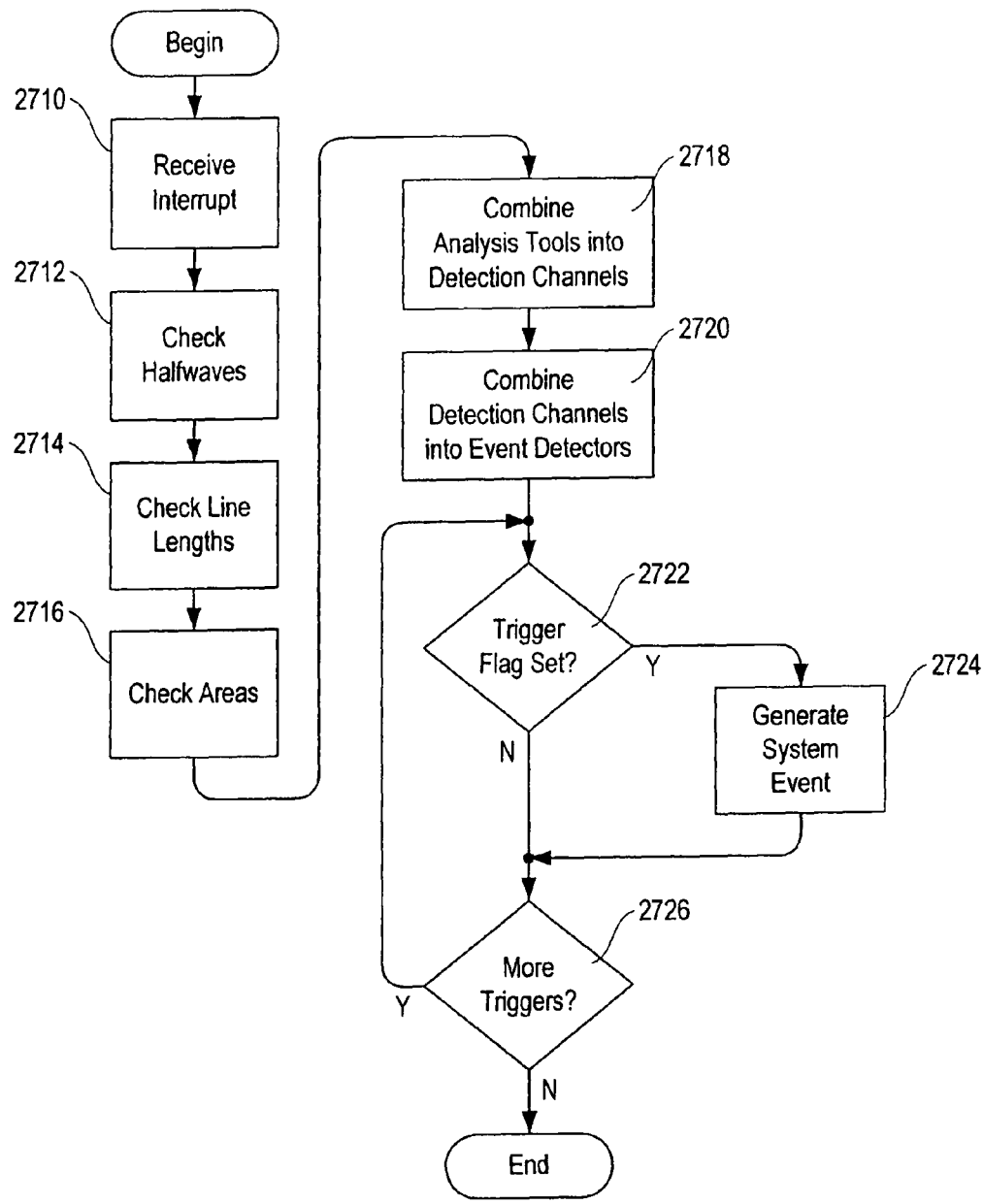
FIG. 27 is a flow chart illustrating the process performed by event-driven software in the central processing unit to analyze half wave, line length, and area information for detection according to the invention.
Figure 28:
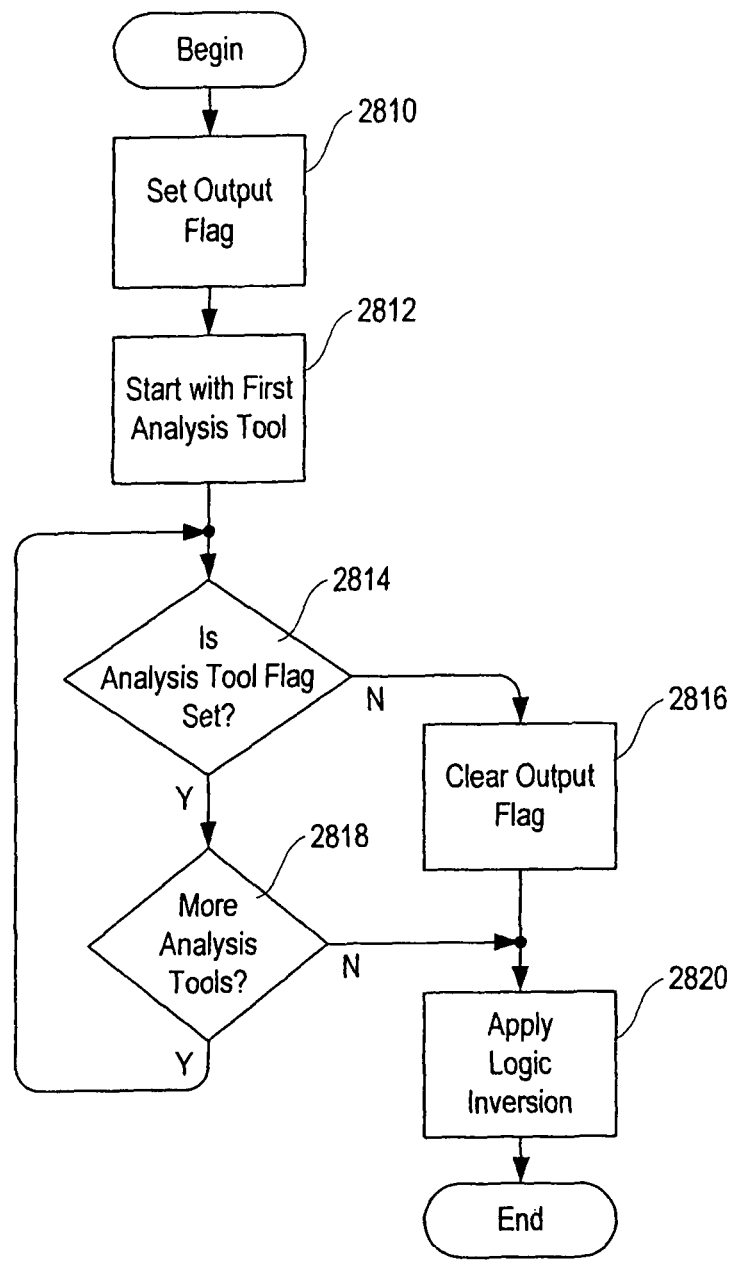
FIG. 28 is a flow chart illustrating the combination of analysis tools into detection channels in an embodiment of the invention.
Figure 29:
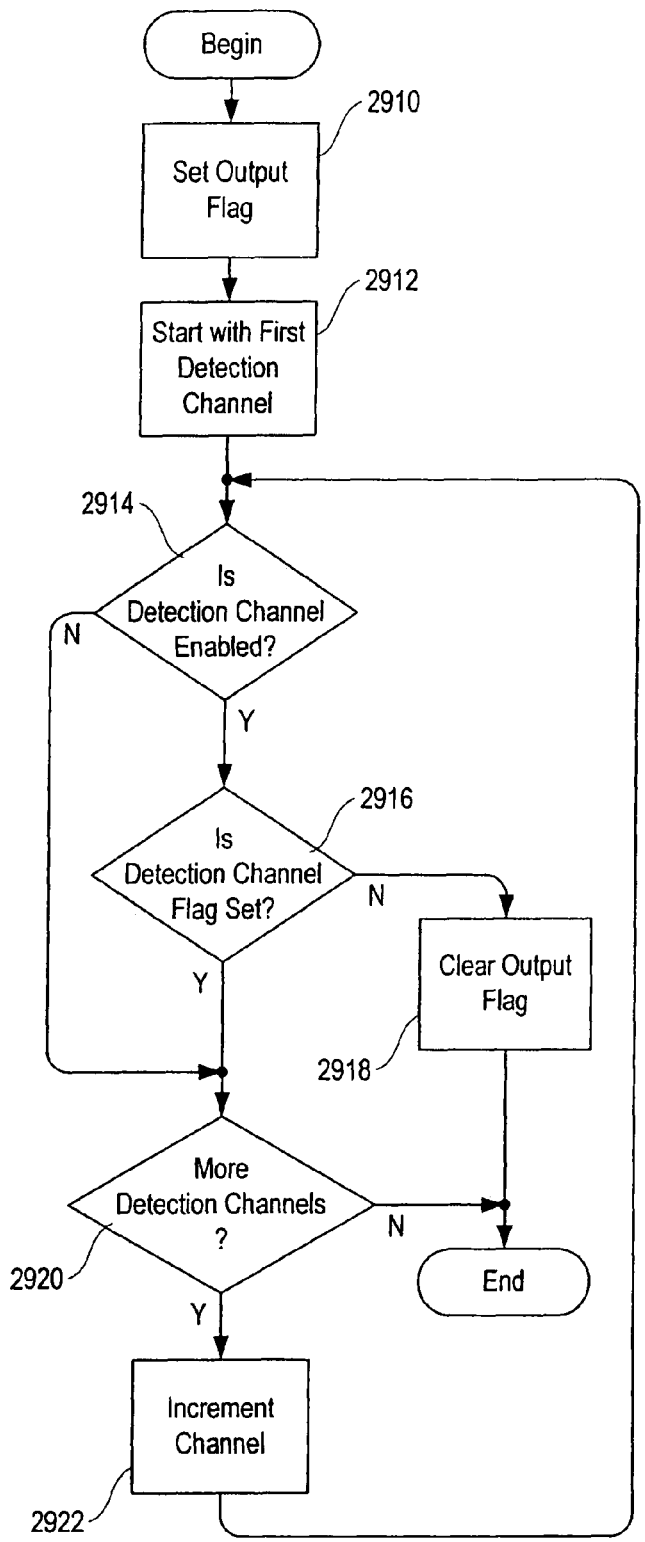
FIG. 29 is a flow chart illustrating the combination of detection channels into event detectors in an embodiment of the invention.

Referring now to FIG. 26, a flow chart is set forth illustrating a sequence of steps performed to update the state machine instances described above. Upon identification of a system event (step 2610), that is, a detection accomplished by the detection subsystem 522 or some other relevant event in the context of the neurostimulator device 310, as illustrated in FIGS. 27-29 below, the state machine instances described above are updated, if necessary, to account for the event.

In particular, the following procedure is followed. The first existing state machine instance in the instance list (described above) is selected (step 2612) and evaluated (step 2614)—that is, it is updated if necessary (i.e., state transitions are performed as described in further detail below, with reference to FIG. 30). If there are more instances in the instance list (step 2616), the next instance in the list is selected (step 2618) and the process continues until all existing state machine instances in the instance list have been evaluated.

If there are no more instances in the instance list (step 2616), then the overall life remaining values for the remaining state machine instances that have transitioned are updated (step 2620) to reflect the youngest instance in the same state. Specifically, as described in additional detail below with reference to FIG. 33, if multiple instances have transitioned into the same state because of the system event identified earlier (step 2610), then there is no need to keep track of those multiple instances—the only difference between them is their overall life remaining. Accordingly, the youngest instance is kept and other instances are discarded and returned to the initial state.

Finally, if the system event identified above (step 2610) is one that will bring the state machine out of its initial state, then a new state machine instance is initialized. This procedure will be described in greater detail below with reference to FIG. 32.

It will be recognized that the process illustrated in FIG. 26 is performed only once per relevant system event identified by a system according to the invention. Consequently, the method is relatively computationally efficient, as the CPU 528 can remain in a relatively inactive ("sleep") state most of the rest of the time, awakened only upon system event identification (such as a signal event detection from the detection subsystem 522). Alternatively, much of the process of FIG. 26 can be performed with custom hardware rather than the CPU 528, which has the potential to reduce power consumption even further.

An example of the multiple-state-machine-instance architecture of the invention may be illustrative. Starting from an initial time (for example, upon reset of an implantable neurostimulator device 310 according to the invention), all 64 state machine instances are in their initial state. For purposes of this example, event detectors in the detection subsystem 522 (FIG. 5) are updated once every second, and the "timer tick" resolution for updating state machine instance life remaining variables is also one second.

Assume, then, that a first signal event ("signal A" 2414, FIG. 24) is detected by the device 310, causing a system event to be asserted at each of three consecutive timer intervals. This would not necessarily be a common real-world occurrence, but it is possible in the disclosed embodiment for the invention for the situation to occur; this simplified example is presented here for clarity. Other behaviors may also be possible, such as to treat consecutive occurrences of the same signal event detection (either discrete detections or detections combined by persistence as described above) as a single system event, or to have a separate mechanism for determining when a system event is considered to end. Other possibilities will be evident to a practitioner of ordinary skill in the relevant arts.

At the first "timer tick," the first state machine (state machine instance no. 1, see Table 5 below) transitions from the initial state into the first state 2416 (FIG. 24), the overall life remaining value is set at 100 timer ticks, and the state life remaining value is set at 30 timer ticks (corresponding, in this example, to the 30-second timeout 2419 of FIG. 24). At the next timer tick, the overall life remaining value and the state life remaining value for instance no. 1 are decremented to 99 and 29, respectively, and since the first signal event (signal A) is still being detected, another instance is initialized: state machine instance no. 2 also transitions into the first state 2416 and receives overall and state life remaining values of 100 and 30, respectively. At the next timer tick, the life remaining values for instances 1 and 2 decrement again, and instance no. 3 is initialized as described above.

After the three consecutive observations of signal A, assume that signal B 2418 (FIG. 24) is then observed. At that point, instance no. 1 will transition to the second state 2420, the overall life remaining value is decremented once again to 97, and the state life remaining value is initialized at 5 (corresponding to the 5-second timeout 2423 of FIG. 24). Instances 2 and 3 remain in the first state but have their life remaining values decremented, and the remaining instances (4 through 64) are still in the initial state. This condition is illustrated in Table 5 below:

TABLE 5

STATE MACHINE INSTANCE EXAMPLE

| | Instance No. | | | | |
|---|---|---|---|---|---|
| | 1 | 2 | 3 | 4 | ... | 64 |
| Current State | 2 | 1 | 1 | Initial | ... | Initial |
| Overall Life Remaining Value | 97 | 98 | 99 | 0 | ... | 0 |
| State Life Remaining Value | 5 | 28 | 29 | 0 | ... | 0 |

It should be noted that while synchronous behavior is described above for simplicity (i.e., life remaining values are decremented when each event is processed); this is only a side effect of having the same timer tick interval for both signal event detection and life remaining processing, as described above. A system according to the invention allows for asynchronous handling of signal event detections and timer processing, as will be described in additional detail below.

The system events identified above (step 2610) are generated by the detection subsystem 522 and CPU 528 (FIG. 5) by the process illustrated in FIG. 27. This process of combining detection algorithm outputs (via outputs from the analysis units 912 and 914) begins with the receipt of a timer interrupt (step 2710), which is typically generated on a regular periodic basis to indicate the edges of successive time windows. Accordingly, in a system or method according to the disclosed embodiment of the invention, such a timer interrupt is received every 128 ms, or as otherwise programmed or designed. Then the half wave (step 2712, FIGS. 14-15), line length (step 2714, FIG. 18), and area (step 2716, FIG. 21) analysis tools are evaluated with respect to the latest data generated thereby, via the half wave analysis flag, the line length flag, and the area flag for each active channel. The steps of checking the analysis tools (steps 2712, 2714, and 2716) can be performed in any desired order or in parallel, as they are generally not interdependent. It should be noted that the foregoing analysis tools should be checked for every active channel, and may be skipped for inactive detection channels.

Flags, indicating whether particular signal characteristics have been identified in each active channel, for each active analysis tools, are then combined into detection channels (step 2718) as illustrated in FIG. 10. In the disclosed embodiment of the invention, this operation is performed as described in detail below with reference to FIG. 28. Each detection channel is a Boolean AND combination of analysis tool flags for a single channel, and as disclosed above, there are preferably at least eight channels in a system according to the invention.

The flags for multiple detection channels are then combined into event detector flags (step 2720), which are indicative of identified signal events or neurological events calling for action by the device, potentially a state machine transition. This process is described below, see FIG. 29, and is in general a Boolean combination of detection channels, if there is more than one channel per event detector.

If an event detector flag is set (step 2722), then a corresponding action is initiated (step 2724) by the device. Actions according to the invention can include the presentation of a warning to the patient, an application of therapeutic electrical stimulation, a delivery of a dose of a drug, an initiation of a device mode change, or a recording of certain EEG signals; it will be appreciated that there are numerous other possibilities. It is preferred, but not necessary, for actions initiated by a device according to the invention to be performed in parallel with the sensing and detection operations described in detail herein. It should be recognized that the application of electrical stimulation to the brain may require suspension of certain of the sensing and detection operations, as electrical stimulation signals may otherwise feed back into the detection subsystem 522 (FIG. 5), causing undesirable results and signal artifacts.

Multiple event detector flags are possible, each one representing a different combination of detection channel flags. If there are further event detector flags to consider (step 2726), those event detector flags are also evaluated (step 2722) and may cause further actions by the device (step 2724). It should be noted that, in general, actions performed by the device (as in step 2724) may be in part dependent on a device state—even if certain combinations of signal or neurological events do occur, no action may be taken if the device is in an inactive state, for example.

As described above, and as illustrated in FIG. 27 as step 2718, a corresponding set of analysis tool flags is combined into a detection channel flag as shown in FIG. 28 (see also FIG. 10). Initially the output detection channel flag is set (step 2810). Beginning with the first analysis tool for a particular detection channel (step 2812), if the corresponding analysis tool flag is not set (step 2814), then the output detection channel flag is cleared (step 2816).

If the corresponding analysis tool flag is set (step 2814), the output detection channel flag remains set, and further analysis tools for the same channel, if any (step 2818), are evaluated. Accordingly, this combination procedure operates as a Boolean AND operation—if any of the enabled and active analysis tools for a particular detection channel does not have a set output flag, then no detection channel flag is output by the procedure.

A clear analysis tool flag indicates that no detection has been made within the flag persistence period, and for those analysis tools that employ an X of Y criterion, that such criterion has not been met. In certain circumstances, it may be advantageous to also provide detection channel flags with logic inversion. Where a desired criterion (i.e., combination of analysis tools) is not met, the output flag is set (rather than cleared, which is the default action). This can be accomplished by providing selectable Boolean logic inversion (step 2820) corresponding to each event detector.

Also as described above, and as illustrated in FIG. 27 as step 2720, multiple detection channel flags are combined into a single event detector flag as shown in FIG. 29 (see also FIG.

8). Initially the output event detector flag is set (step 2910). Beginning with the first detection channel for a particular event detector (step 2912), if the channel is not enabled (step 2914), then no check is made. If the channel is enabled and the corresponding detection channel flag is not set (step 2916), then the output event detector flag is cleared (step 2918) and the combination procedure exits. If the corresponding detection channel flag is set (step 2916), the output event detector flag remains set, and further detection channels, if any (step 2920), are evaluated after incrementing the channel being considered (step 2922). Accordingly, this combination procedure also operates as a Boolean AND operation—if any of the enabled and active detection channels does not have a set output flag, then no event detector flag is output by the procedure. It should also be observed that a Boolean OR combination of detection channels may provide useful information in certain circumstances; a software or hardware flow chart accomplishing such a combination is not illustrated, but could easily be created by an individual of ordinary skill in digital electronic design or computer programming.

An implantable version of a system according to the invention advantageously has a long-term average current consumption on the order of 10 microamps, allowing the implanted device to operate on power provided by a coin cell or similarly small battery for a period of years without need for replacement. It should be noted, however, that as battery and power supply configurations vary, the long-term average current consumption of a device according to the invention may also vary and still provide satisfactory performance.

Figure 30:
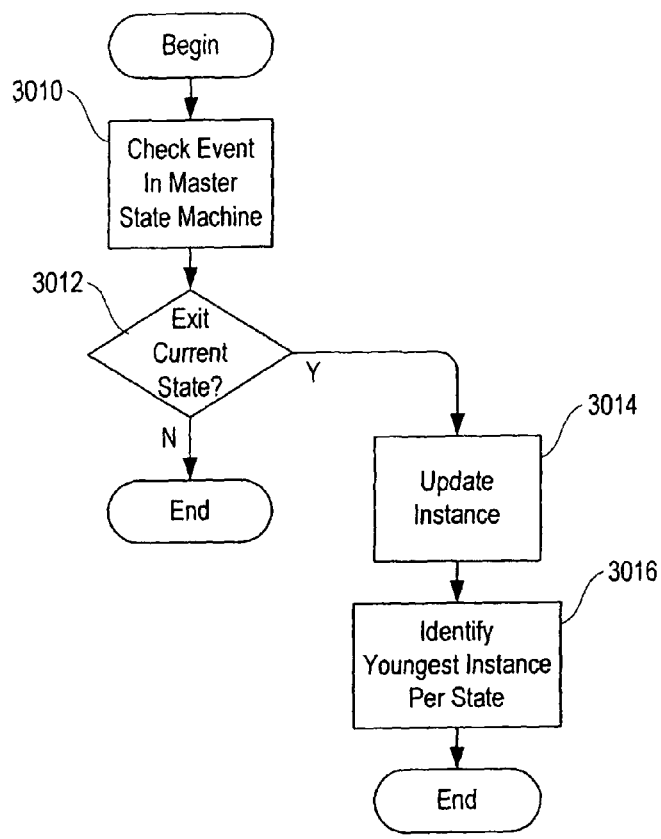
FIG. 30 is a flow chart illustrating the steps performed in evaluating a state machine instance according to the procedure of FIG. 26.

The method by which individual state machine instances are evaluated (step 2614, FIG. 26) upon identification of a system event (FIG. 27) is illustrated in FIG. 30. Initially, based on the previously identified system event (step 2610, FIG. 26), the master state machine is accessed to identify what state (or states) the system event allows a transition out of (step 3010).

If the current state of the instance being evaluated is a state that the identified system event allows a transition out of (step 3012), then the instance is updated (step 3014) by transitioning the instance into the appropriate new state (once again, by accessing the master state machine) and resetting the state life remaining to the appropriate new value. Additional details of this step will be described below with reference to FIG. 33. The overall life remaining of the instance being evaluated is then recorded to identify which instance is youngest (step 3016), if multiple instances are in the same state. This information is used to eliminate redundant state machine instances as described above in connection with FIG. 26. If no transition is indicated (step 3012), then the process ends.

As described in general above, each of the state machine instances includes a state life remaining and an overall life remaining. The overall life remaining value enables "expiration" of a state machine instance if it is taking too long to match a pattern. The state life remaining value allows any state to have a timeout value, i.e., a maximum time for a state to remain valid. Accordingly, a system according to the invention includes a timer processing function enabled by the clock supply 534 (FIG. 5).

In an embodiment of the invention, the state life remaining variable and the overall life remaining variable are both eight-bit values, each with a resolution of 64 ms (and hence a maximum value of 16 seconds). Preferably, the resolution of the state life remaining variable and the overall life remaining variable are independently programmable from a range of values, for example 4 ms to 256 ms in power-of-two steps.

Figure 31:
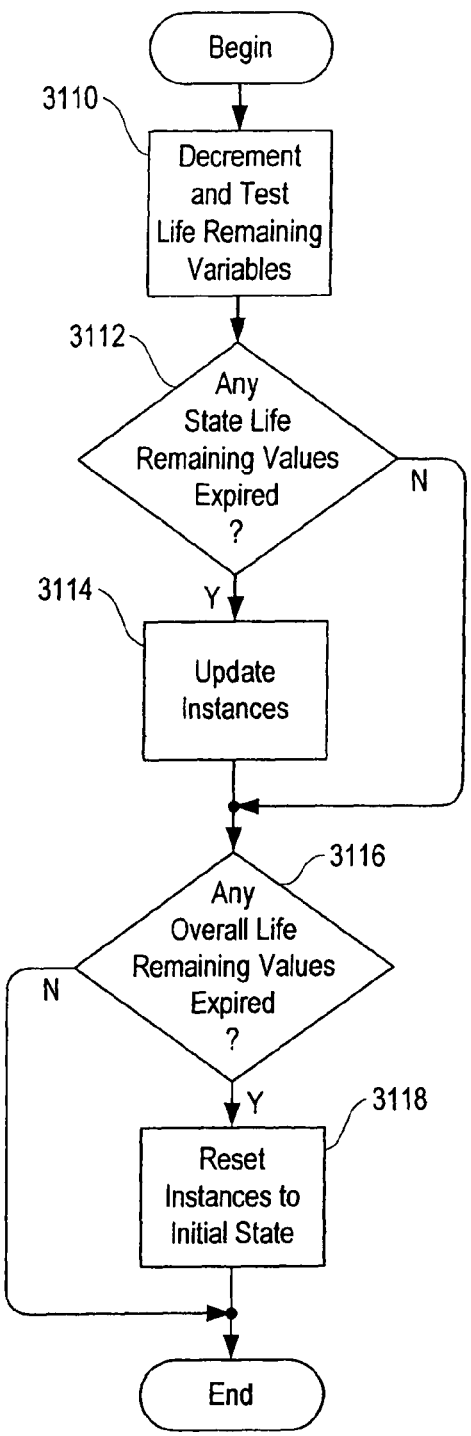
FIG. 31 is a flow chart illustrating the steps performed in time-based processing of state machine instances according to the invention.

Every "timer tick," i.e. every 64 ms if the state life remaining and overall life remaining variables are programmed as set forth above, the process set forth in FIG. 31 is performed to determine whether any state machine instances will expire or transition based on elapsed time. For purposes of this disclosure, it is assumed that both variables have the same resolution. If not, it will be appreciated that state life remaining and overall life remaining would generally be handled separately, not together as illustrated in FIG. 31.

As described above, each instance maintains a state life remaining value and an overall life remaining value. Upon each timer tick, a system according to the invention will decrement and test those variables (step 3110) in each active state machine instance. If one or more of the state life remaining values have expired (step 3112), i.e., reached zero, the corresponding state machine instances are updated (step 3114) by transitioning the instances into the appropriate new states (once again, by accessing the master state machine) and resetting the state life remaining variable to the appropriate new value. Additional details of this step will be described below with reference to FIG. 33. If one or more of the overall life remaining values have expired (step 3116), or reached zero, those instances are reset to the initial state (step 3118).

When an end state is reached (e.g. the end state 2534, FIG. 25), either via timeout or system event, a system according to the invention is preferably programmable to perform any desired action. For example, in an embodiment of the invention, the system may be programmed to record a diagnostic record in the memory subsystem 526 (FIG. 5), delay for a few seconds, and reset to the initial state. Other possibilities will be evident and are considered to be within the scope of the present invention.

Similarly, when a detection state is reached (e.g. the detection state 2524, FIG. 25), a system according to the invention is programmable to perform an action, typically the delivery of therapy or some mode change related to treatment. For example, electrical stimulation (tailored to the type of detection that was made) may be delivered, or the system (and particularly the detection subsystem 522) may be put into a heightened state of alert for subsequent detections. Other possibilities are set forth herein, and will be apparent to a practitioner of ordinary skill. Such variations and others are deemed to be within the scope of the present invention.

Figure 32:
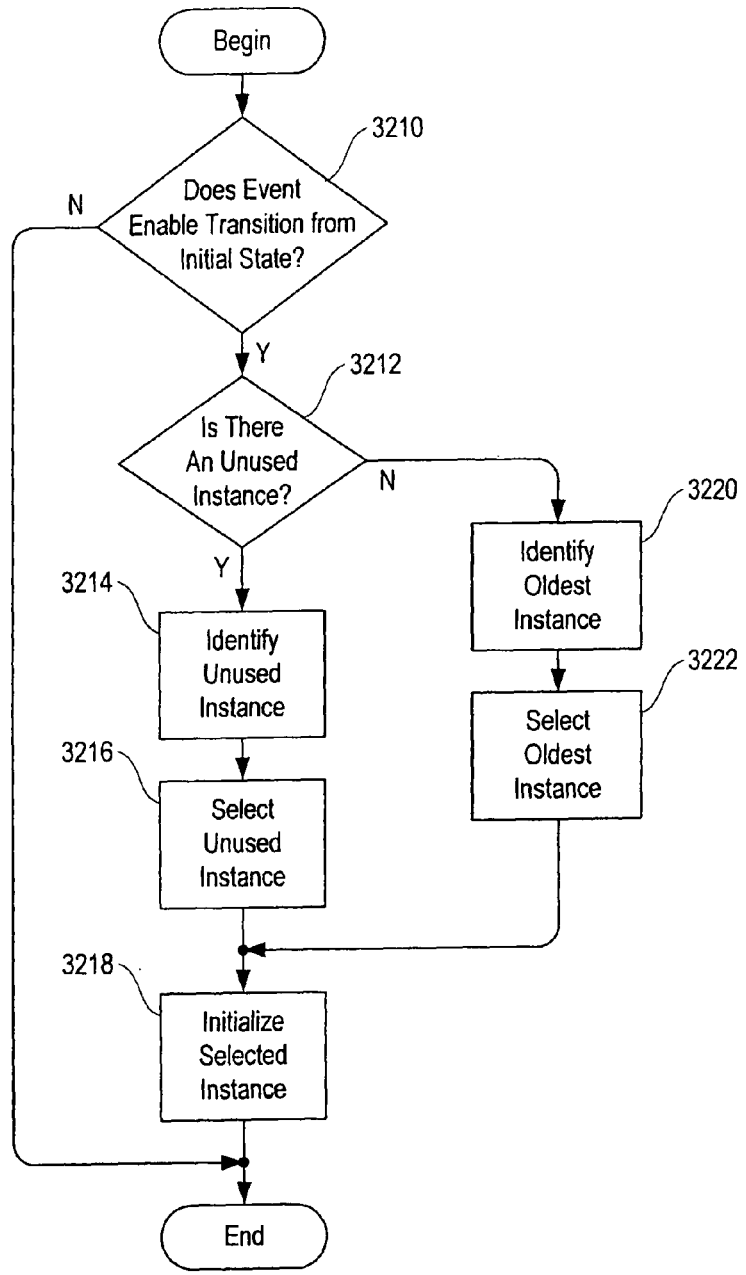
FIG. 32 is a flow chart illustrating the steps performed in processing transitions from an initial state according to the procedure of FIG. 26.

Transitions out of the state machine's initial state are handled according to the process illustrated in FIG. 32, which is performed after every system event is identified (at step 2622, FIG. 26).

If a previously identified system event (step 2610, FIG. 26) allows a transition out of the master state machine's initial state (step 3210), then it is first determined whether there is an unused state machine instance in the instance list (step 3212). An unused state machine instance is one in its initial state; while a state machine instance is in the initial state, the state life remaining and overall life remaining variables are not meaningful, and hence, they are not updated.

If an unused state machine instance is available, then one is identified (step 3214), selected for use (step 3216), and initialized (step 3218) by making the appropriate transition out of the initial state (as indicated by the master state machine), and setting the overall life remaining and state life remaining variables to their appropriate values (as also indicated by the master state machine).

If no unused state machine instance is available, then the state machine instance with the smallest overall life remaining value (i.e., closest to expiration) is identified (step 3220), selected for use (step 3222), and initialized (step 3218) as before. Accordingly, this allows the use of a shorter list of state machine instances than would otherwise be possible, where all possible permutations of overall life remaining values are preserved.

Figure 33:
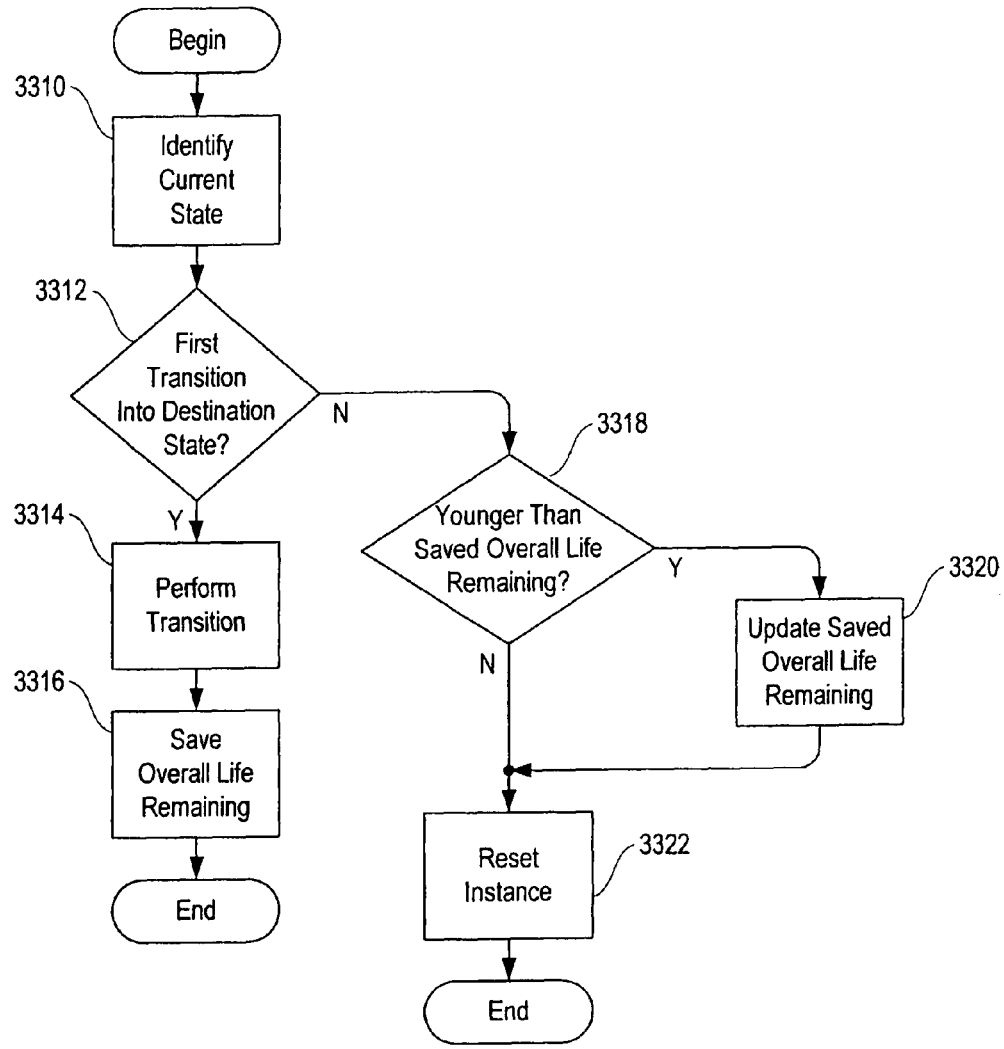
FIG. 33 is a flow chart illustrating the steps performed in updating a state machine instance to perform a transition according to the procedure of FIG. 30.

A state machine instance is updated (as in step 3014, FIG. 30, and step 3114, FIG. 31) as illustrated in the flow chart of FIG. 33.

The current state of the current state machine instance is first identified (step 3310). If this is the first transition into the destination state (step 3312) for the system event being processed (identified at step 2610, FIG. 26), then the appropriate transition is performed (step 3314, illustrated in detail in FIG. 34), based on information in the master state machine, and the overall life remaining variable of the current state machine instance is saved (step 3316) for this system event and this target state in the memory subsystem 526 (FIG. 5); it will be used later (it is generally stored in a temporary storage area, and only for the duration of the current pass through the process of FIG. 26).

On the other hand, if this is not the first transition out of the current state (step 3312), and other state machine instances have made the same transitions previously (during the servicing of the current system event), then the overall life remaining of the current state machine instance is compared to the saved (youngest) overall life remaining (from step 3316, above). If the current state machine instance is younger (step 3318), then the saved overall life remaining is updated to reflect the younger overall life remaining (step 3320), and the current state machine instance is reset to an unused state (step 3322). If the current state machine instance is not newer, then the saved overall life remaining is not changed and the current state machine instance is initialized (step 3322). As set forth above, the saved life remaining value is used to update only one of the state machine instances, while others in the same state (but with smaller overall life remaining values) are discarded. See FIG. 26, step 2620.

Figure 34:
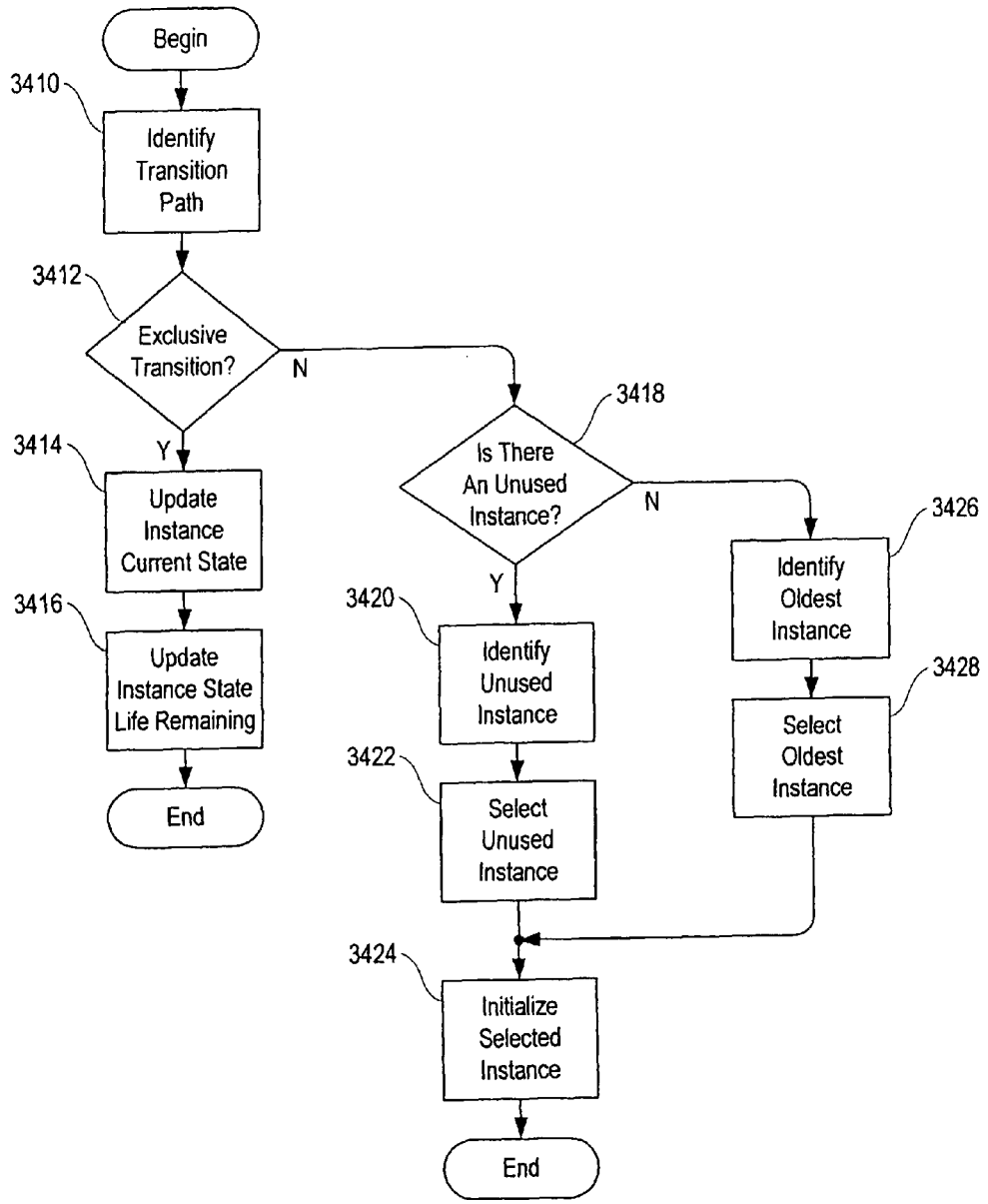
FIG. 34 is a flow chart illustrating the steps performed in transitioning from one state to another as illustrated in FIG. 33 in a system according to the invention.

Transitions from state to state are performed in an embodiment of the invention according to the process illustrated in FIG. 34. Initially the proper transition path in the master state machine is identified (step 3410), thereby selecting the proper destination state and exclusivity status associated with the current system event and current state. If the transition path is an exclusive one (step 3412) as indicated in the master state machine, then the current state of the instance being processed is updated to reflect the destination state (step 3414) and the state life remaining is also updated to the appropriate value (step 3416).

On the other hand, if the transition is nonexclusive (step 3412), a separate instance is spawned as set forth below. If there is an unused instance in the instance list (step 3418), i.e. one that is in the initial state, that unused instance is identified (step 3420) and selected (step 3422). The selected instance is then initialized (step 3424) to appropriate values: the current state of the selected instance is set to reflect the destination state (selected at step 3410, above), the state life remaining is set appropriately, and the overall life remaining is set to the same value as that of the original instance (the instance having the transition that is spawning the new instance).

If there is no unused instance (step 3418), then the oldest existing instance is identified (step 3426) and selected for reuse (step 3428). The reused instance is then initialized as described above.

Consequently, then, the result of a nonexclusive transition is that two instances are created out of a single instance's transition. One instance remains in its current state (and its life remaining values are unchanged), while the other instance makes the transition. Accordingly, returning to the exemplary state machine of FIG. 1, if the signal B 118 and signal D 126 transitions out of the first state 116 are nonexclusive, then it is possible to detect the sequence A>B>D>E as a valid detection sequence (upon detection of signal B 118, one instance transitions to the second state 120 while one remains in the first state 116). There are other possibilities as well. That is, the occurrence of signal B 118 is not the exclusive path out of the first state 116. One constructive approach to understanding the utility of nonexclusive transitions is to think of the A>B>D>E sequence set forth above as A>(B)>D>E, where the operative detection sequence is A>D>E, as expressly illustrated in FIG. 1—where the intervening signal B 118 is detected but does not disrupt the detection sequence. It will be appreciated that the approach set forth herein provides a great deal of flexibility.

If the transitions of FIG. 1 are exclusive, then A>B>D>E will not be detected; the transition caused by signal B 118 from the first state 116 to the second state 120 precludes the subsequent transition into the third state 128 when signal D 126 is encountered. Accordingly, detecting signal B 118 will disrupt the A>D>E pattern, and detecting signal D 126 will disrupt the A>B>C pattern.

Both approaches have their advantages; as described herein a system according to the invention can be selectively configured to implement state machines including both exclusive and nonexclusive transitions as clinically desired.

It should be noted that transitions to an end state, such as the transition caused by signal F 132 of FIG. 1, should generally be exclusive—there is believed to be little reason to end a newly-spawned instance while allowing another instance to continue. Similarly, where there is only a single valid transition out of a state, it should generally be configured as exclusive.

It should be observed that while the foregoing detailed description of various embodiments of the present invention is set forth in some detail, the invention is not limited to those details and an implantable neurostimulator or neurological disorder detection device made according to the invention can differ from the disclosed embodiments in numerous ways. In particular, it will be appreciated that embodiments of the present invention may be employed in many different applications to detect anomalous neurological patterns and sequences in at least one portion of a patient's brain. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries.

It will be apparent that the exemplary state machines set forth herein are intended to be illustrative and not limiting. It is possible to employ more or fewer than sixteen states or more or fewer than eight possible transition events, or to encode timeouts differently, to name but a few possibilities. It should be recognized that increased storage space will be required for increases in either the number of transition events or the number of states, but little performance penalty will be incurred. Similarly, more or fewer than 64 state machine instances can be employed by a system according to the invention. Additional execution time may be required to process additional instances.

The appropriate scope hereof is deemed to be in accordance with the claims as set forth below.

What is claimed is:

1. An implantable medical device, comprising:
a sensing subsystem configured to sense electrical activity from a patient's brain;
a detection subsystem configured to detect a set of signal events based on the sensed electrical activity;
a configurable finite state machine comprising:
a representation of a set of states;
a representation of a set of transition events, wherein an occurrence of a first transition event of the set of transition events causes a first transition out of a first state, the first transition being one of an exclusive transition from the first state or a non-exclusive transition from the first state, and wherein an occurrence of a second transition event of the set of transition events may cause a second transition out of the first state; and
a representation of the set of signal events, wherein a first detected signal event of the set of signal events is mapped to the first transition event, a second detected signal event of the set of signal events is mapped to the second transition event, wherein the first detected signal event, once mapped to the first transition event, causes the first transition to occur, and the second detected signal event, once mapped to the second transition event, causes the second transition to occur when the first transition is a non-exclusive transition, and to not occur when the first transition is an exclusive transition;
a central processing unit configured, in conjunction with the configurable finite state machine, to determine whether at least two individual detected signal events of the set of signal events occur in at least one of a predetermined pattern and sequence representative of a neurological event,
wherein the central processing unit selects a response, from a predetermined menu of possible responses, whenever the predetermined pattern and sequence of the at least two individual neurological events is determined to have occurred.

2. The implantable medical device of claim 1, wherein the predetermined sequence includes requiring that a second signal event occurs within a predetermined time period of a first signal event.

3. The implantable medical device of claim 1, wherein the detection subsystem detects signal events based on morphological characteristics of the sensed electrical activity.

4. The implantable medical device of claim 3, wherein the morphological characteristics are half waves.

5. The implantable medical device of claim 1, wherein the detection subsystem detects signal events based on characteristics of sensed electrical activity normalized to a particular window of time of a predetermined length.

6. The implantable medical device of claim 5, wherein the time window-normalized characteristics are the sum of the line lengths in the window or the total area under the curve in the window.

7. The implantable medical device of claim 1, wherein the detection subsystem detects signal events based on a combination of morphological characteristics of the sensed electrical activity and characteristics of the sensed electrical activity normalized to a particular window of time of a predetermined length.

8. The implantable medical device of claim 1, wherein the menu of possible responses includes one or more of registering detection of a predefined neurological condition, initiating a therapy, and generating a warning.

9. The implantable medical system of claim 1, further comprising at least one implantable electrode coupled to the stimulation subsystem and adapted to deliver electrical stimulation to the patient.

10. The implantable medical system of claim 9, wherein the at least one implantable electrode adapted to deliver electrical stimulation to the patient is also coupled to the sensing subsystem and adapted to sense the electrical activity from the patient.

* * * * *